United States Patent
Gao et al.

(10) Patent No.: US 11,946,066 B2
(45) Date of Patent: Apr. 2, 2024

(54) RNA-BASED DELIVERY SYSTEMS WITH LEVELS OF CONTROL

(71) Applicant: California Institute of Technology, Pasadena, CA (US)

(72) Inventors: Xiaojing Gao, Pasadena, CA (US); Lucy S. Chong, Pasadena, CA (US); Michael B. Elowitz, Pasadena, CA (US); Matthew S-M Kim, San Francisco, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 17/935,024

(22) Filed: Sep. 23, 2022

(65) Prior Publication Data

US 2023/0193317 A1 Jun. 22, 2023

Related U.S. Application Data

(63) Continuation of application No. 16/555,604, filed on Aug. 29, 2019, now Pat. No. 11,453,893.

(60) Provisional application No. 62/777,420, filed on Dec. 10, 2018, provisional application No. 62/725,020, filed on Aug. 30, 2018.

(51) Int. Cl.
| | | |
|---|---|---|
| *C12N 15/86* | (2006.01) | |
| *C07K 14/005* | (2006.01) | |
| *C07K 14/81* | (2006.01) | |
| *C07K 16/18* | (2006.01) | |
| *C12N 7/00* | (2006.01) | |
| *C12N 9/50* | (2006.01) | |
| *C12N 15/62* | (2006.01) | |

(52) U.S. Cl.
CPC ............ *C12N 15/86* (2013.01); *C07K 14/005* (2013.01); *C07K 16/18* (2013.01); *C12N 7/00* (2013.01); *C12N 9/506* (2013.01); *C12N 15/62* (2013.01); *C12Y 304/21098* (2013.01); *C07K 2317/569* (2013.01); *C07K 2317/622* (2013.01); *C07K 2319/30* (2013.01); *C07K 2319/50* (2013.01); *C12N 2740/11045* (2013.01); *C12N 2760/20143* (2013.01); *C12N 2810/6054* (2013.01); *C12N 2820/002* (2013.01); *C12N 2820/007* (2013.01)

(58) Field of Classification Search
CPC .................... C12N 15/86; C12N 9/506; C12N 2740/11045; C12N 2820/007; C07K 2319/50
See application file for complete search history.

(56) References Cited

U.S. PATENT DOCUMENTS

| | | | |
|---|---|---|---|
| 5,739,002 A | 4/1998 | De Francesco et al. | |
| 6,005,079 A | 12/1999 | Casterman et al. | |
| 6,348,584 B1 | 2/2002 | Hodgson et al. | |
| 6,673,901 B2 | 1/2004 | Koide | |
| 6,884,870 B2 | 4/2005 | Hav et al. | |
| 8,394,604 B2 | 3/2013 | Liu et al. | |
| 2002/0132327 A1 | 9/2002 | Hay et al. | |
| 2005/0271647 A1 | 12/2005 | Baltimore et al. | |
| 2009/0162341 A1 | 6/2009 | Foster et al. | |
| 2013/0230863 A1 | 9/2013 | Tang et al. | |
| 2017/0315114 A1 | 11/2017 | Stein et al. | |
| 2018/0118818 A1 | 5/2018 | Tang et al. | |
| 2019/0248873 A1 | 8/2019 | Gao et al. | |

FOREIGN PATENT DOCUMENTS

| | | |
|---|---|---|
| WO | WO1994004678 | 3/1994 |
| WO | WO1994025591 | 11/1994 |
| WO | WO2014040129 | 3/2014 |
| WO | WO2018069782 | 4/2018 |
| WO | WO2019147478 | 8/2019 |

OTHER PUBLICATIONS

Adams et al., "Overview and analysis of the polyprotein cleavage sites in the family Potyviridae," Molecular Plant Pathology 2005, 6(4), 471-487.
Angelic! et al., "Synthetic Biology Platform for Sensing and Integrating Endogenous Transcriptional Inputs in Mammalian Cells," Cell Reports 2016, 16, 2525-2537.
Aronheim et al., "Membrane Targeting of the Nucleotide Exchange Factor Sos Is Sufficient for Activating the Ras Signaling Pathway," Cell 1994, 78 , 949-961.
Auslander et al., "Programmable single-cell mammalian biocomputers," Nature 2012, 487, 123-127.
Banaszynski et al., "A Rapid, Reversible, and Tunable Method to Regulate Protein Function in Living Cells Using Synthetic Small Molecules," Cell 2006, 126, 995-1004.
Barnea et al., "The genetic design of signaling cascades to record receptor activation," PNAS 2008, 105(1), 64-69.
Barrett et al., "Chimeric Antigen Receptor Therapy for Cancer," Annual Review of Medicine 2014, 65, 333-347.
Bartenschlager et al., "The NS3/4A proteinase of the hepatitis C virus: unravelling structure and function of an unusual enzyme and a prime target for antiviral therapy," Journal of Viral Hepatitis 1999, 6, 165-181.

(Continued)

*Primary Examiner* — Barry A Chestnut
(74) *Attorney, Agent, or Firm* — Sheppard, Mullin, Richter & Hampton LLP

(57) ABSTRACT

Disclosed herein include methods, compositions, and systems suitable for use in delivering a polynucleotide to a target cell of a subject in need thereof. In some embodiments, a viral vector comprises a polynucleotide encoding nucleoprotein (N), phosphoprotein (P), matrix protein (M), RNA-dependent RNA polymerase (L), and one or more transgenes. The viral vector can comprise one or more of a conditionally stable fusion protein, a protease fusion protein, a degron fusion protein, and/or a glycoprotein derived of another species than the viral vector polynucleotide to enable control of viral vector transduction and/or replication.

20 Claims, 19 Drawing Sheets

Specification includes a Sequence Listing.

(56) References Cited

OTHER PUBLICATIONS

Basu et al., "A synthetic multicellular system for programmed pattern formation," Nature 2005, 434, 1130-1134.
Basu et al., "Spatiotemporal control of gene expression with pulse-generating networks," PNAS 2004, 101(17), 6355-6360.
Bintu et al., "Dynamics of epigenetic regulation at the single-cell level," Science 2016, 351(6274), 720-724.
Boerger et al., "Retroviral vectors preloaded with a viral receptor-ligand bridge protein are targeted to specific cell types," PNAS 1999, 96, 9867-9872.
Bonnet et al., "Amplifying Genetic Logic Gates," Science 2013, 340, 599-602.
Budihardjo et al., "Biochemical Pathways of Caspase Activation During Apoptosis," AnnualReview of Cellular Development and Biology 1999, 15, 269-290.
Butko et al., "Fluorescent and photo-oxidizing TimeSTAMP tags track protein fates in light and electron microscopy," Nature Neuroscience 2012, 15(12), 1742-1751.
Camacho-Soto et al., "Ligand-Gated Split-Kinases," Journal of the American Chemical Society 2014, 136, 3995-4002.
Camacho-Soto et al., "Small Molecule Gated Split-Tyrosine Phosphatases and Orthogonal Split-Tyrosine Kinases," Journal of the American Chemical Society 2014, 136, 17078-17086.
Carrington et al., "A viral cleavage site cassette: Identification of amino acid sequences requiredfor tobacco etch virus polyprotein processing," PNAS 1988, 85, 3391-3395.
Chen et al., "Predicting PDZ domain-peptide interactions from primary sequences," Nature Biotechnology 2008, 26(9), 1041-1045.
Choi et al., "Selective viral vector transduction of ErbB4 expressing cortical interneurons in vivo with a viral receptor-ligand bridge protein," PNAS 2010, 107(38), 16703-16708.
Chung et al., "Tunable and reversible drug control of protein production via a self-excising degron," Nature Chemical Biology 2015, 11, 713-720.
Corrected Notice of Allowability dated Jun. 29, 2022 in U.S. Appl. No. 16/555,604.
Cox et al., "Drugging the undruggable Ras: mission possible?," Nature Reviews Drug Discovery 2014, 13(11), 828-851.
Dagliyan et al., "Computational design of chemogenetic and optogenetic split proteins," Nature Communications, 9(4042), 1-8.
Daringer et al., "Modular Extracellular Sensor Architecture for Engineering Mammalian Cell-based Devices," ACS Synthetic Biology 2014, 3, 892-902.
De Felipe et al., "Targeting of Proteins Derived from Self-Processing Polyproteins Containing Multiple Signal Sequences," Traffic 2004, 5, 616-626.
De Felipe, "Skipping the co-expression problem: the new 2A "CHYSEL" technology," Genetic Vaccines and Therapy 2004, 2(13).
Downward, "Targeting RAS Signaling Pathways in Cancer Therapy," Nature Publishing Group 2003, 3, 11-22.
Dueber et al., "Reprogramming Control of an Allosteric Signaling Switch Through Modular Recombination," Science 2003, 301, 1904-1908.
Elowitz et al., "A synthetic oscillatory network of transcriptional regulators," Nature 2000, 403, 335-338.
Fernandez-Rodriguez et al., "Post-translational control of genetic circuits using Potyvirus proteases," Nucleic Acids Research 2016, 44(13), 6493-6502.
Ferrell et al., "Ultrasensitivity Part II: Multisite phosphorylation, stoichiometric inhibitors, and positive feedback," Trends in Biochemical Sciences 2014, 39(11), 556-569.
Fink et al., "Design of fast proteolysis-based signaling and logic circuits in mammalian cells," Nature Chemical Biology 2018, 15, 115-122.
Gao et al., "Programmable protein circuits in living cells," Science 2018, 361, 1252-1258.
Gardner et al., "Construction of a genetic toggle switch in *Escherichia coli*," Nature, 403, 339-342.
Ghabrial et al., "Molecular genetic analyses of the soybean mosaic virus Nia proteinase," Journal of General Virology 1990, 71, 1921-1927.
Ghosh et al., "Antiparallel Leucine Zipper-Directed Protein Reassembly: Application to the Green Fluorescent Protein," Journal of the American Chemical Society 2000, 122, 5658-5659.
Gramespacher et al., "Intein Zymogens: Conditional Assembly and Splicing of Split Inteins via Targeted Proteolysis," Journal of the American Chemical Society 2017, 139, 8074-8077.
Gray et al., "Activation of Specific Apoptotic Caspases with an Engineered Small Molecule-Activated Protease," Cell 2010, 142(4), 637-646.
Greber et al., "An engineered mammalian band-pass network," Nucleic Acids Research 2010, 38(18), e174.
Hancock et al., "A Caax or a CAAL motif and a second signal are sufficient for plasma membrane targeting of ras proteins," The EMBO Journal 1991, 10(13), 4033-4039.
Hart et al., "The Utility of Paradoxical Components in Biological Circuits," Molecular Cell 2013, 49, 213-221.
Herrmann et al., "Quantitative Analysis of the Complex between p21ras and the Ras-binding Domain of the Human Raf-1 Protein Kinase," Journal of Biological Chemistry 1995, 270(7), 2901-2905.
Howard et al., "Redirecting tyrosine kinase signaling to an apoptotic caspase pathway through chimeric adaptor proteins," PNAS 2003, 100(20), 11267-11272.
International Search Report and Written Opinion dated Aug. 12, 2019 in PCT Patent Application PCT/US2019/014078.
International Search Report and Written Opinion dated Dec. 19, 2019 in PCT Patent Application PCT/US2019/048914.
Iwamoto et al., "A General Chemical Method to Regulate Protein Stability in the Mammalian Central Nervous System," Chemistry & Biology 2010, 17, 981-988.
Jacobs et al., "StaPLs: versatile genetically encoded modules for engineering drug-inducible proteins," Nature Methods 2018, 15(7), 523-526.
Khalil et al., "A Synthetic Biology Framework for Programming Eukaryotic Transcription Functions," Cell 2012, 150, 647-658.
Kim et al., "Time-gated detection of protein-protein interactions with transcriptional readout," elite 2017, 6, e30233.
Kipniss et al., "Engineering cell sensing and responses using a GPCR-coupled CRISPR-Cassystem," Nature Communications 2017, 8, 2212.
Koch-Nolte et al., "Single domain antibodies from llama effectively and specifically block T cellecto-ADP-ribosyltransferase ART2.2 in vivo," The FASEB Journal 2007, 21, 3490-3498.
Koh et al., "An Internal Ribosome Entry Site (IRES) Mutant Library for Tuning Expression Level of Multiple Genes in Mammalian Cells," PLOS One 2013, 8(12), e82100.
Kojima et al., "Toward a world of theranostic medication: Programming biological sentinel systems for therapeutic intervention," Advanced Drug Delivery Reviews 2016, 105, 66-76.
Lichty et al., "Vesicular stomatitis virus: re-inventing the bullet," TRENDS in Molecular Medicine2004, 10(5), 210-216.
Lienert et al., "Synthetic biology in mammalian cells: Next generation research tools and therapeutics," Nature Reviews of Molecular Cell Biology 2014, 15(2), 95-107.
Lohmueller et al., "A tunable zinc finger-based framework for Boolean logic computation in mammalian cells," Nucleic Acids Research 2012, 40(11), 5180-5187.
Ma et al., "Defining Network Topologies that Can Achieve Biochemical Adaptation," Cell 2009, 138, 760-773.
Marchisio et al., "Computational design of synthetic gene circuits with composable parts," Bioinformatics 2008, 24(17), 1903-1910.
Morsut et al., "Engineering Customized Cell Sensing and Response Behaviors Using Synthetic Notch Receptors," Cell 2016, 164(4), 780-791.
Nakanishi et al., Development of Sendai Virus Vectors and their Potential Applications in Gene Therapy and Regenerative Medicine, Current Gene Therapy 2012, 12, 410-416.
Nallamsetty et al., "Efficient site-specific processing of fusion proteins by tobacco vein mottlingvirus protease in vivo and in vitro," Protein Expression and Purification 2004, 38, 108-115.
Nelson, "Antibody fragments," mAbs 2010, 2(1), 77-83.

(56) References Cited

OTHER PUBLICATIONS

Nielsen et al., "Genetic circuit design automation," Science 2016, 352(6281), aac7341.
Nissim et al., "A tunable dual-promoter integrator for targeting of cancer cells," Molecular Systems Biology 2010, 6(444), 1-9.
Notice of Allowance and Fee(s) dated May 18, 2022 in U.S. Appl. No. 16/555,604.
Oliveira et al., "An Improved Ras Sensor for Highly Sensitive and Quantitative FRET-FLIM Imaging," PLOS One 2013, 8(1), e52874.
Park et al., "Rewiring MAP Kinase Pathways Using Alternative Scaffold Assembly Mechanisms," Science 2003, 299, 1061-1064.
Porcher et al., "The Bicoid Morphogen System," Current Biology 2010, 20(5), R249-R254.
Pu et al., "Evolution of a split RNA polymerase as a versatile biosensor platform," Nature Chemical Biology 2017, 13(4), 432-438.
Reinke et al., "A synthetic coiled-coil interactome provides heterospecific modules for molecular engineering," Journal of the American Chemical Society 2010, 132(17), 6025-6031.
Restriction Requirement dated Dec. 9, 2019 in U.S. Appl. No. 16/250,314.
Riechmann et al., "Single domain antibodies: comparison of camel VH and camelised human VH domains," Journal of Immunological Methods 1999, 231, 25-38.
Rinaudo et al., "A universal RNAi-based logic evaluator that operates in mammalian cells," Nature Biotechnology 2007, 1-6.
Roquet et al., "Synthetic recombinase-based state machines in living cells," Science 2016, 353(6297), aad8559.
Rossi et al., "Monitoring protein-protein interactions in intact eukaryotic cells by b-galactosidase complementation," PNAS 1997, 94, 8405-8410.
Roybal et al., "Precision Tumor Recognition by T Cells With Combinatorial Antigen-SensingCircuits," Cell 2016, 164, 770-779.
Russell et al., "Oncolytic Virotherapy," Nature Biotechnology 2012, 30(7).
Schnell et al., "Infectious rabies viruses from cloned cDNA," The EMBO Journal 1994, 13(18), 4195-4203.
Schwanhausser et al. "Global quantification of mammalian gene expression control" Nature 2011, 473, 337-342.
Snitkovsky et al., "A TVA-Single-Chain Antibody Fusion Protein Mediates Specific Targeting of a Subgroup A Avian Leukosis Virus Vector to Cells Expressing a Tumor-Specific Form of Epidermal Growth Factor Receptor," Journal of Virology 2000, 74(20), 9540-9545.
Stein et al., "Ultrasensitive Scaffold-Dependent Protease Sensors with Large Dynamic Range," ACS Synthetic Biology 2017, 6, 1337-1342.
Stein et al., "Protease-based synthetic sensing and signal amplification," PNAS 2014, 1-6.
Stevens et al., "Design of a Split Intein with Exceptional Protein Splicing Activity," Journal of the American Chemical Society 2016, 138, 2162-2165.
Stricker et al. "A fast, robust and tunable synthetic gene oscillator," Nature 2008, 456, 516-520.
Szymczak et al., "Correction of multi-gene deficiency in vivo using a single 'self-cleaving' 2Apeptide-based retroviral vector," Nature Biotechnology 2004, 22, 589-594.
Tang et al., "Detection and manipulation of live antigen-expressing cells using conditionally stable nanobodies," eLIFE 2016, 5, e15312.
Taremi et al., "Construction, expression, and characterization of a novel fully activated recombinant single-chain hepatitis C virus protease," Protein Science 1998, 7, 2143-2149.
Taxis et al., "Efficient protein depletion by genetically controlled deprotection of a dormant N-degron," Molecular Systems Biology 2009, 5(267), 1-7.
To et al., "Rationally designed fluorogenic protease reporter visualizes spatiotemporal dynamics of apoptosis in vivo," PNAS 2015, 112(11), 3338-3343.
Tozser et al., "Comparison of the substrate specificity of two potyvirus proteases," The FEBS Journal 2005, 272, 514-523.
Truong et al., "Development of an intein-mediated split-Cas9 system for gene therapy," Nucleic Acids Research 2015, 43(13), 6450-6458.
Varshavsky, "The N-end rule: Functions, mysteries, uses," PNAS 1996, 93, 12142-12149.
Waugh, "An overview of enzymatic reagents for the removal of affinity tags," Protein Expression and Purification 2011.
Wehr et al., "Monitoring regulated protein-protein interactions using split TEV," Nature Methods 2006, 3(12), 985-993.
Weinberg et al., "Large-scale design of robust genetic circuits with multiple inputs and outputs for mammalian cells," Nature Biotechnology 2017, 35(5), 453-462.
Weinheimer et al., "Autoproteolysis of Herpes Simplex Virus Type 1 Protease Releases an Active Catalytic Domain Found in Intermediate Capsid Particles," Journal of Virology 1993, 67(10), 5813-5822.
Wikstrand et al., "The class III variant of the epidermal growth factor receptor (EGFRvIII): characterization and utilization as an immunotherapeutic target," Journal of NeuroVirology 1998, 4, 148-158.
Wroblewska et al., "Mammalian synthetic circuits with RNA binding proteins delivered by RNA," Nature Biotechnology 2015, 33(8), 839-841.
Xie et al., "Multi-Input RNAi-Based Logic Circuit for Identification of Specific Cancer Cells," Science 2011, 333, 1307-1311.
Yasuda et al., "Supersensitive Ras activation in dendrites and spines revealed by two-photon fluorescence lifetime imaging," Nature Neuroscience 2006, 9(2), 283-291.
Yeh et al., "Rewiring cellular morphology pathways with synthetic guanine nucleotide exchange factors," Nature 2007, 447, 596-600.
Zetche et al., "A Split Cas9 Architecture for Inducible Genome Editing and Transcription Modulation," Nature Biotechnology 2015, 33(2), 139-142.

SEQUENCE LISTING

```
Sequence total quantity: 4
SEQ ID NO: 1            moltype = AA  length = 2662
FEATURE                 Location/Qualifiers
REGION                  1..2662
                        note = Protease Fusion Protein
source                  1..2662
                        mol_type = protein
                        organism = synthetic construct
SEQUENCE: 1
MSKIFVNPSA IRAGLADLEM AEETVDLINR NIEDNQAHLQ GEPIEVDNLP EDMGRLHLDD    60
GKSPNHGEIA KVGEGKYRED FQMDEGEDPS PLFQSYLENV GVQIVRQMRS GERFLKIWSQ   120
TVEEIISYVA VNFPNPPGKS SEDKSTQTTG RELKKETTPT PSQRESQSSK ARMAAQIASG   180
PPALEWSATN EEDDLSVEAE IAHQIAESFS KKYKFPSRSS GILLYNFEQL KMNLDDIVKE   240
AKNVPGVTRL AHDGSKLPLR CVLGWVALAN SKKFQLLVES DKLSKIMQDD LNRYTSCGGS   300
GLEDVVCCHG SGSGSGSVVL VGRLLLSGSG SAPITAYAQQ TRGLLGCIIT SLTGRDKNQA   360
EGEVQIVSTA AQTFLATCIN GVCWTVYHGA GTRTIASPKG PVIQMYTNVD KDLVGWPAPQ   420
GTRSLTPCAC GSSDLYLVTR HADVIPVRRR GDSRGSLLSP RPISYLKGSS GGPLLCPAGH   480
AVGIFRAAVC TRGVAKAVDF IPVENLETTM RSPVFTDNSS PPAVSGGGGD EMEECSLDPG   540
EVYDDPIDPI ELEAEPRGTP IVPNILRNSD YNLNSPLIED PARLMLEWLK TGNRPYRMTL   600
TDNCSRSFRV LKDYFKKVDL GSLKVGGMAA QSMISLWLYG AHSESNRSRR CITDLAHFYS   660
KSSPIEKLLN LTLGNRGLRI PPEGVLSCLE RVDYDNAFGR YLANTYSSYL FFHVITLYMN   720
ALDWDEEKTI LALWKDLTSV DIGKDLVKFK DQIWGLLIVT KDFVYSQSSN CLFDRNYTLM   780
LKDLFLSRFN SLMVLLSPPE PRYSDDLISQ LCQLYIAGDQ VLSMCGNSGY EVIKILEPYV   840
VNSLVQRAEK FRPLIHSLGD FPVFIKDKVS QLEETFGPCA RRFFRALDQF DNIHDLVFVF   900
GCYRHWGHPY IDYRKGLSKL YDQVHLKKMI DKSYQECLAS DLARRILRWG FDKYSKWYLD   960
SRFLARDHPL TPYIKTQTWP PKHIVDLVGD TWHKLPITQI FEIPESMDPS EILDDKSHSF  1020
TRTRLASWLS ENRGGPVPSE KVIITALSKP PVNPREFLRS IDLGGLPDED LIIGLKPKER  1080
ELKIEGRFFA LMSWNLRLYF VITEKLLANY ILPLFDALTM TDNLNKVFKK LIDRVTGQGL  1140
LDYSRVTYAF HLDYEKWNNH QRLESTEDVF SVLDQVFGLK RVFSRTHEFF QKAWIYYSDR  1200
SDLIGLREDQ IYCLDASNGP TCWNGQDGGL EGLRQKGWSL VSLLMIDRES QIRNTRTKIL  1260
AQGDNQVLCP TYMLSPGLSQ EGLLYELERI SRNALSIYRA VEEGASKLGL IIKKEETMCS  1320
YDFLIYGKTP LFRGNILVPE SKRWARVSCV SNDQIVNLAN IMSTVSTNAL TVAQHSQSLI  1380
KPMRDFLLMS VQAVFHYLLF SPILKGRVYK ILSAEGESFL LAMSRIIYLD PSLGGISGMS  1440
LGRFHIRQFS DPVSEGLSFW REIWLSSQES WIHALCQEAG NPDLGERTLE SFTRLLEDPT  1500
TLNIRGGASP TILLKDAIRK ALYDEVDKVE NSEFREAILL SKTHRDNFIL FLISVEPLFP  1560
RFLSELFSSS FLGIPESIIG LIQNSRTIRR QFRKSLSKTL EESFYNSEIH GISRMTQTPQ  1620
RVGGVWPCSS ERADLLREIS WGRKVVGTTV PHPSEMLGLL PKSSISCTCG ATGGGNPRVS  1680
VSVLPSFDQS FFSRGPLKGY LGSSTSMSTQ LFHAWEKVTN VHVVKRALSL KESINWFITR  1740
DSNLAQALIR NIMSLTGPDF PLEEAPVFKR TGSALHRFKS ARYSEGGYSS VCPNLLSHIS  1800
VSTDTMSDLT QDGKNYDFMF QPLMLYAQTW TSELVQRDTR LRDSTFHWHL RCNRCVRPID  1860
DVTLETSQIF EFPDVSKRIS RMVSGAVPHF QRLPDIRLRP GDFESLSGRE KSHHIGSAQG  1920
LLYSILVAIH DSGYNDGTIF PVNIYGKVSP RDYLRGLARG VLIGSSICFL TRMTNININR  1980
PLELVSGVIS YILLRLDNHP SLYIMLREPS LRGEIFSIPQ KIPAAYPTTM KEGNRSILCY  2040
LQHVLRYERE IITASPENDW LWIFSDFRSA KMTYLSLITY QSHLLLQRVE RNLSKSMRDN  2100
LRQLSSLMRQ VLGGHGEDTL ESDDNIQRLL KDSLRRTRWV DQEVRHAART MTGDYSPNKK  2160
VSRKVGCSEW VCSAQQVAVS TSANPAPVSE LDIRALSKRF QNPLISGLRV VQWATGAHYK  2220
LKPILDDLNV FPSLCLVVGD GSGGISRAVL NMFPPDAKLVF NSLLEVNDLM ASGTHPLPPS  2280
AIMRGGNDIV SRVIDLDSIW EKPSDLRNLA TWKYFQSVQK QVNMSYDLII CDAEVTDIAS  2340
INRITLLMSD FALSIDGPLY LVFKTYGTML VNPNYKAIQH LSRAFPSVTG FITQVTSSFS  2400
SELYLRFSKR GKFFRDAEYL TSSTLREMSL VLFNCSSPKS EMQRARSLNY QDLVRGFPEE  2460
IISNPYNEMI ITLIDSDVES FLVHKMVDDL ELQRGTLSKV AIIIAIMIVF SNRVFNVSKP  2520
LTDPSFYPPS DPKILRHFNI CCSTMMYLST ALGDVPSFAR LHDLYNRPIT YYFRKQVIRG  2580
NVYLSWSWSN DTSVFKRVAC NSSLSLSSHW IRLIYKIVKT TRLVGSIKDL SREVERHLHR  2640
YNRWITLEDI RSRSSLLDYS CL                                          2662

SEQ ID NO: 2            moltype = DNA  length = 7986
FEATURE                 Location/Qualifiers
misc_feature            1..7986
                        note = Protease Fusion Protein
source                  1..7986
                        mol_type = other DNA
                        organism = synthetic construct
SEQUENCE: 2
atgagcaaga tctttgtcaa tcctagtgct attagagccg gtctggccga tcttgagatg    60
gctgaagaaa ctgttgatct gatcaataga aatatcgaag acaatcaggc tcatctccaa   120
gggaaccca tagaggtgga caatctccct gaggatatgg ggcgacttca cctggatgat   180
ggaaaatcgc ccaaccatgg tgagatagcc aaggtgggaa aagcaagta tcgagaggac   240
tttcagatgg atgaaggaga ggatcctagc ttcctgttcc agtcatacct ggaaaatgtt   300
ggagtccaaa tagtcagaca aatgaggtca ggagagagat ttctcaagat atggtcacag   360
accgtagaag agattatatc ctatgtcgcg gtcaactttc caacccctcc aggaaagtct   420
```

```
tcagaggata aatcaaccca gactactggc cgagagctca agaaggagac aacacccact    480
ccttctcaga gagaaagcca atcatcgaaa gccaggatgg cggctcaaat tgcttctggc    540
cctccagccc ttgaatggtc ggctaccaat aagaggatg atctatcagt ggaggctgag     600
atcgctcacc agattgcaga aagtttctcc aaaaaatata agtttccctc tcgatcctca    660
gggatactct tgtataattt tgagcaattg aaaatgaacc ttgatgatat agttaaagag    720
gcaaaaaatg taccaggtgt gacccgttta gcccatgacg ggtccaaact cccctaaga    780
tgtgtactgg gatgggtcgc tttggccaac tctaagaaat tccagttgtt agtcgaatcc    840
gacaagctga gtaaaatcat gcaagatgac ttgaatcgct atacatcttg cggtgggtcc    900
ggtctcgagg atgttgtttg ttgccacggg agcggatcgg gatccggctc tgtggtgctt    960
gtagggcgat tgctgctctc tggttctggg tccgcccaa taacggccta cgcccaacag    1020
acacgcggtc tgctggggtg cattattacc tcacttacgg gcagagacaa aaaccaggct    1080
gagggagaag ttcagattgt ttcaacggcg gctcagacct tcttgccac ctgtataaac     1140
ggagtatgct ggacagtcta ccatggtgca gggaccccga caatagcgag tcccaaaggg    1200
cccgtcatac agatgtatac taacgtcgat aaggacctcg tgggttggcc cgctcctcaa    1260
ggcacgcgat ccctcacacc ttgtgcgtgc ggcagttcag acctctatct ggtgactcgc    1320
catgccgacg taatccctgt tcgccggagg ggtgatagta gagggagctt gctcagtcct    1380
aggccgattt cctatctcaa gggctcaagc ggcggcccat tgctctgccc ggccggccac    1440
gcggtaggaa ttttccgggc cgcagtttgc acacgcgggtc tcgcaaaagc agtagacttt    1500
ataccagtag agaaccttga aacaacgatg aggtccctg tatttacaga taacagttcc      1560
cctccggctg tcagtggagg tggaggcgac gagatgagg agtgttcgct cgatcctgga     1620
gaggtctatg atgaccctat tgacccaatc gagttagagg ctgaaccag aggaaccccc     1680
attgtcccca acatcttgag gaactctgac tacaatctca actctccttt gatagaagat    1740
cctgctagac taatgttaga atggttaaaa acagggaata gacctttatcg gatgactcta   1800
acagacaatt gctccaggtc tttcagagtt ttgaaagatt atttcaagaa ggtagatttg    1860
ggttctctca aggtgggcgg aatggctgca cagtcaatga tttctctctg gttatatggt    1920
gcccactctg aatccaacag gagccggaga tgtataacag acttggccca tttctattcc    1980
aagtcgtccc ccatagagaa gctgttgaat ctcacgctag gaaatagagg gctgagaatc    2040
cccccagagg gagtgttaag ttgccttgag agggttgatt atgataatgc atttggaagg    2100
tatcttgcca cacgtattc ctcttacttg ttccttccatg taatcacctt atacatgaac    2160
gccctagact ggggatgaaga aaagaccatc ctagcattat ggaaagattt aacctcagtg    2220
gacatcggga aggacttggt aaagttcaaa gaccaaatat ggggactgct gatcgtgaca    2280
aaggactttg tttactccca aagttccaat tgtcttttg acagaaacta cacacttatg     2340
ctaaaagatc ttttctctgtc tcgcttcaac tccttaatgg tcttgctctc tcccccagag   2400
ccccgatact cagatgactt gatatctcaa ctatgccagc tgtacattgc tggggatcaa    2460
gtcttgtcta tgtgtggaaa ctccggctat gaagtcatca aaatattggc gccatatgtc    2520
gtgaatagtt tagtccagag agcagaaaag tttaggcctc tcattcattc cttgggagac    2580
tttcctgtat ttataaaaga caaggtaagt caacttgaag agacgttcgg tccctgtgca    2640
agaaggttct ttagggctct ggatcaattc gacaacatac atgacttggt ttttgtgttt    2700
ggctgttaca ggcattgggg gcacccatat atagattatc gaaagggtct gtcaaaacta    2760
tatgatcagg ttcaccttaa aaaatgata gataagtcct accaggagtg cttagcaagc    2820
gacctagcca ggaggatcct tagatggggt tttgataagt actccaagtg gtatctggat   2880
tcaagattcc tagcccgaga ccacccctg actcctata tcaaaaccca aacatggcca      2940
cccaaaacata ttgtagactt ggtggggat acatggcaca agctcccgat cacgcagatc    3000
tttgagattc ctgaatcaat ggatccgtca gaaatattgg atgacaaatc acattctttc    3060
accagaacga gactagcttc ttggctgtca gaaaaccgag gggggcctgt tcctagcgaa    3120
aaagttatta tcacgcccct gtctaagccg cctgtcaatc cccgagagtt tctgaggtct    3180
atagacctcg gaggattgcc agatgaagac ttgataattg gcctcaagcc aaaggaacgg    3240
gaattgaaga ttgaaggtcg attctttgct ctaatgtcat ggaatctaag attgtatttt    3300
gtcatcactg aaaaactctt ggccaactac atcttgccac ttttgacgc gctgactatg    3360
acagacaacc tgaacaaggt gttaaaaag ctgatcgaca gggtcaccgg gcaagggctt     3420
ttggactatt caagggtcac atatgcattt cacctggact atgaaaagtg gaacaaccat    3480
caaagattag agtcaacaga ggatgtattt tctgtcctag atcaagtgtt tggattgaag   3540
agagtgtttt ctagaacaca cgagtttttt caaaaggcct ggatctatta ttcgacagag   3600
tcagacctca tcgggttacg ggaggatcaa atatactgct tagatgcgtc caacggccca   3660
acctgttgga atggccagga tggcgggcta gaaggcttac ggcagaaggg ctggagtcta   3720
gtcagcttat tgatgataga tagaaatctc caaatcagga acacaagaac caaaatacta   3780
gctcaaggag acaaccaggt tttatgtccg acatacatgt tgtcgccagg ctatctcaa    3840
gaggggctcc tctatgaatt ggagagaata tcaaggaatg cactttcgat atacagagcc   3900
gtcgaggaag gggcatctaa gctagggctg atcatcaaga aagaggagac catgtgtagt   3960
tatgacttcc tcatctatgg aaaaaccccct ttgtttagag gtaacatatt ggtgcctgag  4020
tccaaaagat gggccagagt ctcttgcgtc tctaatgacc aaatagtcaa cctcgccaat  4080
ataatgtcga cagtgtccac caatgcgcta acagtggcac aacactctca atctttgatc   4140
aaaccgatga gggattttct gctcatgtca gtacaggcag tctttcacta cctgctatttt  4200
agcccaatct taaagggaag agtttacaag attctgacgga ctgaagggga gagctttctc  4260
ctagccatgt caaggataat ctatctagat ccttctttgg gagggatatc tggaatgtcc   4320
ctcggaagat tccatatacg acagttctca gaccctgtct ctgaagggtt atccttctgg   4380
agagagatct ggttaagctc ccaagagtcc tggattcacg cgttgtgtca agaggctgga   4440
aacccagatc ttgagagag aacactcgag agcttcactc gccttctaga agatccgaat    4500
accttaaaata tcagaggagg ggccagtcct accattctac tcaaggatgc aatcagaaag   4560
gctttatatg acgaggtgga caaggtgaaa aattcagagt ttcgagaggc aatcctgttg    4620
tccaagaccc atagagataa ttttatactc ttcttaatat ctgttgagcc tctgtttcct    4680
cgatttctca gtgagctatt cagttcgtct ttttgggaa tccccgagtc aatcattgga    4740
ttgatacaaa actcccgaac gataagaagg cagtttagaa agagtctctc aaaaactta   4800
gaagaatcct tctacaactc agatctccac ggattagtc ggatgaccca gacacctcag     4860
agggttgggg ggtgtggcc ttgctcttca gagagggcag atctacttag ggagatctct    4920
tgggaagaa aagtggtagg cacgacagtt cctcacccctt ctgagatgtt gggattactt   4980
cccaagtcct ctatttcttg cacttgtgga gcaacaggag gaggcaatcc tagagtttct    5040
gtatcagtac tcccgtcctt tgatcagtca ttttttttcac gaggccccct aaagggatac   5100
ttgggctcgt ccacctctat gtcgacccag ctattccatg catgggaaaa agtcactaat    5160
```

```
gttcatgtgg tgaagagagc tctatcgtta aaagaatcta taaactggtt cattactaga    5220
gattccaact tggctcaagc tctaattagg aacattatgt ctctgacagg ccctgatttc    5280
cctctagagg aggcccctgt cttcaaaagg acggggtcag ccttgcatag gttcaagtct    5340
gccagataca gcgaaggagg gtattcttct gtctgcccga acctcctctc tcatatttct    5400
gttagtacag acaccatgtc tgatttgacc caagacgtga agaactacag tttcatgttc    5460
cagccattga tgctttatgc acagacatgg acatcagagc tggtacagag agacacaagg    5520
ctaagagact ctacgtttca ttggcacctc cgatgcaaca ggtgtgtgag acccattgac    5580
gacgtgaccc tggagacctc tcagatcttc gagtttccgg atgtgtcgaa aagaatatcc    5640
agaatggttt ctggggctgt gcctcacttc cagaggcttc ccgatatccg tctgagacca    5700
ggagatttg aatctctaag cggtagagaa aagtctcacc atatcggatc agctcagggg    5760
ctcttatact caatcttagt ggcaattcac gactcaggat acaatgatgg aaccatcttc    5820
cctgtcaaca tatacggcaa ggtttcccct agagactatt tgagagggct cgcaagggga    5880
gtattgatag gatcctcgat tgcttcttg acaagaatga caaatatcaa tattaataga    5940
cctcttgaat tggtctcagg ggtaatctca tatattctcc tgaggctaga taaccatccc    6000
tccttgtaca taatgctcag agaaccgtct cttagaggag agatattttc tatccctcag    6060
aaaatccccg ccgcttatcc aaccactatg aagaaggca acagatcaat cttgtgttat    6120
ctccaacatg tgctacgcta tgagcagag ataatcacgg cgtctccaga gaatgactgg    6180
ctatggatct tttcagactt tagaagtgcc aaaatgacgt acctatccct cattacttac    6240
cagtctcatc ttctactcca gagggttgag agaaacctat ctaagagtat gagagataac    6300
ctgcgacaat tgagttcttt tgatgaggcag gtgctgggcg ggcacggaga gataccttta    6360
gagtcagacg acaacattca acgactgcta aaagactctt tacgaaggac aagatgggtg    6420
gatcaagagg tgcgccatgc agctagaacc atgactggga attacagccc caacaagaag    6480
gtgtcccgta aggtaggatg ttcagaatgg gtctgctctg ctcaacaggt tgcagtctct    6540
acctcagcaa accggcccc tgtctcgag cttgacataa gggccctctc taagaggttc    6600
cagaacccct tgatctcggg cttgagagtg ttcagtggg caaccggtgc tcattataag    6660
cttaagccta ttctagatga tctcaatgtt ttcccatctc tcgccttgt agttgggggac    6720
gggtcagggg ggatatcaag ggcagtcctc aacatgtttc cagatgccaa gcttgtgttc    6780
aacagtcttt tagaggtgaa tgacctgatg gcttccggaa cacatccact gcctccttca    6840
gcaatcatga ggggaggaaa tgatatcgtc tccagagtga tagatcttga ctcaatctgg    6900
gaaaaaccgt ccgacttgag aaacttggca acctggaaat acttccagtc agtccaaaag    6960
caggtcaaca tgtcctatga cctcattatt tgcgatgcag aagttactga cattgcatct    7020
atcaaccgga tcaccctgtt aatgtccgat tttgcattgt ctatagatgg accactctat    7080
ttggtcttca aaacttatgg gactatgcta gtaaatccaa actacaaggc tattcaacac    7140
ctgtcaagag cgttcccctc ggtcacaggg tttatcaccc aagtaacttc gtcttttttca    7200
tctgagctct acctccgatt ctccaaacga gggaagtttt tcagagatgc tgagtacttg    7260
acctcttcca ccccttcgaga aatgagcctt gtgttattca attgtagcag ccccaagagt    7320
gagatgcaga gagctcgttc cttgaactat caggatcttg tgagaggatt tcctgaagaa    7380
atcatatcaa atccttacaa tgagatgatc ataactctga ttgacagtga tgtagaatct    7440
tttctagtcc acaagatggt tgatgatctt gagttacaga ggggaactct gtctaaagtg    7500
gctatcatta tagccatcat gatagttttc tccaacagag tcttcaacgt ttccaaaccc    7560
ctaactgacc cctcgttcta tccaccgtct gatcccaaaa tcctgaggca cttcaacata    7620
tgttgcagta ctatgatgta tctatctact gctttaggtg acgtccctag cttcgcaaga    7680
cttcacgcc tgtataacag acctataact tattacttca gaaagcaagt cattcgagtg    7740
aacgtttatc tatcttggag ttggtccaac gacacctcag tgttcaaaag ggtagcctgt    7800
aattctagcc tgagtctgtc atctcactgg atcaggttga tttacaagat agtgaagact    7860
accagactcg ttggcagcat caaggatcta tccagagaag tggaaagaca ccttcatagg    7920
tacaacaggt ggatcaccct agaggatatc agatctagat catccctact agactacagt    7980
tgcctg                                                              7986

SEQ ID NO: 3          moltype = AA   length = 430
FEATURE               Location/Qualifiers
REGION                1..430
                      note = Degron Fusion Protein
source                1..430
                      mol_type = protein
                      organism = synthetic construct
SEQUENCE: 3
MSKIFVNPSA IRAGLADLEM AEETVDLINR NIEDNQAHLQ GEPIEVDNLP EDMGRLHLDD      60
GKSPNHGEIA KVGEGKYRED FQMDEGEDPS FLFQSYLENV GVQIVRQMRS GERFLKIWSQ     120
TVEEIISYVA VNFPNPPGKS SEDKSTQTTG RELKKETTPT PSQRESQSSK ARMAAQIASG     180
PPALEWSATN EEDDLSVEAE IAHQIAESFS KKYKFPSRSS GILLYNFEQL KMNLDDIVKE     240
AKNVPGVTRL AHDGSKLPLR CVLGWVALAN SKKFQLLVES DKLSKIMQDD LNRYTSCGGS     300
GLENLYFQSG SGSMADVQLV ESGGALVQPG GSLRLSCVAS GFPVNRYSMR WYRQAPGKER     360
EWVAGMSSAG DRSSYVDSVK GRFTIRRDDA RNTVYLQMNS LKPEDTAVYY YNVNVGFEYW     420
GHGTQVTVSF                                                           430

SEQ ID NO: 4          moltype = DNA   length = 1290
FEATURE               Location/Qualifiers
misc_feature          1..1290
                      note = Degron Fusion Protein
source                1..1290
                      mol_type = other DNA
                      organism = synthetic construct
SEQUENCE: 4
atgagcaaga tctttgtcaa tcctagtgct attagagccg gtctggccga tcttgagatg      60
gctgaagaaa ctgttgatct gatcaataga aatatcgaag acaatcaggc tcatctccaa     120
ggggaaccca tagaggtgga caatctccct gaggatatgg gcgacttca cctggatgat     180
ggaaaatcgc ccaaccatgg tgagatagcc aaggtggag aaggcaagta cgagaggac     240
ttcagatgg atgaaggaga ggatcctagc ttcctgttcc agtcatacct ggaaaatgtt     300
```

-continued

```
ggagtccaaa tagtcagaca aatgaggtca ggagagagat ttctcaagat atggtcacag    360
accgtagaag agattatatc ctatgtcgcg gtcaactttc ccaaccctcc aggaaagtct    420
tcagaggata aatcaaccca gactactggc cgagagctca agaaggagac aacacccact    480
ccttctcaga gagaaagcca atcatcgaaa gccaggatgg cggctcaaat tgcttctggc    540
cctccagccc ttgaatggtc ggctaccaat gaagaggatg atctatcagt ggaggctgag    600
atcgctcacc agattgcaga aagtttctcc aaaaaatata agtttccctc tcgatcctca    660
gggatactct tgtataattt tgagcaattg aaaatgaacc ttgatgatat agttaaagag    720
gcaaaaaatg taccaggtgt gacccgttta gcccatgacg ggtccaaact cccctaaga    780
tgtgtactgg gatgggtcgc tttggccaac tctaagaaat tccagttgtt agtcgaatcc    840
gacaagctga gtaaaatcat gcaagatgac ttgaatcgct atacatcttg cggtgggtcc    900
ggtctcgaga acttgtactt ccagagtggg agcggatcga tggccgacgt gcagctcgtg    960
gaatccggag gagcactggt ccagcctggg ggatcactga gactgtcttg tgtcgcttct   1020
ggctttcctg tgaatcggta ctctatgaga tggtacaggc aggcacctgg aaaagagcga   1080
gaatgggtcg ccggaatgtc atctgctggc gataggagtt cctacgtgga tagcgtgaaa   1140
ggacggttca ccattcgtag ggacgatgct agaaacaccg tgtacctcca gatgaactcc   1200
ctgaaacctg aggacactgc tgtgtactac tataacgtca atgtgggctt tgaatactgg   1260
ggacacggca cacaagtgac tgttagtttt                                    1290
```

RNA-BASED DELIVERY SYSTEMS WITH LEVELS OF CONTROL

RELATED APPLICATIONS

This application is a continuation application of U.S. application Ser. No. 16/555,604, filed Aug. 29, 2019, which claims the benefit under 35 U.S.C. § 119(e) of U.S. Provisional Application No. 62/725,020, filed Aug. 30, 2018; and U.S. Provisional Application No. 62/777,420, filed Dec. 10, 2018. The contents of these applications are hereby expressly incorporated by reference in their entireties.

STATEMENT REGARDING FEDERALLY SPONSORED R&D

This invention was made with government support under Grant No. GM007616 awarded by the National Institutes of Health. The government has certain rights in the invention.

REFERENCE TO SEQUENCE LISTING

The present application is being filed along with a Sequence Listing in electronic format. The Sequence Listing is provided as a file entitled Sequence_Listing_30KJ-300661-US, created Sep. 23, 2022, which is 18 kilobytes in size. The information in the electronic format of the Sequence Listing is incorporated herein by reference in its entirety.

BACKGROUND

Field

The present disclosure relates generally to the field of polynucleotide delivery.

Description of the Related Art

DNA-based vectors for delivery of polynucleotides into patient cells suffer from various disadvantages. Some of these vectors (e.g., lentivirus) insert into the host genome and, while others (e.g., adeno-associated virus), though non-inserting by nature or by design, are still not entirely free of mutagenic insertion, due to the presence of exogenous DNA in close proximity to genomic DNA. Such insertions are unpredictable and irreversible, and could be oncogenic even if their frequencies are very low. While an DNA-free vector would alleviate these concerns, a key obstacle to such systems is relative lack of regulation methods. A further problem in the art is that a virus vector may persist and cause adverse effects, such as an immune reaction against viral components or delayed effects of viral infection. Moreover, the prolonged expression of foreign genes may also result in an autoimmune-like reaction to self-antigens or interfere with cellular processes like signaling pathways. There is a need for DNA-free delivery vectors engineered to respond to multiple levels of control.

SUMMARY

Disclosed herein include viral vectors. In some embodiments, the viral vector comprises: a polynucleotide encoding a nucleoprotein (N), a phosphoprotein (P), a matrix protein (M), an RNA-dependent RNA polymerase (L), and one or more transgenes, wherein at least one of the N, P, M, or L is a conditionally stable fusion protein comprising a stabilizing molecule binding domain capable of binding a stabilizing molecule, and wherein the conditionally stable fusion protein changes from a destabilized state to a stabilized state when the stabilizing molecule binding domain binds to the stabilizing molecule, and/or wherein two of the N, P, M, or L are expressed as a protease fusion protein comprising a first protein and a second protein of the two of the N, P, M, or L separated from a protease by a first cut site and a second cut site, respectively, wherein the protease is capable of cutting the first cut site and the second cut site when the protease is not bound by a protease inhibitor, and wherein the first protein and the second protein are in inactive states when the first cut site and the second cut site are not cut, respectively; and an envelope comprising a glycoprotein not encoded by the polynucleotide, wherein the glycoprotein is of the species of any of the N, P, M, and L encoded by the polynucleotide, and/or wherein the glycoprotein, or a portion thereof, is derived of another species, and wherein a glycoprotein binding domain of a first bridge protein is capable of binding the glycoprotein.

Disclosed herein include viral vectors. In some embodiments, the viral vector comprises: a polynucleotide encoding a nucleoprotein (N), a phosphoprotein (P), a matrix protein (M), an RNA-dependent RNA polymerase (L), and one or more transgenes; and an envelope comprising a glycoprotein not encoded by the polynucleotide. In some embodiments, the glycoprotein is of the species of the polynucleotide. In some embodiments, the glycoprotein, or a portion thereof, is derived of another species than the polynucleotide.

Disclosed herein include viral vectors. In some embodiments, the viral vector comprises: a polynucleotide encoding a nucleoprotein (N), a phosphoprotein (P), a matrix protein (M), an RNA-dependent RNA polymerase (L), and one or more transgenes, and wherein the polynucleotide does not encode a glycoprotein; and a glycoprotein, wherein the glycoprotein, or a portion thereof, is derived of another species than the polynucleotide. In some embodiments, wherein a glycoprotein binding domain of a first bridge protein is capable of binding the glycoprotein, wherein a first antigen-binding moiety of the first bridge protein is capable of binding a first antigen on a surface of a target cell, and wherein the viral vector is capable of transducing the target cell when the first antigen-binding moiety is bound to the first antigen and the glycoprotein binding domain is bound to the glycoprotein and a receptor on the cell surface of the target cell. In some embodiments, the glycoprotein comprises EnvA, EnvB, EnvC, EnvD, EnvE, EnvJ, or a portion thereof.

Disclosed herein include viral vectors. In some embodiments, the viral vector comprises a polynucleotide encoding: a nucleoprotein (N), a phosphoprotein (P), a matrix protein (M), an RNA-dependent RNA polymerase (L), and one or more transgenes, wherein at least one of the N, P, M, or L is a conditionally stable fusion protein comprising a stabilizing molecule binding domain capable of binding a stabilizing molecule, and wherein the conditionally stable fusion protein changes from a destabilized state to a stabilized state when the stabilizing molecule binding domain binds to the stabilizing molecule. In some embodiments, P is a conditionally stable fusion protein. In some embodiments, the stabilizing molecule binding domain comprises a nanobody, Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof. In some embodiments, the stabilizing molecule binding domain comprises an RNA aptamer, adNectin, iMab, anticalin, microbody, peptide aptamer, designed ankyrin repeat protein (DARPin), affilin, tetranectin, avimer, affibody, Kunitz domain, or any combination thereof. In some embodiments, the stabilizing molecule is an endogenous molecule of a target cell. In some embodiments, the stabilizing molecule is a molecule specific to a cell type. In some embodiments, the stabilizing molecule is a molecule specific to a disease or disorder. In some embodiments, the stabilizing molecule is an exogenous molecule of a target cell. In some embodiments, the stabilizing molecule is a synthetic protein circuit component. In some embodiments, the polynucleotide is capable of being replicated when the conditionally stable fusion protein is present. In some embodiments, the polynucleotide is capable of being replicated only when the conditionally stable fusion protein is present. In some embodiments, the polynucleotide is capable of being replicated when the conditionally stable fusion protein is in the stabilized state. In some embodiments, the polynucleotide is not capable of being replicated when the conditionally stable fusion protein is in the destabilized state. In some embodiments, the polynucleotide is not capable of being replicated when the stabilizing molecule is absent. In some embodiments, the polynucleotide is capable of being replicated at a threshold concentration of the stabilizing molecule. In some embodiments, the polynucleotide is not capable of being replicated when the stabilizing molecule is present. In some embodiments, the polynucleotide is capable of being replicated at below a threshold concentration of the stabilizing molecule. In some embodiments, two of the N, P, M, or L are expressed as a protease fusion protein comprising a first protein and a second protein of the two of the N, P, M, or L separated from a protease by a first cut site and a second cut site, respectively, wherein the protease is capable of cutting the first cut site and the second cut site when the protease is not bound by a protease inhibitor, and wherein the first protein and the second protein are in inactive states when the first cut site and the second cut site are not cut, respectively.

Disclosed herein include viral vectors. In some embodiments, the viral vector comprises a polynucleotide encoding: a nucleoprotein (N), a phosphoprotein (P), a matrix protein (M), an RNA-dependent RNA polymerase (L), and one or more transgenes, wherein two of the N, P, M, or L are expressed as a protease fusion protein comprising a first protein and a second protein of the two of the N, P, M, or L separated from a protease by a first cut site and a second cut site, respectively, wherein the protease is capable of cutting the first cut site and the second cut site when the protease is not bound by a protease inhibitor, and wherein the first protein and the second protein are in inactive states when the first cut site and the second cut site are not cut, respectively. In some embodiments, the protease is in an active state when the first cut site and the second cut site are not cut. In some embodiments, the protease fusion protein comprises the protease, the first cut site, the second cut site, P, and L. In some embodiments, the 5'-to-3' orientation of the protease fusion protein is 5'-P-the first cut site-protease-the second cut site-L-3'. In some embodiments, P and/or L are in inactive states when the first cut site and/or the second cut site are not cut. In some embodiments, the protease comprises a hepatitis C virus (HCV) protease. In some embodiments, the protease inhibitor comprises asunaprevir, simeprevir, telaprevir, sovaprevir, danoprevir, ciluprevir, boceprevir, paritaprevir, or any combination thereof. In some embodiments, the polynucleotide is capable of being replicated when the first protein and the second protein are in active states. In some embodiments, the first protein and the second protein are in active states when the protease inhibitor is absent. In some embodiments, the polynucleotide is capable of being replicated when the protease inhibitor is absent. In some embodiments, the polynucleotide is not capable of being replicated when the first protein and the second protein are in inactive states. In some embodiments, the first protein and the second protein are in inactive states when the protease inhibitor is present. In some embodiments, the polynucleotide is not capable of being replicated when the protease inhibitor is present. In some embodiments, the first protein and the second protein are in inactive states at a threshold concentration of the protease inhibitor. In some embodiments, the polynucleotide is not capable of being replicated at a threshold concentration of the protease inhibitor. In some embodiments, at least one of the N, P, M, or L is a degron fusion protein comprising a degron capable of binding a degron stabilizing molecule, and wherein the degron fusion protein changes from a destabilized state to a stabilized state when the degron binds to the degron stabilizing molecule.

Disclosed herein include viral vectors. In some embodiments, the viral vector comprises a polynucleotide encoding: a nucleoprotein (N), a phosphoprotein (P), a matrix protein (M), an RNA-dependent RNA polymerase (L), and one or more transgenes, wherein at least one of the N, P, M, or L is a degron fusion protein comprising a degron capable of binding a degron stabilizing molecule, and wherein the degron fusion protein changes from a destabilized state to a stabilized state when the degron binds to the degron stabilizing molecule. In some embodiments, P is a degron fusion protein. In some embodiments, the degron stabilizing molecule is an endogenous molecule of a target cell. In some embodiments, the degron stabilizing molecule is a molecule specific to a cell type. In some embodiments, the degron stabilizing molecule is a molecule specific to a disease or disorder. In some embodiments, the degron stabilizing molecule is an exogenous molecule of a target cell. In some embodiments, the degron stabilizing molecule comprises trimethoprim (TMP). In some embodiments, the degron stabilizing molecule is a synthetic protein circuit component. In some embodiments, the degron comprises a dihydrofolate reductase (DHFR) degron. In some embodiments, the polynucleotide is capable of being replicated when the degron fusion protein is in the stabilized state. In some embodiments, the polynucleotide is not capable of being replicated when the degron fusion protein is in the destabilized state. In some embodiments, the polynucleotide is not capable of being replicated when the degron stabilizing molecule is absent. In some embodiments, the polynucleotide is capable of being replicated at a threshold concentration of the degron stabilizing molecule.

In some embodiments, the polynucleotide does not encode a glycoprotein. In some embodiments, the one or more transgenes comprises a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof. In some embodiments, the one or more transgenes comprises cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof. In some embodiments, the one or more transgenes comprises a synthetic protein circuit component. In some embodiments, the viral vector is an RNA viral vector. In some embodiments, the polynucleotide is derived from a single-stranded RNA virus. In some embodiments, the polynucleotide is derived from a positive sense RNA virus, a negative sense RNA virus, an ambisense RNA virus, or any combination thereof. In some embodiments, the polynucleotide is derived from a negative-strand RNA virus. In some embodiments, the polynucleotide is derived from one or more negative-strand RNA viruses of the order Mononegavirales. In some embodiments, the nucleoprotein (N), phosphoprotein (P), matrix protein (M), and/or RNA-dependent RNA polymerase (L) are derived from one or more negative-strand RNA viruses of the order Mononegavirales. In some embodiments, the one or more negative-strand RNA viruses of the order Mononegavirales comprise a bornaviridae virus, a filoviridae virus, a nyamiviridae virus, a paramyxodiridae virus, a rhabdoviridae virus, or any combination thereof. In some embodiments, the one or more negative-strand RNA viruses of the order Mononegavirales comprise rabies virus, sendai virus, vesicular stomatitis virus, or any combination thereof. In some embodiments, the one or more negative-strand RNA viruses of the order Mononegavirales comprise one or more attenuating mutations. In some embodiments, the one or more negative-strand RNA viruses of the order Mononegavirales comprise an attenuated rabies virus strain. In some embodiments, the attenuated rabies virus strain comprises CVS-N2c, CVS-B2c, DRV-4, RRV-27, SRV-16, ERA, CVS-11, SAD B19, SPBN, SN-10, SN10-333, PM, LEP, SAD, or any combination thereof. In some embodiments, the polynucleotide is evolutionarily stable for at least 100 days of serial passaging. In some embodiments, after 50 days of serial passaging (a) the polynucleotide is not capable of being replicated when the stabilizing molecule is absent, (b) the polynucleotide is not capable of being replicated when the protease inhibitor is present, and/or (c) the polynucleotide is not capable of being replicated when the degron stabilizing molecule is absent. In some embodiments, after 300 days of serial passaging (a) the polynucleotide is not capable of being replicated when the stabilizing molecule is absent, (b) the polynucleotide is not capable of being replicated when the protease inhibitor is present and/or (c) the polynucleotide is not capable of being replicated when the degron stabilizing molecule is absent.

Disclosed herein include systems for delivering a polynucleotide to a target cell of a subject in need thereof. In some embodiments, the system comprises: a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; and a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein.

Disclosed herein include systems for delivering a polynucleotide to a target cell of a subject in need thereof. In some embodiments, the system comprises: a sender cell capable of releasing a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; and a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein.

Disclosed herein include systems for delivering a polynucleotide to a target cell of a subject in need thereof. In some embodiments, the system comprises: a sender cell capable of releasing: (1) a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; and (2) a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein.

In some embodiments, the polynucleotide does not encode the glycoprotein. In some embodiments, the glycoprotein, or a portion thereof, is derived of another species than the polynucleotide. In some embodiments, the glycoprotein comprises EnvA, EnvB, EnvC, EnvD, EnvE, EnvJ, or a portion thereof. In some embodiments, at least one of the N, P, M, or L is a conditionally stable fusion protein comprising a stabilizing molecule binding domain capable of binding a stabilizing molecule, and wherein the conditionally stable fusion protein changes from a destabilized state to a stabilized state when the stabilizing molecule binding domain binds to the stabilizing molecule. In some embodiments, P is a conditionally stable fusion protein. In some embodiments, the stabilizing molecule binding domain comprises a nanobody, Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof. In some embodiments, the stabilizing molecule binding domain comprises an RNA aptamer, adNectin, iMab, anticalin, microbody, peptide aptamer, designed ankyrin repeat protein (DARPin), affilin, tetranectin, avimer, affibody, Kunitz domain, or any combination thereof. The stabilizing molecule, for example, can be an endogenous molecule of a target cell, a molecule specific to a cell type, a molecule specific to a disease or disorder, an exogenous molecule of a target cell, a synthetic protein circuit component, or any combination thereof. In some embodiments, the polynucleotide is capable of being replicated when the conditionally stable fusion protein is present, and/or the polynucleotide is capable of being replicated when the conditionally stable fusion protein is in the stabilized state. In some embodiments, the polynucleotide is not capable of being replicated when the conditionally stable fusion protein is in the destabilized state. In some embodiments, the polynucleotide is not capable of being replicated when the stabilizing molecule is absent. In some embodiments, the polynucleotide is capable of being replicated at a threshold concentration of the stabilizing molecule. In some embodiments, the polynucleotide is not capable of being replicated when the stabilizing molecule is present. In some embodiments, the polynucleotide is capable of being replicated at below a threshold concentration of the stabilizing molecule.

In some embodiments, two of the N, P, M, or L are expressed as a protease fusion protein comprising a first protein and a second protein of the two of the N, P, M, or L separated from a protease by a first cut site and a second cut site, respectively, wherein the protease is capable of cutting the first cut site and the second cut site when the protease is not bound by a protease inhibitor, and wherein the first protein and the second protein are in inactive states when the first cut site and the second cut site are not cut, respectively. In some embodiments, the protease is in an active state when the first cut site and the second cut site are not cut. In some embodiments, the protease fusion protein comprises the protease, the first cut site, the second cut site, P, and L. In some embodiments, the 5'-to-3' orientation of the protease fusion is 5'-P-the first cut site-protease-the second cut site-L-3'. In some embodiments, P and/or L are in inactive states when the first cut site and/or the second cut site are not cut. In some embodiments, the protease comprises a hepatitis C virus (HCV) protease. In some embodiments, the protease inhibitor comprises asunaprevir, simeprevir, telaprevir, sovaprevir, danoprevir, ciluprevir, boceprevir, paritaprevir, or any combination thereof. In some embodiments, the polynucleotide is capable of being replicated when the first protein and the second protein are in active states. In some embodiments, the first protein and the second protein are in active states when the protease inhibitor is absent. In some embodiments, the polynucleotide is capable of being replicated when the protease inhibitor is absent. In some embodiments, the polynucleotide is not capable of being replicated when the first protein and the second protein are in inactive states. In some embodiments, the first protein and the second protein are in inactive states when the protease inhibitor is present. In some embodiments, the polynucleotide is not capable of being replicated when the protease inhibitor is present. In some embodiments, the first protein and the second protein are in inactive states at a threshold concentration of the protease inhibitor. In some embodiments, the polynucleotide is not capable of being replicated at a threshold concentration of the protease inhibitor.

In some embodiments, at least one of the N, P, M, or L is a degron fusion protein comprising a degron capable of binding a degron stabilizing molecule, and wherein the degron fusion protein changes from a destabilized state to a stabilized state when the degron binds to the degron stabilizing molecule. In some embodiments, P is a degron fusion protein. The degron stabilizing molecule can be, for example, an endogenous molecule of a target cell, a molecule specific to a cell type, a molecule specific to a disease or disorder, an exogenous molecule of a target cell, a synthetic protein circuit component, or a combination thereof. In some embodiments, the degron stabilizing molecule comprises trimethoprim (TMP) or a dihydrofolate reductase (DHFR) degron. In some embodiments, the polynucleotide is capable of being replicated when the degron fusion protein is in the stabilized state. In some embodiments, the polynucleotide is not capable of being replicated when the degron fusion protein is in the destabilized state. In some embodiments, the polynucleotide is not capable of being replicated when the degron stabilizing molecule is absent. In some embodiments, the polynucleotide is capable of being replicated at a threshold concentration of the stabilizing molecule. In some embodiments, the polynucleotide does not encode a glycoprotein. In some embodiments, the one or more transgenes comprises a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof. In some embodiments, the one or more transgenes comprises cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof. In some embodiments, the one or more transgenes comprises a synthetic protein circuit component.

In some embodiments, the viral vector is an RNA viral vector. In some embodiments, the polynucleotide is derived from a single-stranded RNA virus. In some embodiments, the polynucleotide is derived from a positive sense RNA virus, a negative sense RNA virus, an ambisense RNA virus, or any combination thereof. In some embodiments, the polynucleotide is derived from a negative-strand RNA virus. In some embodiments, the polynucleotide is derived from one or more negative-strand RNA viruses of the order Mononegavirales. In some embodiments, the nucleoprotein (N), phosphoprotein (P), matrix protein (M), and/or RNA-dependent RNA polymerase (L) are derived from one or more negative-strand RNA viruses of the order Mononegavirales. In some embodiments, the one or more negative-strand RNA viruses of the order Mononegavirales comprise a bornaviridae virus, a filoviridae virus, a nyamiviridae virus, a paramyxodiridae virus, a rhabdoviridae virus, or any combination thereof. In some embodiments, the one or more negative-strand RNA viruses of the order Mononegavirales comprise rabies virus, sendai virus, vesicular stomatitis virus, or any combination thereof. In some embodiments, the one or more negative-strand RNA viruses of the order Mononegavirales comprise one or more attenuating mutations. In some embodiments, the one or more negative-strand RNA viruses of the order Mononegavirales comprise an attenuated rabies virus strain. In some embodiments, the attenuated rabies virus strain comprises CVS-N2c, CVS-B2c, DRV-4, RRV-27, SRV-16, ERA, CVS-11, SAD B19, SPBN, SN-10, SN10-333, PM, LEP, SAD, or any combination thereof. In some embodiments, the polynucleotide is evolutionarily stable for at least 100 days of serial passaging. In some embodiments, after 50 days of serial passaging (a) the polynucleotide is not capable of being replicated when the stabilizing molecule is absent, (b) the polynucleotide is not capable of being replicated when the protease inhibitor is present, and/or (c) the polynucleotide is not capable of being replicated when the degron stabilizing molecule is absent. In some embodiments, after 300 days of serial passaging (a) the polynucleotide is not capable of being replicated when the stabilizing molecule is absent, (b) the polynucleotide is not capable of being replicated when the protease inhibitor is present and/or (c) the polynucleotide is not capable of being replicated when the degron stabilizing molecule is absent.

In some embodiments, transducing the target cell comprises internalization of the viral vector by the target cell. In some embodiments, the glycoprotein comprises EnvA, EnvB, EnvC, EnvD, EnvE, EnvJ, or a portion thereof. In some embodiments, the glycoprotein binding domain comprises TVA, TVB, TVC, or a portion thereof. In some embodiments, the glycoprotein is capable of mediating internalization of the viral vector by the target cell. In some embodiments, the target cell is not capable of releasing the viral vector. In some embodiments, the target cell comprises a cell associated with a disease or disorder, for example a tumor cell and/or an infected cell. In some embodiments, the first target antigen and/or a second antigen is present on a target cell. In some embodiments, the first target antigen and/or second antigen is not present on a non-target cell. In some embodiments, the first target antigen and/or second target antigen comprises a microbial antigen. In some embodiments, the first target antigen and/or second target antigen comprises a tumor-associated antigen or a tumor-specific antigen. In some embodiments, the first target antigen and/or second target antigen comprises platelet derived growth factor receptor alpha (PDGFRa), activin a receptor type 1 (ACVR1), human epidermal growth factor receptor 2 (Her2), prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, an abnormal p53 protein, mesothelin, EGFRvIII, EGFR1, diganglioside GD2, interleukin 13 receptor a (IL13Ra), fibroblast activation protein (FAP), LI cell adhesion molecule (LI CAM), or any combination thereof. In some embodiments, the first antigen binding moiety comprises a nanobody, Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof.

In some embodiments, the sender cell is capable of sensing a first inducing signal, a second inducing signal, and/or a third inducing signal. In some embodiments, the sender cell is capable of inducing expression of the glycoprotein in response to sensing a first inducing signal. In some embodiments, the sender cell is capable of inducing expression of the glycoprotein in response to sensing a threshold level of the first inducing signal. In some embodiments, the sender cell is capable of releasing the viral vector by inducing expression of the glycoprotein. In some embodiments, the sender cell is not capable of releasing the viral vector when the sender cell does not induce expression of the glycoprotein. In some embodiments, the sender cell is not capable of releasing the viral vector when the sender cell does not sense a first inducing signal. In some embodiments, the sender cell is capable of inducing expression of the first bridge protein in response to sensing a second inducing signal. In some embodiments, the sender cell is capable of inducing expression of a second bridge protein in response to sensing a third inducing signal, wherein the second bridge protein comprises a glycoprotein binding domain and a second antigen-binding moiety, wherein the second antigen-binding moiety is capable of binding a second antigen on a surface of the target cell. In some embodiments, the first bridge protein and the second bridge protein are identical. In some embodiments, the first bridge protein and the second bridge protein are different. In some embodiments, the first inducing signal, second inducing signal, and/or third inducing signal comprise an endogenous signal of the target cell. The endogenous signal of the target cell can, for example, comprise a physiological signal and/or a pathological signal, immune cell activation, inhibition of immune cell exhaustion, immune cell exhaustion, a component of a tumor microenvironment, or any combination thereof. In some embodiments, the first inducing signal, second inducing signal, and/or third inducing signal comprise an exogenous signal of the target cell. In some embodiments, the exogenous signal of the target cell comprises a small molecule (e.g., doxycycline). In some embodiments, the exogenous signal comprises a synthetic protein circuit component. In some embodiments, the sender cells comprise a synthetic receptor system, wherein the synthetic receptor system is configured to sense the first inducing signal, second inducing signal, and/or third inducing signal. In some embodiments, the sender cells comprise a Synthetic Notch (SynNotch) receptor, a Modular Extracellular Sensor Architecture (MESA) receptor, Tango, dCas9-synR, a chimeric antigen receptor, or any combination thereof.

In some embodiments, the sender cell is an immune cell (e.g., a natural killer (NK) cell), a cancer cell (e.g., a tumor infiltrating lymphocyte), and/or a stem cell. In some embodiments, the sender cell is an autologous cell derived from the subject. In some embodiments, the sender cell is an allogenic cell derived from a donor. In some embodiments, the sender cell comprises a nucleic acid encoding the polynucleotide. In some embodiments, the sender cell comprises a nucleic acid capable of expressing a full-length complementary copy of the polynucleotide. In some embodiments, the sender cell comprises a nucleic acid capable of expressing one or more of N, P, and/or L in trans.

Disclosed herein include methods for controlling viral vector replication. In some embodiments, the method comprises causing a polynucleotide of a viral vector to be internalized into a first cell of a subject, wherein the polynucleotide encodes a nucleoprotein (N), a phosphoprotein (P), a matrix protein (M), an RNA-dependent RNA polymerase (L), and one or more transgenes, and wherein the viral vector comprises an envelope comprising a glycoprotein not encoded by the polynucleotide. The method can comprise causing a first glycoprotein to be expressed by the first cell, wherein the first glycoprotein is of the species of any of the N, P, M, and L encoded by the polynucleotide, thereby a first virus particle, comprising a first replicated copy of the polynucleotide and the first glycoprotein, buds from the first cell and is internalized into a second cell. The method can comprise causing a second glycoprotein to be expressed by the first cell and a first bridge protein to be introduced into the subject, wherein the second glycoprotein, or a portion thereof, is derived of another species, thereby a second virus particle, comprising a second replicated copy of the polynucleotide and the second glycoprotein, buds from the first cell and is internalized into a second cell after a glycoprotein binding domain of the first bridge protein binds the second glycoprotein. The method can comprise causing a stabilizing molecule to be present in or expressed by the second cell, wherein at least one of the N, P, M, or L is a conditionally stable fusion protein comprising a stabilizing molecule binding domain, thereby the conditionally stable fusion protein changes from a destabilized state to a stabilized state when the stabilizing molecule binding domain binds the stabilizing molecule, and thereby a third copy of the polynucleotide is generated from the second copy of the polynucleotide. The method can comprise causing a protease inhibitor to be absent in the second cell, wherein two of the N, P, M, or L are expressed as a protease fusion protein comprising a first protein and a second protein of the two of the N, P, M, or L separated from a protease by a first cut site and a second cut site, respectively, thereby the protease cuts the first cut site and the second cut site to generate the first protein and the second protein are in active states, and thereby a fourth copy of the polynucleotide is generated from the second copy of the polynucleotide.

Disclosed herein include methods for delivering a polynucleotide to a target cell of a subject in need thereof. In some embodiments, the method comprises: providing a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; providing a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein; and administering the viral vector and the first bridge protein to the subject.

Disclosed herein include methods for delivering a polynucleotide to a target cell of a subject in need thereof. In some embodiments, the method comprises: providing a sender cell capable of releasing a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; providing a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein; and administering the sender cell and the first bridge protein to the subject.

Disclosed herein include methods for delivering a polynucleotide to a target cell of a subject in need thereof. In some embodiments, the method comprises: providing a sender cell capable of releasing: (1) a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; and (2) a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein; and administering the sender cell to the subject.

In some embodiments, the polynucleotide does not encode the glycoprotein. In some embodiments, the glycoprotein, or a portion thereof, is derived of another species than the polynucleotide. In some embodiments, the glycoprotein comprises EnvA, EnvB, EnvC, EnvD, EnvE, EnvJ, or a portion thereof. In some embodiments, at least one of the N, P, M, or L is a conditionally stable fusion protein comprising a stabilizing molecule binding domain capable of binding a stabilizing molecule, and wherein the conditionally stable fusion protein changes from a destabilized state to a stabilized state when the stabilizing molecule binding domain binds to the stabilizing molecule. P can be a conditionally stable fusion protein. In some embodiments, the stabilizing molecule binding domain comprises a nanobody, Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof. In some embodiments, the stabilizing molecule binding domain comprises an RNA aptamer, adNectin, iMab, anticalin, microbody, peptide aptamer, designed ankyrin repeat protein (DARPin), affilin, tetranectin, avimer, affibody, Kunitz domain, or any combination thereof. The stabilizing molecule can be, for example, an endogenous molecule of a target cell, a molecule specific to a cell type, a molecule specific to a disease or disorder, an exogenous molecule of a target cell, a synthetic protein circuit component, or any combination thereof. In some embodiments, the polynucleotide is capable of being replicated when the conditionally stable fusion protein is present. In some embodiments, the polynucleotide is capable of being replicated when the conditionally stable fusion protein is in the stabilized state. In some embodiments, the polynucleotide is not capable of being replicated when the conditionally stable fusion protein is in the destabilized state. In some embodiments, the polynucleotide is not capable of being replicated when the stabilizing molecule is absent. In some embodiments, the polynucleotide is capable of being replicated at a threshold concentration of the stabilizing molecule. In some embodiments, the polynucleotide is not capable of being replicated when the stabilizing molecule is present. In some embodiments, the polynucleotide is capable of being replicated at below a threshold concentration of the stabilizing molecule.

In some embodiments, two of the N, P, M, and L proteins are expressed as a protease fusion protein comprising a first protein and a second protein of the two of the N, P, M, or L separated from a protease by a first cut site and a second cut site, respectively, wherein the protease is capable of cutting the first cut site and the second cut site when the protease is not bound by a protease inhibitor, and where the first protein and the second protein are in inactive states when the first cut site and the second cut site are not cut, respectively. In some embodiments, the protease is in an active state when the first cut site and the second cut site are not cut. In some embodiments, the protease fusion protein comprises the protease, the first cut site, the second cut site, P, and L. In some embodiments, the 5'-to-3' orientation of the protease fusion is 5'-P-the first cut site-protease-the second cut site-L-3'. In some embodiments, P and/or L are in inactive states when the first cut site and/or the second cut site are not cut. The protease can be, for example, a hepatitis C virus (HCV) protease. In some embodiments, the protease inhibitor comprises asunaprevir, simeprevir, telaprevir, sovaprevir, danoprevir, ciluprevir, boceprevir, paritaprevir, or any combination thereof. In some embodiments, the polynucleotide is capable of being replicated when the first protein and the second protein are in active states. In some embodiments, the first protein and the second protein are in active states when the protease inhibitor is absent. In some embodiments, the polynucleotide is capable of being replicated when the protease inhibitor is absent. In some embodiments, the polynucleotide is not capable of being replicated when the first protein and the second protein are in inactive states. In some embodiments, the first protein and the second protein are in inactive states when the protease inhibitor is present. In some embodiments, the polynucleotide is not capable of being replicated when the protease inhibitor is present. In some embodiments, the first protein and the second protein are in inactive states at a threshold concentration of the protease inhibitor. In some embodiments, the polynucleotide is not capable of being replicated at a threshold concentration of the protease inhibitor.

In some embodiments, at least one of the N, P, M, and L is a degron fusion protein comprising a degron capable of binding a degron stabilizing molecule, and wherein the degron fusion protein changes from a destabilized state to a stabilized state when the degron binds to the degron stabilizing molecule. In some embodiments, P is a degron fusion protein. In some embodiments, the degron stabilizing molecule is an endogenous molecule of a target cell. In some embodiments, the degron stabilizing molecule is a molecule specific to a cell type. In some embodiments, the degron stabilizing molecule is a molecule specific to a disease or disorder. In some embodiments, the degron stabilizing molecule is an exogenous molecule of a target cell. In some embodiments, the degron stabilizing molecule comprises trimethoprim (TMP). In some embodiments, the degron stabilizing molecule is a synthetic protein circuit component. In some embodiments, the degron comprises a dihydrofolate reductase (DHFR) degron. In some embodiments, the polynucleotide is capable of being replicated when the degron fusion protein is in the stabilized state. In some embodiments, the polynucleotide is not capable of being replicated when the degron fusion protein is in the destabilized state. In some embodiments, the polynucleotide is not capable of being replicated when the degron stabilizing molecule is absent. In some embodiments, the polynucleotide is capable of being replicated at a threshold concentration of the stabilizing molecule.

In some embodiments, the polynucleotide does not encode a glycoprotein. In some embodiments, the one or more transgenes comprises a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof. In some embodiments, the one or more transgenes comprises cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof. In some embodiments, the one or more transgenes comprises a synthetic protein circuit component. In some embodiments, the viral vector is an RNA viral vector. In some embodiments, the polynucleotide is derived from a single-stranded RNA virus. In some embodiments, the polynucleotide is derived from a positive sense RNA virus, a negative sense RNA virus, an ambisense RNA virus, or any combination thereof. In some embodiments, the polynucleotide is derived from a negative-strand RNA virus. In some embodiments, the polynucleotide is derived from one or more negative-strand RNA viruses of the order Mononegavirales. In some embodiments, the nucleoprotein (N), phosphoprotein (P), matrix protein (M), and/or RNA-dependent RNA polymerase (L) are derived from one or more negative-strand RNA viruses of the order Mononegavirales. In some embodiments, the one or more negative-strand RNA viruses of the order Mononegavirales comprise a bornaviridae virus, a filoviridae virus, a nyamiviridae virus, a paramyxodiridae virus, a rhabdoviridae virus, or any combination thereof. In some embodiments, the one or more negative-strand RNA viruses of the order Mononegavirales comprise rabies virus, sendai virus, vesicular stomatitis virus, or any combination thereof. In some embodiments, the one or more negative-strand RNA viruses of the order Mononegavirales comprise one or more attenuating mutations. In some embodiments, the one or more negative-strand RNA viruses of the order Mononegavirales comprise an attenuated rabies virus strain. In some embodiments, the attenuated rabies virus strain comprises CVS-N2c, CVS-B2c, DRV-4, RRV-27, SRV-16, ERA, CVS-11, SAD B19, SPBN, SN-10, SN10-333, PM, LEP, SAD, or any combination thereof. In some embodiments, the polynucleotide is evolutionarily stable for at least 100 days of serial passaging. In some embodiments, after 50 days of serial passaging (a) the polynucleotide is not capable of being replicated when the stabilizing molecule is absent, (b) the polynucleotide is not capable of being replicated when the protease inhibitor is present, and/or (c) the polynucleotide is not capable of being replicated when the degron stabilizing molecule is absent. In some embodiments, after 300 days of serial passaging (a) the polynucleotide is not capable of being replicated when the stabilizing molecule is absent, (b) the polynucleotide is not capable of being replicated when the protease inhibitor is present and/or (c) the polynucleotide is not capable of being replicated when the degron stabilizing molecule is absent.

In some embodiments, transducing the target cell comprises internalization of the viral vector by the target cell. In some embodiments, the glycoprotein comprises EnvA, EnvB, EnvC, EnvD, EnvE, EnvJ, or a portion thereof. In some embodiments, the glycoprotein binding domain comprises TVA, TVB, TVC, or a portion thereof. In some embodiments, the glycoprotein is capable of mediating internalization of the viral vector by the target cell. In some embodiments, the glycoprotein mediates internalization of the viral vector by the target cell. In some embodiments, the target cell is not capable of releasing the viral vector. In some embodiments, the target cell comprises a cell associated with a disease or disorder. In some embodiments, the target cell comprises a tumor cell and/or an infected cell. In some embodiments, the first target antigen and/or a second antigen is present on a target cell. In some embodiments, the first target antigen and/or second antigen is not present on a non-target cell. In some embodiments, the first target antigen and/or second target antigen comprises a microbial antigen. In some embodiments, the first target antigen and/or second target antigen comprises a tumor-associated antigen or a tumor-specific antigen. In some embodiments, the first target antigen and/or second target antigen comprises platelet derived growth factor receptor alpha (PDGFRa), activin a receptor type 1 (ACVR1), human epidermal growth factor receptor 2 (Her2), prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, an abnormal p53 protein, mesothelin, EGFRvIII, EGFR1, diganglioside GD2, interleukin 13 receptor a (IL13Ra), fibroblast activation protein (FAP), LI cell adhesion molecule (LI CAM), or any combination thereof. In some embodiments, the first antigen binding moiety comprises a nanobody, Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof.

In some embodiments, the sender cell is capable of sensing a first inducing signal, a second inducing signal, and/or a third inducing signal. In some embodiments, the sender cell is capable of inducing expression of the glycoprotein in response to sensing a first inducing signal. In some embodiments, the sender cell induces expression of the glycoprotein in response to sensing the first inducing signal. In some embodiments, the sender cell is capable of inducing expression of the glycoprotein in response to sensing a threshold level of the first inducing signal. In some embodiments, the sender cell induces expression of the glycoprotein in response to sensing a threshold level of the first inducing signal. In some embodiments, the sender cell is capable of releasing the viral vector by inducing expression of the glycoprotein. In some embodiments, the sender cell releases the viral vector by inducing expression of the glycoprotein. In some embodiments, the sender cell is not capable of releasing the viral vector when the sender cell does not induce expression of the glycoprotein. In some embodiments, the sender cell is not capable of releasing the viral vector when the sender cell does not sense a first inducing signal. In some embodiments, the sender cell is capable of inducing expression of the first bridge protein in response to sensing a second inducing signal. In some embodiments, the sender cell induces expression of the first bridge protein in response to sensing the second inducing signal. In some embodiments, the sender cell is capable of inducing expression of a second bridge protein in response to sensing a third inducing signal, wherein the second bridge protein comprises a glycoprotein binding domain and a second antigen-binding moiety, wherein the second antigen-binding moiety is capable of binding a second antigen on a surface of the target cell. In some embodiments, the sender cell induces expression of the second bridge protein in response to sensing the third inducing signal. In some embodiments, the first inducing signal, second inducing signal, and/or third inducing signal comprise an endogenous signal of the target cell. In some embodiments, the endogenous signal of the target cell comprises a physiological signal and/or a pathological signal. In some embodiments, the endogenous signal of the target cell comprises immune cell activation. In some embodiments, the endogenous signal of the target cell comprises inhibition of immune cell exhaustion. In some embodiments, the endogenous signal of the target cell comprises immune cell exhaustion. In some embodiments, the endogenous signal of the target cell comprises a component of a tumor microenvironment. In some embodiments, the first inducing signal, second inducing signal, and/or third inducing signal comprise an exogenous signal of the target cell. In some embodiments, the exogenous signal of the target cell comprises a small molecule. In some embodiments, the exogenous signal of the target cell comprises doxycycline. In some embodiments, the exogenous signal comprises a synthetic protein circuit component. In some embodiments, the sender cells comprise a synthetic receptor system, wherein the synthetic receptor system is configured to sense the first inducing signal, second inducing signal, and/or third inducing signal. In some embodiments, the sender cells comprise a Synthetic Notch (SynNotch) receptor, a Modular Extracellular Sensor Architecture (MESA) receptor, Tango, dCas9-synR, a chimeric antigen receptor, or any combination thereof. In some embodiments, the method comprises: providing a first inducing signal; and administering the first inducing signal to the subject. In some embodiments, the sender cell induces expression of the glycoprotein. In some embodiments, the sender cell releases the viral vector. In some embodiments, the method comprises: providing a second inducing signal; and administering the second inducing signal to the subject. In some embodiments, the sender cell induces expression of the first bridge protein. In some embodiments, the method comprises: providing a third inducing signal; and administering the third inducing signal to the subject. In some embodiments, the sender cell induces expression of the second bridge protein.

In some embodiments, the sender cell is an immune cell (e.g., a natural killer (NK) cell), a cancer cell (e.g., a tumor infiltrating lymphocyte), and/or a stem cell. The sender cell can be, for example, an autologous cell derived from the subject or an allogenic cell derived from a donor. In some embodiments, the sender cell comprises a nucleic acid encoding the polynucleotide or a nucleic acid capable of expressing a full-length complementary copy of the polynucleotide. In some embodiments, the sender cell expresses a full-length complementary copy of the polynucleotide. In some embodiments, the sender cell comprises a nucleic acid capable of expressing one or more N, P, and/or L in trans. In some embodiments, the sender cell expresses one or more of N, P, and/or L in trans. In some embodiments, the polynucleotide is delivered to a target cell of the subject. In some embodiments, the one or more transgenes is expressed in the target cell.

In some embodiments, the method comprises: providing the protease inhibitor; and administering the protease inhibitor to the subject. In some embodiments, replication of the polynucleotide ceases following administration of the protease inhibitor to the subject. In some embodiments, the expression of the one or more transgenes in the target cell ceases following administration of the protease inhibitor to the subject. In some embodiments, administering comprises aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or a combination thereof.

DETAILED DESCRIPTION

Figure 1A:
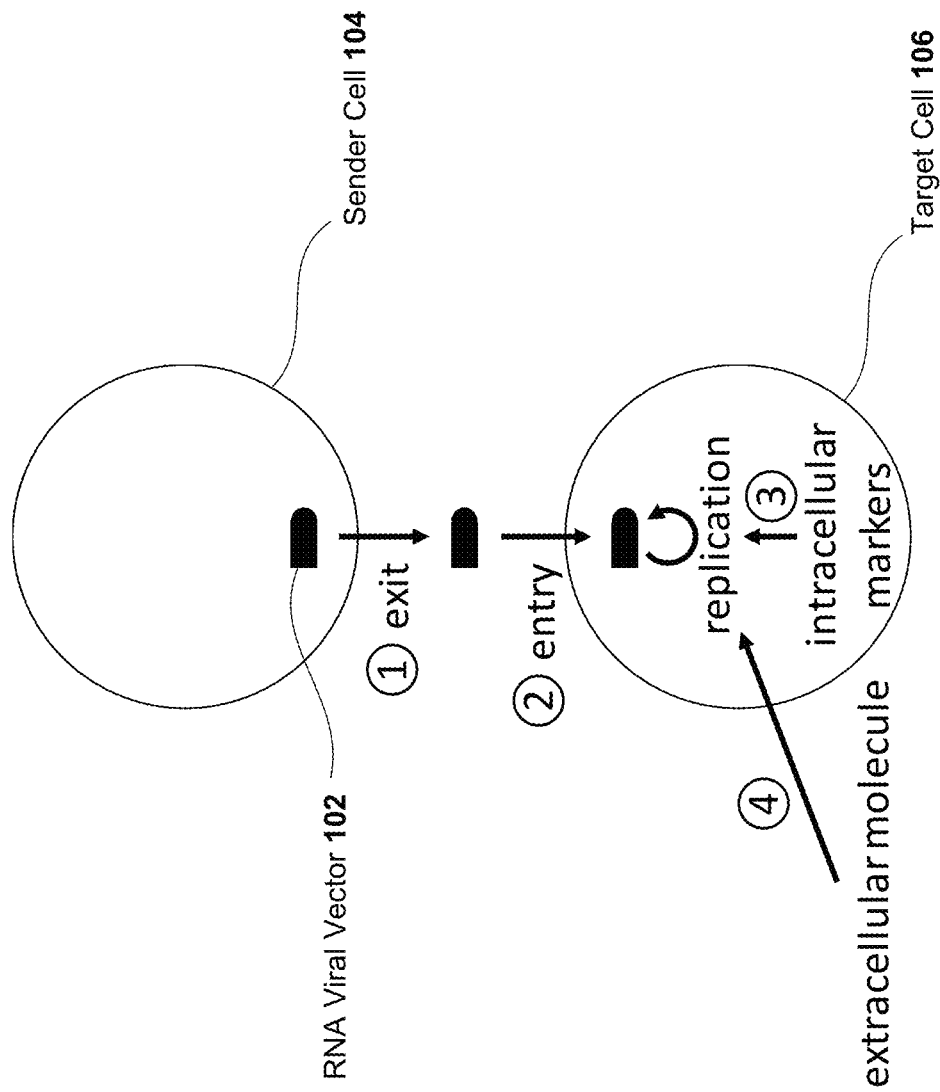
FIG. 1A is a schematic illustration showing a non-limiting exemplary embodiment of a viral vector system engineered to respond to four distinct levels of control during its life cycle.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include viral vectors. In some embodiments, the viral vector comprises: a polynucleotide encoding a nucleoprotein (N), a phosphoprotein (P), a matrix protein (M), an RNA-dependent RNA polymerase (L), and one or more transgenes, wherein at least one of the N, P, M, or L is a conditionally stable fusion protein comprising a stabilizing molecule binding domain capable of binding a stabilizing molecule, and wherein the conditionally stable fusion protein changes from a destabilized state to a stabilized state when the stabilizing molecule binding domain binds to the stabilizing molecule, and/or wherein two of the N, P, M, or L are expressed as a protease fusion protein comprising a first protein and a second protein of the two of the N, P, M, or L separated from a protease by a first cut site and a second cut site, respectively, wherein the protease is capable of cutting the first cut site and the second cut site when the protease is not bound by a protease inhibitor, and wherein the first protein and the second protein are in inactive states when the first cut site and the second cut site are not cut, respectively; and an envelope comprising a glycoprotein not encoded by the polynucleotide, wherein the glycoprotein is of the species of any of the N, P, M, and L encoded by the polynucleotide, and/or wherein the glycoprotein, or a portion thereof, is derived of another species, and wherein a glycoprotein binding domain of a first bridge protein is capable of binding the glycoprotein.

Disclosed herein include viral vectors. In some embodiments, the viral vector comprises: a polynucleotide encoding a nucleoprotein (N), a phosphoprotein (P), a matrix protein (M), an RNA-dependent RNA polymerase (L), and one or more transgenes; and an envelope comprising a glycoprotein not encoded by the polynucleotide.

Disclosed herein include viral vectors. In some embodiments, the viral vector comprises: a polynucleotide encoding a nucleoprotein (N), a phosphoprotein (P), a matrix protein (M), an RNA-dependent RNA polymerase (L), and one or more transgenes, and wherein the polynucleotide does not encode a glycoprotein; and a glycoprotein, wherein the glycoprotein, or a portion thereof, is derived of another species than the polynucleotide.

Disclosed herein include viral vectors. In some embodiments, the viral vector comprises a polynucleotide encoding: a nucleoprotein (N), a phosphoprotein (P), a matrix protein (M), an RNA-dependent RNA polymerase (L), and one or more transgenes, wherein at least one of the N, P, M, or L is a conditionally stable fusion protein comprising a stabilizing molecule binding domain capable of binding a stabilizing molecule, and wherein the conditionally stable fusion protein changes from a destabilized state to a stabilized state when the stabilizing molecule binding domain binds to the stabilizing molecule.

Disclosed herein include viral vectors. In some embodiments, the viral vector comprises a polynucleotide encoding: a nucleoprotein (N), a phosphoprotein (P), a matrix protein (M), an RNA-dependent RNA polymerase (L), and one or more transgenes, wherein two of the N, P, M, or L are expressed as a protease fusion protein comprising a first protein and a second protein of the two of the N, P, M, or L separated from a protease by a first cut site and a second cut site, respectively, wherein the protease is capable of cutting the first cut site and the second cut site when the protease is not bound by a protease inhibitor, and wherein the first protein and the second protein are in inactive states when the first cut site and the second cut site are not cut, respectively.

Disclosed herein include viral vectors. In some embodiments, the viral vector comprises a polynucleotide encoding: a nucleoprotein (N), a phosphoprotein (P), a matrix protein (M), an RNA-dependent RNA polymerase (L), and one or more transgenes, wherein at least one of the N, P, M, or L is a degron fusion protein comprising a degron capable of binding a degron stabilizing molecule, and wherein the degron fusion protein changes from a destabilized state to a stabilized state when the degron binds to the degron stabilizing molecule.

Disclosed herein include systems for delivering a polynucleotide to a target cell of a subject in need thereof. In some embodiments, the system comprises: a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; and a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein.

Disclosed herein include systems for delivering a polynucleotide to a target cell of a subject in need thereof. In some embodiments, the system comprises: a sender cell capable of releasing a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; and a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein.

Disclosed herein include systems for delivering a polynucleotide to a target cell of a subject in need thereof. In some embodiments, the system comprises: a sender cell capable of releasing: (1) a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; and (2) a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein.

Disclosed herein include methods for controlling viral vector replication. In some embodiments, the method comprises causing a polynucleotide of a viral vector to be internalized into a first cell of a subject, wherein the polynucleotide encodes a nucleoprotein (N), a phosphoprotein (P), a matrix protein (M), an RNA-dependent RNA polymerase (L), and one or more transgenes, and wherein the viral vector comprises an envelope comprising a glycoprotein not encoded by the polynucleotide. The method can comprise causing a first glycoprotein to be expressed by the first cell, wherein the first glycoprotein is of the species of any of the N, P, M, and L encoded by the polynucleotide, thereby a first virus particle, comprising a first replicated copy of the polynucleotide and the first glycoprotein, buds from the first cell and is internalized into a second cell. The method can comprise causing a second glycoprotein to be expressed by the first cell and a first bridge protein to be introduced into the subject, wherein the second glycoprotein, or a portion thereof, is derived of another species, thereby a second virus particle, comprising a second replicated copy of the polynucleotide and the second glycoprotein, buds from the first cell and is internalized into a second cell after a glycoprotein binding domain of the first bridge protein binds the second glycoprotein. The method can comprise causing a stabilizing molecule to be present in or expressed by the second cell, wherein at least one of the N, P, M, or L is a conditionally stable fusion protein comprising a stabilizing molecule binding domain, thereby the conditionally stable fusion protein changes from a destabilized state to a stabilized state when the stabilizing molecule binding domain binds the stabilizing molecule, and thereby a third copy of the polynucleotide is generated from the second copy of the polynucleotide. The method can comprise causing a protease inhibitor to be absent in the second cell, wherein two of the N, P, M, or L are expressed as a protease fusion protein comprising a first protein and a second protein of the two of the N, P, M, or L separated from a protease by a first cut site and a second cut site, respectively, thereby the protease cuts the first cut site and the second cut site to generate the first protein and the second protein are in active states, and thereby a fourth copy of the polynucleotide is generated from the second copy of the polynucleotide.

Disclosed herein include methods for delivering a polynucleotide to a target cell of a subject in need thereof. In some embodiments, the method comprises: providing a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; providing a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein; and administering the viral vector and the first bridge protein to the subject.

Disclosed herein include methods for delivering a polynucleotide to a target cell of a subject in need thereof. In some embodiments, the method comprises: providing a sender cell capable of releasing a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; providing a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein; and administering the sender cell and the first bridge protein to the subject.

Disclosed herein include methods for delivering a polynucleotide to a target cell of a subject in need thereof. In some embodiments, the method comprises: providing a sender cell capable of releasing: (1) a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; and (2) a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein; and administering the sender cell to the subject.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the term "vector" refers to a polynucleotide construct, typically a plasmid or a virus, used to transmit genetic material to a host cell (e.g., a target cell). Vectors can be, for example, viruses, plasmids, cosmids, or phage. A vector can be a viral vector. A vector as used herein can be composed of either DNA or RNA. In some embodiments, a vector is composed of DNA. An "expression vector" is a vector that is capable of directing the expression of a protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The term "construct," as used herein, refers to a recombinant nucleic acid that has been generated for the purpose of the expression of a specific nucleotide sequence(s), or that is to be used in the construction of other recombinant nucleotide sequences.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

The term "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, 2A sequences or elements refer to small peptides introduced as a linker between two proteins, allowing autonomous intraribosomal self-processing of polyproteins (See e.g., de Felipe. Genetic Vaccines and Ther. 2: 13 (2004); de Felipe et al. Traffic 5:616-626 (2004)). These short peptides allow co-expression of multiple proteins from a single vector. Many 2A elements are known in the art. Examples of 2A sequences that can be used in the methods and system disclosed herein, without limitation, include 2A sequences from the foot-and-mouth disease virus (F2A), equine rhinitis A virus (E2A), Thosea asigna virus (T2A), and porcine teschovirus-1 (P2A).

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "enhancer" refers to a type of regulatory element that can increase the efficiency of transcription, regardless of the distance or orientation of the enhancer relative to the start site of transcription.

As used herein, the term "variant" refers to a polynucleotide (or polypeptide) having a sequence substantially similar to a reference polynucleotide (or polypeptide). In the case of a polynucleotide, a variant can have deletions, substitutions, additions of one or more nucleotides at the 5' end, 3' end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans. In the case of a polypeptide, a variant can have deletions, substitutions, additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polypeptide as determined by sequence alignment programs known by skilled artisans.

As used herein, the term "transduction" refers to the introduction of a nucleic acid into a host cell, such as by contacting the cell with an RNA viral vector as described below.

As used herein, the term "effective amount" refers to an amount sufficient to effect beneficial or desirable biological and/or clinical results.

As used herein, a "subject" refers to an animal that is the object of treatment, observation or experiment. "Animal" includes cold- and warm-blooded vertebrates and invertebrates such as fish, shellfish, reptiles, and in particular, mammals. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a human. However, in some embodiments, the mammal is not a human.

As used herein, the term "treatment" refers to an intervention made in response to a disease, disorder or physiological condition manifested by a patient. The aim of treatment may include, but is not limited to, one or more of the alleviation or prevention of symptoms, slowing or stopping the progression or worsening of a disease, disorder, or condition and the remission of the disease, disorder or condition. The term "treat" and "treatment" includes, for example, therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments treatment may reduce the level of RAS signaling in the subject, thereby to reduce, alleviate, or eradicate the symptom(s) of the disease(s). As used herein, the term "prevention" refers to any activity that reduces the burden of the individual later expressing those RAS-related disease symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications. The term "prevent" does not require the 100% elimination of the possibility of an event. Rather, it denotes that the likelihood of the occurrence of the event has been reduced in the presence of the compound or method.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as Tween, polyethylene glycol (PEG), and Pluronics. Auxiliary, stabilizer, emulsifier, lubricant, binder, pH adjuster controller, isotonic agent and other conventional additives may also be added to the carriers.

Viral Vectors Engineered to Respond to Distinct Layers of Control

In biomedical applications, it is often necessary to deliver biomolecules (e.g., polynucleotides encoding transgene(s)) into patient cells, and it is imperative to eliminate mutagenic risks posed by delivery vectors. The vast majority of therapeutic genes and synthetic circuits have been delivered on DNA vectors amenable to transcriptional regulation. Some of these vectors (e.g., lentivirus) insert into the host genome, while others (e.g., adeno-associated virus), though non-inserting by nature or by design, are still not entirely free of mutagenic insertion, due to the presence of exogenous DNA in close proximity to genomic DNA. Such insertions are unpredictable and irreversible, and could be oncogenic even if their frequencies are very low. Thus, a serious problem associated with the delivery of genes in the above-mentioned approaches is the integration of genetic material from a viral vector into the host cell genomic DNA which may cause malignant transformation of the host cell. In particular, retrovirus-mediated delivery of genes can result in genomic integration of the transgene. This may trigger activation of oncogenes or disrupt tumor suppressor genes, leading to malignant cell transformation. Another problem associated with integrating viral vectors is the fact that integrated and down-regulated transgenes may be re-activated to cause cellular transformation. These considerations suggest that a better solution would be a DNA-free vector. However, a key obstacle to such systems is relative lack of regulation methods. An outstanding issue is the risk that a delivery vector can be transmitted to neighboring healthy cells of the patient or from the patient to other individuals or into the environment. A further problem in the art is that a virus vector may persist and cause adverse effects, such as an immune reaction against viral components or delayed effects of viral infection. Moreover, the prolonged expression of foreign genes may also result in an autoimmune-like reaction to self-antigens or interfere with cellular processes like signaling pathways. There is a need for DNA-free delivery vectors engineered to respond to multiple levels of control.

The compositions, methods, and systems provided herein address the above-mentioned issues. There are provided, in some embodiments, RNA viral vectors comprising a polynucleotide encoding one or more transgenes. In some embodiments, the polynucleotide comprises one or more features to ensure controlled replication of viral vector and release of the viral vector. There are provided, in some embodiments, sender cells for producing said viral vectors in a controlled fashion vivo and/or in vitro. There are provided, in some embodiments, bridge proteins for the controlled transduction of target cells by the viral vectors disclosed herein. Additionally, there are provided regulatory molecules for the control for the activity and life cycle of the viral vectors and sender cells provided herein, such as, for example, stabilizing molecules, first inducing signals, second inducing signals, third inducing signals, degron stabilizing molecules, and/or protease inhibitors. There are provided, in some embodiments, systems for delivering a polynucleotide to a target cell of a subject in need thereof comprising the above-mentioned viral vectors, bridge proteins, sender cells, and/or regulatory molecules. There are provided, in some embodiments, methods for delivering a polynucleotide to a target cell of a subject in need thereof comprising the above-mentioned viral vectors, bridge proteins, sender cells, and/or regulatory molecules.

The RNA-virus-based delivery vectors provided herein address above-mentioned limitations of DNA vectors, such as their mutagenic risks. In some embodiments, the viral vectors provided herein are derived from species in Mononegavirales (e.g. rabies virus). Rabies virus is a model for engineering RNA viruses and engineered rabies virus finds applications to many therapeutic areas, such as, for example, neuroscience (e.g., trans-synaptic tracing). Rabies virus was first genetically modified virus in the order of Mononegavirales. Additionally, Rabies virus is generalizable to others in Mononegavirales, such as, for example, vesicular stomatitis virus (oncolysis) and Sendai virus (reprogramming). Mononegavirales (e.g. rabies virus) can have higher genomic stability, lower cytotoxicity and immunogenicity, and the potential for high genomic cargo capacity. In some embodiments, engineered rabies virus is disclosed as a non-limiting example of the compositions, methods, and systems provided herein. In some embodiments, the compositions, methods, and systems provided herein bypass the risks associated with persistence of a virus vector in a host, such as immune reactions against viral components, delayed effects of viral infection, autoimmune-like reaction to self-antigens, altered expression of the endogenous host genes and/or unpredictable adverse events.

There are provided, in some embodiments, viral vectors engineered to respond to multiple levels of control. In some embodiments, the viral vectors are engineered to respond to one, two, three, four, or more, distinct layers or levels of control during its life cycle (e.g., during its transmission and replication). In some embodiments, these four levels of control can be integrated into a single viral vector. Additionally, in some embodiments, the layers of control disclosed herein (e.g., layers 1-3) can also be designed to respond to biomedically relevant inputs such as, for example, cancer markers. In some embodiments, the layers of control render the viral vector conducive to high specificity and safety. Some embodiments of the compositions, methods, and systems provided herein employ a sender-receiver design comprising sender cells (e.g., homing immune cells) and receiver cells (e.g., target cells). A sender cell can harbor the viral vector and release the viral vector in some embodiments. Sender cells can perform homing to target diseased tissues and cells. Receiver cells can be target cells into which viral vectors deliver their cargo (e.g., polynucleotides comprising one or more transgenes). FIG. 1A is a schematic illustration showing a non-limiting exemplary embodiment of a viral vector system engineered to respond to four distinct levels of control during its life cycle. The first layer of control can comprise the controlled exit of RNA viral vector 102 from sender cell 104 (e.g., release by budding). The second layer of control can comprises restriction of viral vector entry (e.g., transduction) to specific cells (e.g., a target cell 106), which may be expressing an antigen of interest on its surface. The third layer of control can comprise a modulation of viral vector replication in response to intracellular markers of interest (e.g., stabilizing molecules). A fourth layer of control can comprise external (e.g., exogenous) control of viral vector replication by contacting the target cell 106 with an extracellular molecule.

In some embodiments, a first layer of control comprises controlled viral vector exit from sender cells (e.g., viral vector release from sender cells as virus particles by budding). In some such embodiments, the viral vector polynucleotide (e.g., viral vector genome) does not comprise glycoprotein (ΔG). Viral vector exit from sender cells can be dependent on expression of glycoprotein. In some embodiments, glycoprotein is provided in trans from the sender cells. In some embodiments, viral exit from sender cells can be regulated by inducible expression of glycoprotein. In some such embodiments, sender cells are configured to induce glycoprotein expression in response to pathological and/or physiological signals (e.g. a first inducing signal). In some such embodiments, the sender cell comprises sensors (e.g., Tango, SynNotch, MESA) that respond to intracellular signals and induce glycoprotein expression.

Figure 2A:
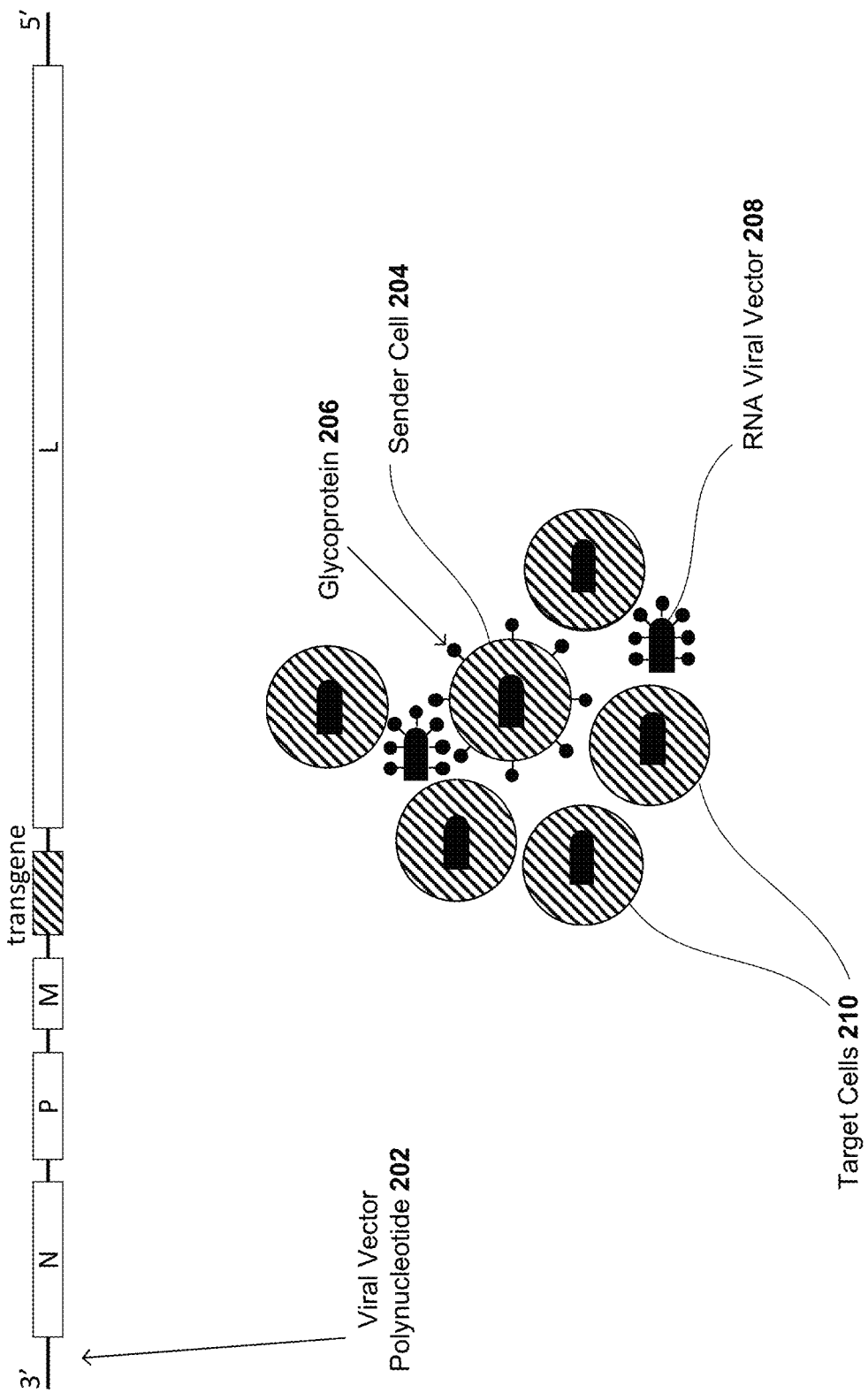
FIG. 2A shows a non-limiting exemplary schematic illustration of a first layer of control of the viral vector provided herein.

FIG. 2A shows a non-limiting exemplary schematic illustration of a first layer of control of the viral vector provided herein. Viral vector polynucleotide 202 comprises a transgene (e.g., mCherry) and does not encode a G protein. A sender cell 204 is configured to express the glycoprotein 206 upon an inducing signal (e.g., a first inducing signal, doxycycline, a pathological and/or physiological signal). Upon expression of the glycoprotein, the RNA viral vector 208 can be released by the sender cell (e.g., by budding). In some embodiments, the sender cell is a homing immune cell. In some embodiments, the inducible signal occurs when the sender cell is in close proximity to target cells 210.

In some embodiments, a second layer of control comprises restriction of viral vector entry (e.g., transduction) to specific cells (e.g., target cells) expressing an antigen of interest on its surface. In some embodiments, a second layer of control comprises viral vector pseudotyping. In some embodiments, the viral vectors disclosed herein are pseudotyped with a different glycoprotein (e.g., glycoprotein EnvA from avian virus). In some embodiments, there are provided bridge proteins. Bridge proteins can comprise a glycoprotein binding domain (e.g., TVA, TVB, TVC, or a portion thereof) capable of binding the glycoprotein. Bridge proteins can comprise an antigen-binding moiety capable of binding an antigen on a surface of a target cell. The bridge protein can be a fusion protein (e.g., fusion between TVA that binds to EnvA and a single-domain antibody that binds a target cell antigen). In some embodiments, the bridge protein and/or glycoprotein mediates viral entry through a cell surface antigen. In some embodiments, the viral vector is capable of transducing the target cell when the first antigen-binding moiety is bound to the first antigen and the glycoprotein binding domain is bound to the glycoprotein and a receptor on the cell surface of the target cell. In some embodiments, the antigen-binding moiety targets cancer-specific cell-surface molecules (e.g., HER2, EGFRvIII, CEA).

Figure 3A:
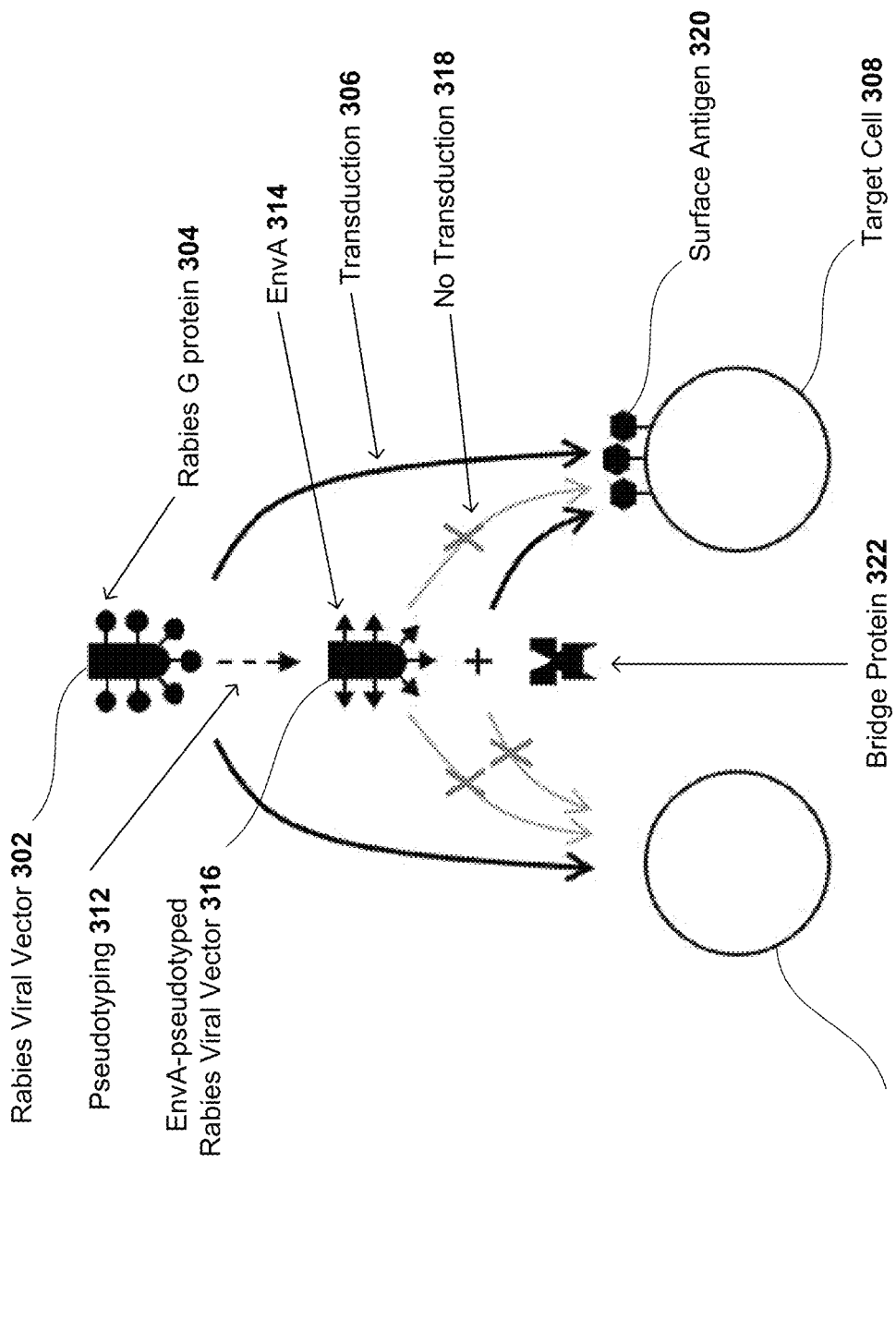
FIGS. 3A-3B show a non-limiting exemplary schematic illustration of a second layer of control of the viral vector provided herein.

FIG. 3A shows a non-limiting exemplary schematic illustration of a second layer of control of the viral vector provided herein. An RNA viral vector (e.g., rabies viral vector 302) comprising a G protein (e.g., rabies G protein 304) is capable of transducing 306 both a target cell 308 and a non-target cell 310. The RNA viral vector can be, for example, pseudotyped 312 by replacement of the G protein with a foreign viral envelope protein (e.g., EnvA 314) to generate a pseudotyped RNA viral vector (e.g., EnvA-pseudotyped Rabies Viral Vector 316). The receptors of the foreign viral envelope protein can be orthogonal to mammalian cells, therefore no transduction 318 occurs with the pseudotyped RNA viral vector alone. Target cell 308 can comprise a surface antigen 320 absent on non-target cell 310. A bridge protein 322 can bind both the pseudotyped RNA viral vector (e.g., with a glycoprotein binding domain) and a surface antigen surface antigen 320, thereby enabling the pseudotyped RNA viral vector to transduce 306 the target cell 308 but not the not non-target cell 310.

Figure 3B:
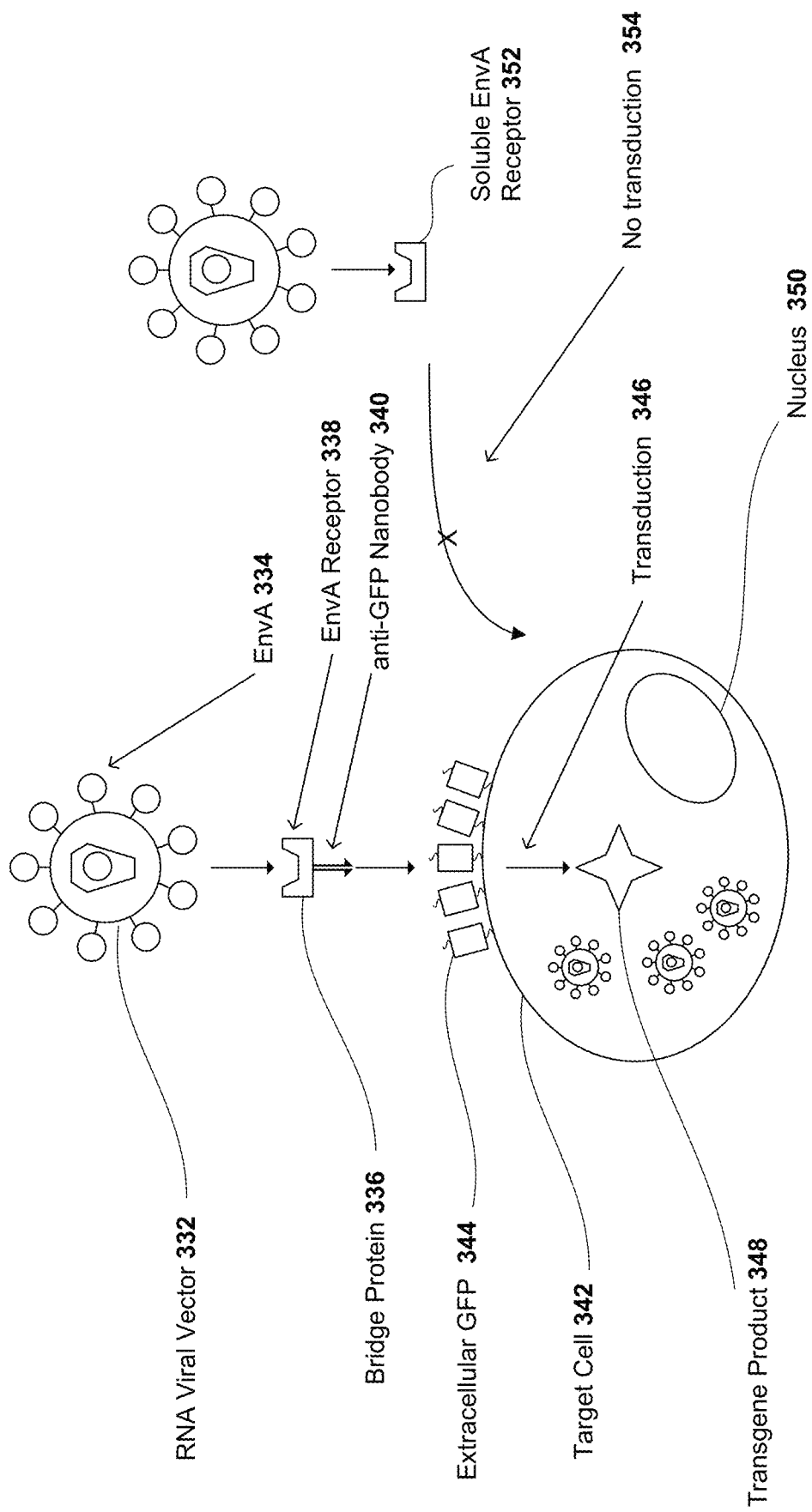

FIG. 3B shows a non-limiting exemplary schematic illustration of a second layer of control of the viral vector provided herein. An RNA viral vector 332 comprises an envelope comprising EnvA 334. A bridge protein 336 can comprise a glycoprotein binding domain (e.g., EnvA receptor 338) and an antigen-binding moiety (e.g., an anti-GFP nanobody 340). A target cell 342 comprises extracellular GFP 344 on its surface. The bridge protein 336 mediates transduction 346 of the target cell 342. The RNA viral vector can encode a transgene product 348 (e.g., mCherry). The RNA viral vector can be absent from the nucleus 350. Soluble glycoprotein binding domain (e.g., soluble EnvA receptor 352) cannot mediate transduction 354.

In some embodiments, a third layer of control comprises restricting viral vector replication to cells comprising a stabilizing molecule. In some embodiments, at least one of the N, P, M, or L is a conditionally stable fusion protein. In some such embodiments, at least one of the N, P, M, or L is a tagged (e.g., operatively linked) with a conditionally stable antigen-binding domain (e.g., a conditionally stable nanobody) that destabilizes the tagged viral protein (e.g. phosphoprotein) and is stabilized in the presence of its antigen. In some embodiments, the stabilizing molecule binding domain (e.g., a conditionally stable nanobody) functions as a degron. In some such embodiments, viral vector replication can be restricted to cells expressing the corresponding intracellular antigen. In some embodiments, the third layer of control responds to inputs from synthetic protein circuits (e.g., protease circuits) to regulate viral replication, which can, in some embodiments, enable it to be interfaced with the intracellular states.

FIG. 4A shows a non-limiting exemplary schematic illustration of a third layer of control of the viral vector provided herein. Viral vector polynucleotide 402 comprises a transgene (e.g., encoding mCherry), does not encode a G protein, and encodes a conditionally stable fusion protein 404. The conditionally stable fusion protein 404 comprises a fusion of P protein 406 and a stabilizing molecule binding domain (e.g., a GFP-binding nanobody that functions as a degron, dGBP 408)). The conditionally stable fusion protein 404 changes from a destabilized state to a stabilized state when the stabilizing molecule binding domain binds to the stabilizing molecule (e.g., GFP 410).

In some embodiments, a fourth layer of control comprises external (e.g., exogenous) control of viral vector replication. In some such embodiments, two of the N, P, M, and L are expressed as a protease fusion protein comprising a first protein and a second protein of the two of the N, P, M, or L separated from a protease by a first cut site and a second cut site, respectively. The protease can be capable of cutting the first cut site and the second cut site when the protease is not bound by a protease inhibitor. The first protein and the second protein are in inactive states when the first cut site and the second cut site are not cut, respectively. In some embodiments, two of the N, P, M, or L (e.g., P and L) are fused into a single reading frame, with an intervening protease (e.g., HCV protease) flanked by its cleavage sites. The protease (e.g., HCV protease) can cleave the single peptide into distinct proteins (e.g., P and L proteins) and support viral replication, but can be suppressed by a drug (e.g., a protease inhibitor, ASV). Thus, in some embodiments, replication of the viral vector is inhibited by the addition of the protease inhibitor. In some embodiments, this layer of control is evolutionarily stable (e.g., maintained regulatability after 80 or more days of passage). In some embodiments, the fourth layer of control comprises at least one of the N, P, M, or L is expressed as a degron fusion protein. In some such embodiments, the degron is capable of binding a degron stabilizing molecule, and the degron fusion protein changes from a destabilized state to a stabilized state when the degron binds to the degron stabilizing molecule. In some embodiments, at least one of the N, P, M, or L is tagged with a degron (e.g., a dihydrofolate reductase (DHFR) degron) that is stabilized by a small-molecule drug (e.g., trimethoprim (TMP)). In some embodiments, the degron fusion protein is configured to ensure its translation and/or evolutionary stability. In some embodiments, the fourth layer of control shows unexpected evolutionary stability. In some embodiments, the replication of the viral vector is rendered dependent on an external drug, which thereby serves as a safety switch. Administration of the protease inhibitor and/or ceased administration of the degron stabilizing molecule can, for example, remove the viral vector from transduced cells.

FIG. 5A shows a non-limiting exemplary schematic illustration of a fourth layer of control of the viral vector provided herein. Viral vector polynucleotide 502 comprises a transgene (e.g., encoding mCherry), does not encode a G protein, and encodes a protease fusion protein. The protease fusion protein can comprise P and L separated by a protease (e.g., HCV protease) by a first cleavage site and a second cleavage site, respectively. The cleavage sites can be recognized by the protease. The protease can be inhibited by a protease inhibitor (e.g., ASV). P and L can be in inactive states in the presence of protease inhibitor, thereby abrogating replication.

FIG. 6A shows a non-limiting exemplary schematic illustration of a fourth layer of control of the viral vector provided herein. Viral vector polynucleotide 602 comprises a transgene (e.g., encoding mCherry), does not encode a G protein, and encodes a degron fusion protein. The degron fusion protein can comprise P and a degron, such as, for example, DHFR. The degron fusion protein can be stabilized by a degron stabilizing molecule (e.g., an inhibitor of the degron, TMP).

Disclosed herein include viral vectors. In some embodiments, the viral vector comprises: a polynucleotide encoding a nucleoprotein (N), a phosphoprotein (P), a matrix protein (M), an RNA-dependent RNA polymerase (L), and one or more transgenes, wherein at least one of the N, P, M, or L is a conditionally stable fusion protein comprising a stabilizing molecule binding domain capable of binding a stabilizing molecule, and wherein the conditionally stable fusion protein changes from a destabilized state to a stabilized state when the stabilizing molecule binding domain binds to the stabilizing molecule, and/or wherein two of the N, P, M, or L are expressed as a protease fusion protein comprising a first protein and a second protein of the two of the N, P, M, or L separated from a protease by a first cut site and a second cut site, respectively, wherein the protease is capable of cutting the first cut site and the second cut site when the protease is not bound by a protease inhibitor, and wherein the first protein and the second protein are in inactive states when the first cut site and the second cut site are not cut, respectively; and an envelope comprising a glycoprotein not encoded by the polynucleotide, wherein the glycoprotein is of the species of any of the N, P, M, and L encoded by the polynucleotide, and/or wherein the glycoprotein, or a portion thereof, is derived of another species, and wherein a glycoprotein binding domain of a first bridge protein is capable of binding the glycoprotein.

Disclosed herein include viral vectors. In some embodiments, the viral vector comprises: a polynucleotide encoding a N, a P, a M, a L, and one or more transgenes; and an envelope comprising a glycoprotein not encoded by the polynucleotide. In some embodiments, the glycoprotein is of the species of the polynucleotide, while in some embodiments, the glycoprotein, or a portion thereof, can be derived of another species than the polynucleotide. The viral vector transducing the target cell can comprise internalization of the viral vector by the target cell.

Disclosed herein include viral vectors. In some embodiments, the viral vector comprises: a polynucleotide encoding a P, a N, a M, a L, and one or more transgenes, and wherein the polynucleotide does not encode a glycoprotein; and a glycoprotein, wherein the glycoprotein, or a portion thereof, is derived of another species than the polynucleotide.

Disclosed herein include methods for controlling viral vector replication. In some embodiments, the method comprises causing a polynucleotide of a viral vector to be internalized into a first cell of a subject, wherein the polynucleotide encodes a N, a P, a M, a L, and one or more transgenes, and wherein the viral vector comprises an envelope comprising a glycoprotein not encoded by the polynucleotide. The method can comprise causing a first glycoprotein to be expressed by the first cell, wherein the first glycoprotein is of the species of any of the N, P, M, and L encoded by the polynucleotide, thereby a first virus particle, comprising a first replicated copy of the polynucleotide and the first glycoprotein, buds from the first cell and is internalized into a second cell. The method can comprise causing a second glycoprotein to be expressed by the first cell and a first bridge protein to be introduced into the subject, wherein the second glycoprotein, or a portion thereof, is derived of another species, thereby a second virus particle, comprising a second replicated copy of the polynucleotide and the second glycoprotein, buds from the first cell and is internalized into a second cell after a glycoprotein binding domain of the first bridge protein binds the second glycoprotein. The method can comprise causing a stabilizing molecule to be present in or expressed by the second cell, wherein at least one of the N, P, M, or L is a conditionally stable fusion protein comprising a stabilizing molecule binding domain, thereby the conditionally stable fusion protein changes from a destabilized state to a stabilized state when the stabilizing molecule binding domain binds the stabilizing molecule, and thereby a third copy of the polynucleotide is generated from the second copy of the polynucleotide. The method can comprise causing a protease inhibitor to be absent in the second cell, wherein two of the N, P, M, or L are expressed as a protease fusion protein comprising a first protein and a second protein of the two of the N, P, M, or L separated from a protease by a first cut site and a second cut site, respectively, thereby the protease cuts the first cut site and the second cut site to generate the first protein and the second protein are in active states, and thereby a fourth copy of the polynucleotide is generated from the second copy of the polynucleotide.

Viral Vectors

There are provided, in some embodiments, viral vectors. The viral vector can be an RNA viral vector. The polynucleotide can be derived from a positive sense RNA virus, a negative sense RNA virus, an ambisense RNA virus, or any combination thereof. The polynucleotide can be derived from a single-stranded RNA virus. The polynucleotide can be derived from a negative-strand RNA virus. The polynucleotide can be derived from one or more negative-strand RNA viruses of the order Mononegavirales. The nucleoprotein (N), phosphoprotein (P), matrix protein (M), and/or RNA-dependent RNA polymerase (L) can be derived from one or more negative-strand RNA viruses of the order Mononegavirales (e.g., a bornaviridae virus, a filoviridae virus, a nyamiviridae virus, a paramyxodiridae virus, a rhabdoviridae virus, or any combination thereof). The Mononegavirales virus can comprise rabies virus, sendai virus, vesicular stomatitis virus, or any combination thereof. A Mononegavirales-based viral vector can comprise one or more attenuating mutations. In some embodiments, the one or more negative-strand RNA viruses of the order Mononegavirales can comprise an attenuated rabies virus strain (e.g., CVS-N2c, CVS-B2c, DRV-4, RRV-27, SRV-16, ERA, CVS-11, SAD B19, SPBN, SN-10, SN10-333, PM, LEP, SAD, or any combination thereof).

The viral vectors provided herein can be derived from any non-segmented, negative-strand RNA virus of the order Mononegavirales, including wild-type strains, mutated strains, laboratory-passaged strains, vaccination strains, genetically constructed strains, and the like. The viral vectors provided herein can be derived from negative-strand RNA viruses belonging to the families Paramyxovirdae, Rhabdoviridae, Filoviridae, Bornaviridae, Arenaviridae or Bunyaviridae, or recombinant variants thereof. Paramyxoviruses include but are not limited to Avulavirus (e.g. Newcastle disease virus), Henipavirus (e.g., Hendravirus and Nipah virus), Morbillivirus (e.g., measles, rinderpest, and canine distemper); Respirovirus (e.g., Sendai, human parainfluenza viruses 1 and 3, bovine parainfluenza virus); Rubulavirus (e.g., mumps, simian parainfluenza virus 5, human parainfluenza virus 2, and menangle virus); Pneumoviridae (e.g., human respiratory syncytial virus, pneumoniavirus of mice and bovine respiratory syncytial virus); subfamily Metapneumovirus (e.g., avian pneumovirus and human metapneumovirus). Rhabdoviridae, include but are not limited to Cytorhabdovirus (e.g., Lettuce necrotic yellows virus); Ephemerovirus (e.g., Bovine ephemeral fever virus); Lyssavirus (e.g., rabies, mokola and Australian bat lyssavirus); Novirhabdovirus (e.g., infectious hematopoietic necrosis virus and viral hemorrhagic septicemia); Nucleorhabdovirus (e.g., *sonchus* yellow net virus and potato yellow dwarf virus); Vesiculovirus (e.g. Vesicular stomatitis Indiana virus, Vesicular stomatitis New Jersey virus and spring viremia of carp). Filoviruses include but are not limited to Marburg virus and Ebola virus.

In some embodiments, the viral vector is derived from one or more of rabies virus strains according to the NCBI Accession Nos. JQ730682, AF499686, AB569299, AB8391 70, AB781935, FJ959397, AB362483, EF206720, EF20671 8, EF20671 7, EF20671 5, EF206714, EF206713, EF206712, EF20671 1, EF206710, EF206709, EF206708, EF206707, EU182346, HM535790, GQ918139, EU877071, EU877070, EU877069, EU1 82347, M31046, EU877068, EU877067, EF542830, AB8391 69, JQ647510, KC1 69986, JX088694, JQ730682, JN609295, JN23441 1, HQ31 791 8, EF20671 9, EF5641 74, EU643590, JQ946087, FJ913470 HQ891318, AB645847, AB569299, AY705373, GU565704, GU565703, FJ577895, JX276550, FJ866836, FJ866835, DQ875051, DQ875050, AB128149, AB009663, AB044824, JQ944709, EU345004, EU345003, EU345002, AB608731, EF5641 73, JQ423952, AB61 8037, AB61 8036, AB61 8035, AB61 8034, AB61 8033, AB61 8032, AB085828, M1321 5, M21 634, AB247437, AB247436, AB247435, AB247434, AB247433, AB247432, D42112, AB247430, and AB247431.

The polynucleotide can be evolutionarily stable. The evolutionarily stability of the polynucleotide can reduce or prevent unwanted replication of the viral vector in a subject. The evolutionary stability of the polynucleotide can vary depending on the embodiment. In some embodiments, the polynucleotide is not capable of being replicated when the stabilizing molecule is absent, the polynucleotide is not capable of being replicated when the protease inhibitor is present, and/or the polynucleotide is not capable of being replicated when the degron stabilizing molecule is absent, after 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, days of serial passaging. In some embodiments, after 50 days of serial passaging (a) the polynucleotide is not capable of being replicated when the stabilizing molecule is absent, (b) the polynucleotide is not capable of being replicated when the protease inhibitor is present, and/or (c) the polynucleotide is not capable of being replicated when the degron stabilizing molecule is absent. In some embodiments, after 300 days of serial passaging (a) the polynucleotide is not capable of being replicated when the stabilizing molecule is absent, (b) the polynucleotide is not capable of being replicated when the protease inhibitor is present and/or (c) the polynucleotide is not capable of being replicated when the degron stabilizing molecule is absent.

As used herein, the term "viral vector" shall be given its ordinary meaning and shall also refer to the virus at one or more, or all, of the stages of a viral life cycle, such as for example, single-stranded negative sense RNA, ribonucleo-protein complexes, and enveloped virus particles comprising ribonucleoprotein. In some embodiments, "viral vector" relates to virus-derived nucleic acid that can be transfected into cells and replicated within or independently of a cell genome, and includes whole viruses or viral particles, or viral cores consisting of viral genome and associated proteins.

As used herein, the terms "viral replication" and "virus replication" shall be given their ordinary meaning and shall also refer to one or more, or all, of the stages of a viral life cycle which result in the propagation of virus. The steps of a viral life cycle include, but are not limited to, virus attachment to the host cell surface, penetration or entry of the host cell (e.g., through receptor mediated endocytosis or membrane fusion), uncoating (the process whereby the viral capsid is removed and degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In some embodiments, the terms "viral replication" and "virus replication" refer to the replication of the viral genome. In some embodiments, the terms "viral replication" and "virus replication" refer to the synthesis of viral proteins.

Methods of propagating and isolating non-segmented negative-strand RNA viral vectors from viral vector-amplifying cells are known in the art. Such viral vector-amplifying cells can be prokaryotic cells or eukaryotic cells. The recovery of recombinant, non-segmented negative-stranded RNA viruses from cDNA can comprise a specialized rescue system, as introduction of viral genomic RNA into a cell by itself is not sufficient to initiate virus replication. Viral vector-amplifying cells can comprise a viral cDNA expression vector and/or expression vectors encoding N, P, and L. The nucleic acid encoding the viral genome (e.g., viral vector polynucleotide) can be operatively linked with a transcriptional signal and may further comprises a transcriptional terminator and a ribozyme sequence at the 3' end of the nucleic acid encoding the viral genome. The ribozyme sequence can allow for cleavage of the transcript at the 3' end of the viral sequence. In some embodiments, the nucleic acid encoding a genome or antigenome of the viral vector (e.g., viral vector polynucleotide) can be operably linked with an expression control sequence to direct synthesis of viral RNA transcripts from the cDNA expression vector in the viral vector-amplifying cells. In some embodiments, the viral cDNA expression vector can comprise a cDNA encoding the (+) strand full-length sequence (antigenome) of the viral vector. In some embodiments, in the viral cDNA expression vector, hammerhead and hepatitis delta virus ribozymes can flank the viral vector (e.g., rabies virus) antigenomic cDNA, enabling the production of authentic 5' and 3' ends of antigenomic viral RNA by transcription. The first ten nucleotides of the hammerhead sequence can be designed to be complementary to the first ten nucleotides of the antisense genomic sequence. The viral cDNA expression vector encoding a genome or antigenome of the viral vector can operably linked with an expression control sequence to direct synthesis of viral RNA transcripts from the cDNA expression vector in the viral vector-amplifying cells. Transcription of the viral cDNA expression vector can involve both cellular RNA dependent RNA polymerase II, which is available in mammalian cells, as well as exogenous phage (e.g., T7) RNA polymerase. The viral cDNA expression vector can be a transfected plasmid or can be integrated in the viral vector-amplifying cell genome. In some embodiments, viral vector-amplifying cells also comprise one or more trans-complementation vectors expressing an N protein, a P protein, and/or an L protein in trans (e.g., from a transiently transfected expression vector). The viral RNA that is a genomic or antigenomic equivalent can be packaged by the N protein and then can replicated by the P/L proteins. G protein, if absent from the viral vector polynucleotide, can be provided in trans by the viral vector-amplifying cells, thereby producing viral particles. In some embodiments, viral vector-amplifying cells are configured to express the (+) strand full-length sequence (antigenome), N protein, P protein, L protein, and/or phage RNA polymerase in response to one or more signals. Introduction of nucleic acids into viral vector-amplifying cells can be affected by any of a variety of methods known in the art, such as, for example, calcium phosphate transfection, DEAE-dextran mediated transfection, cationic lipid-mediated transfection, electroporation, electrical nuclear transport, chemical transduction, electrotransduction, and/or infection. In some embodiments, transfection facilitating reagent is added to increase DNA uptake by cells. Many of these reagents are known in the art, such as, for example, LIPOFECTACE, EFFECTENE, and any other cationic lipid that coats DNA and enhances DNA uptake by cells. In some embodiments lipid nanoparticle (LNP) compositions are employed to introduce nucleic acids into viral vector-amplifying cells.

Transgenes

Figure 1B:
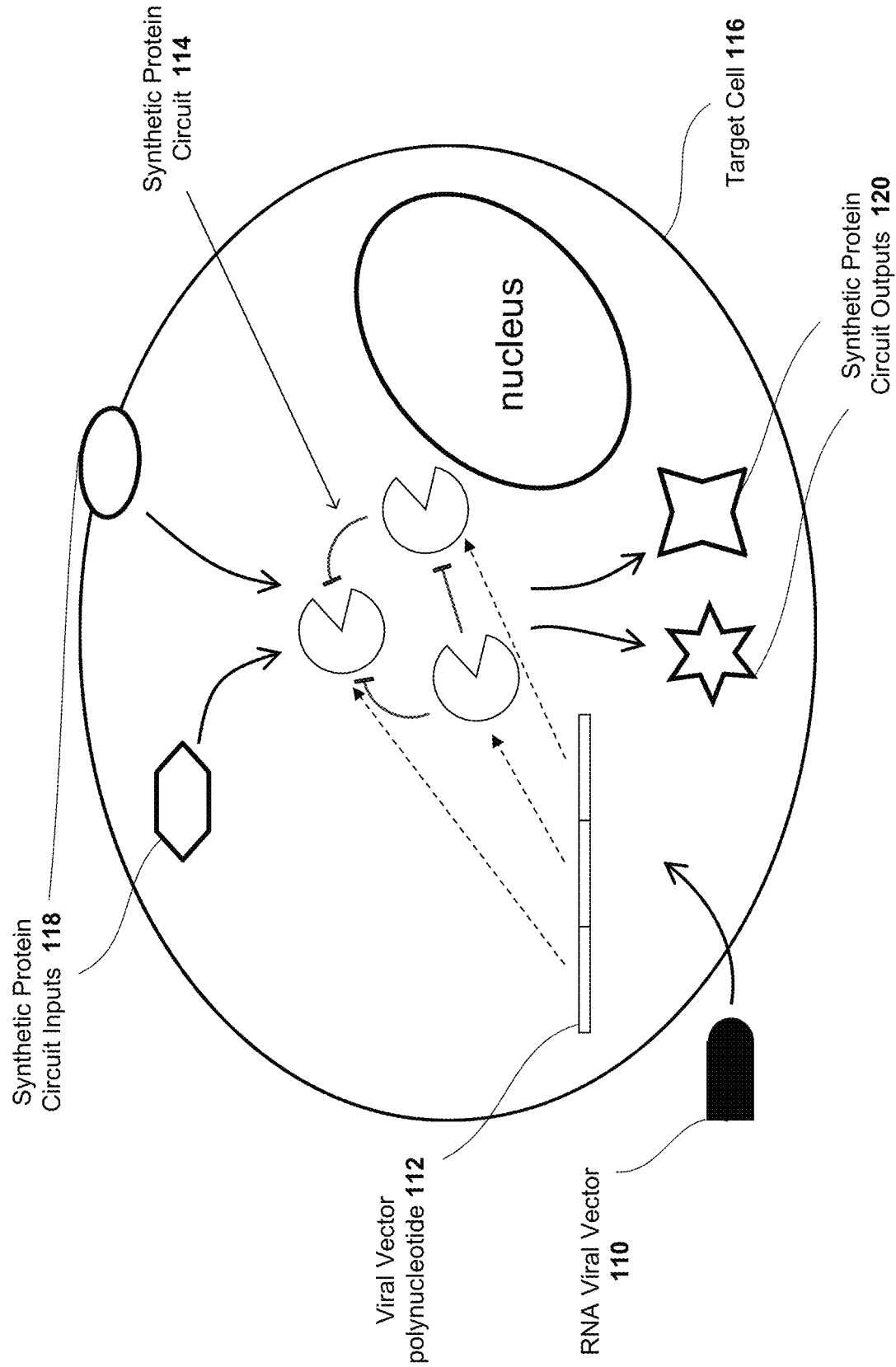
FIG. 1B is a schematic illustration showing a non-limiting exemplary embodiment of a viral vector delivering a polynucleotide encoding a synthetic protein circuit to a target cell.

Disclosed herein are viral vectors comprising a polynucleotide encoding one or more transgenes. As used herein, the term "transgene" shall be given its ordinary meaning and shall also refer to a nucleic acid derived from a source other than the RNA viral vector. As disclosed herein, the transgene is operatively linked with appropriate regulatory elements in some embodiments. The one or more transgenes of the viral vector can comprise a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof. The one or more transgenes of the viral vector can comprise cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof. The one or more transgenes of the viral vector can comprise one or more synthetic protein circuit components. The one or more transgenes of the viral vector can comprise can entire synthetic protein circuit comprising one or more synthetic protein circuit components. The one or more transgenes of the viral vector can comprise two or more synthetic protein circuits. Synthetic protein circuits have been described in, for example, Gao, Xiaojing J., et al. "Programmable protein circuits in living cells." *Science* 361.6408 (2018): 1252-1258; and PCT Application published as WO 2019/147478; the content of each of these, including any supporting or supplemental information or material, is incorporated herein by reference in its entirety. FIG. 1B is a schematic illustration showing a non-limiting exemplary embodiment of a viral vector delivering a polynucleotide encoding a synthetic protein circuit to a target cell. The RNA viral vector 110 can comprise viral vector polynucleotide 112. The viral vector polynucleotide can encode a synthetic protein circuit 114 comprising a plurality of synthetic protein circuit components. The synthetic protein circuit 114 can be expressed in target cell 116 following transduction by the RNA viral vector 110. The synthetic protein circuit 114 can respond to synthetic protein circuit inputs 118 and generate synthetic protein circuit outputs 120.

In some embodiments, the transgene encodes a protein of interest. As used herein, a "protein of interest" can be any protein, including naturally-occurring and non-naturally occurring proteins. Examples of protein of interest include, but are not limited to, luciferases; fluorescent proteins (e.g., GFP); growth hormones (GHs) and variants thereof; insulin-like growth factors (IGFs) and variants thereof granulocyte colony-stimulating factors (G-CSFs) and variants thereof; erythropoietin (EPO) and variants thereof insulin, such as proinsulin, preproinsulin, insulin, insulin analogs, and the like; antibodies and variants thereof, such as hybrid antibodies, chimeric antibodies, humanized antibodies, monoclonal antibodies; antigen binding fragments of an antibody (Fab fragments), single-chain variable fragments of an antibody (scFV fragments); dystrophin and variants thereof clotting factors and variants thereof; cystic fibrosis transmembrane conductance regulator (CFTR) and variants thereof and interferons and variants thereof.

In some embodiments, the protein of interest is a therapeutic protein or variant thereof. Non-limiting examples of therapeutic proteins include blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-a), transforming growth factor beta (TGF-β), and the like; soluble receptors, such as soluble TNF-receptors, soluble VEGF receptors, soluble interleukin receptors (e.g., soluble IL-1 receptors and soluble type II IL-1 receptors), soluble γ/δ T cell receptors, ligand-binding fragments of a soluble receptor, and the like; enzymes, such as— glucosidase, imiglucarase, β-glucocerebrosidase, and alglucerase; enzyme activators, such as tissue plasminogen activator; chemokines, such as IP-10, monokine induced by interferon-gamma (Mig), Gro/IL-8, RANTES, MIP-1, MIP-I β, MCP-1, PF-4, and the like; angiogenic agents, such as vascular endothelial growth factors (VEGFs, e.g., VEGF121, VEGF165, VEGF-C, VEGF-2), transforming growth factor-beta, basic fibroblast growth factor, glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LIF); transforming growth factors (TGFs); tissue factors, luteinizing hormone; macrophage activating factors; tumor necrosis factor (TNF); neutrophil chemotactic factor (NCF); nerve growth factor; tissue inhibitors of metalloproteinases; vasoactive intestinal peptide; angiogenin; angiotropin; fibrin; hirudin; IL-1 receptor antagonists; and the like.

Some other non-limiting examples of protein of interest include ciliary neurotrophic factor (CNTF); brain-derived neurotrophic factor (BDNF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin or mini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, β-enolase, and glycogen synthase; lysosomal enzymes (e.g., beta-N-acetylhexosaminidase A); and any variants thereof.

In some embodiments, the protein of interest is an active fragment of a protein, such as any of the aforementioned proteins. In some embodiments, the protein of interest is a fusion protein comprising some or all of two or more proteins. In some embodiments a fusion protein can comprise all or a portion of any of the aforementioned proteins.

In some embodiments, the viral vector comprises a polynucleotide comprising coding regions for two or more proteins of interest. The two or more proteins of interest can be the same or different from each other. In some embodiments, the two or more proteins of interest are related polypeptides, for example neutralizing antibodies for the same virus.

In some embodiments, the protein of interest is a multi-subunit protein. For examples, the protein of interest can comprise two or more subunits, or two or more independent polypeptide chains. In some embodiments, the protein of interest can be an antibody. Examples of antibodies include, but are not limited to, antibodies of various isotypes (for example, IgG1, IgG2, IgG3, IgG4, IgA, IgD, IgE, and IgM); monoclonal antibodies produced by any means known to those skilled in the art, including an antigen-binding fragment of a monoclonal antibody; humanized antibodies; chimeric antibodies; single-chain antibodies; antibody fragments such as Fv, F(ab')2, Fab', Fab, Facb, scFv and the like; provided that the antibody is capable of binding to antigen. In some embodiments, the antibody is a full-length antibody. In some embodiments, the protein of interest can be an antigen-binding moiety as disclosed herein.

In some embodiments, the transgene encodes a pro-survival protein (e.g., Bcl-2, Bcl-XL, Mcl-1 and A1). In some embodiments, the transgene encodes a apoptotic factor or apoptosis-related protein such as, for example, AIF, Apaf e.g. Apaf-1, Apaf-2, Apaf-3, oder APO-2 (L), APO-3 (L), Apopain, Bad, Bak, Bax, Bcl-2, Bcl-xL, Bcl-xs, bik, CAD, Calpain, Caspase e.g. Caspase-1, Caspase-2, Caspase-3, Caspase-4, Caspase-5, Caspase-6, Caspase-7, Caspase-8, Caspase-9, Caspase-10, Caspase-11, ced-3, ced-9, c-Jun, c-Myc, crm A, cytochrome C, CdR1, DcR1, DD, DED, DISC, DNA-PKcs, DR3, DR4, DR5, FADD/MORT-1, FAK, Fas (Fas-ligand CD95/fas (receptor)), FLICE/MACH, FLIP, fodrin, fos, G-Actin, Gas-2, gelsolin, granzyme A/B, ICAD, ICE, JNK, Lamin A/B, MAP, MCL-1, Mdm-2, MEKK-1, MORT-1, NEDD, NF-$_{kappa}$B, NuMa, p53, PAK-2, PARP, perforin, PITSLRE, PKCdelta, pRb, presenilin, prICE, RAIDD, Ras, RIP, sphingomyelinase, thymidinkinase from herpes simplex, TRADD, TRAF2, TRAIL-R1, TRAIL-R2, TRAIL-R3, and/or transglutaminase.

In some embodiments, the transgene encodes a cellular reprogramming factor capable of converting an at least partially differentiated cell to a less differentiated cell, such as, for example, Oct-3, Oct-4, Sox2, c-Myc, Klf4, Nanog, Lin28, ASCL1, MYT1 L, TBX3b, SV40 large T, hTERT, miR-291, miR-294, miR-295, or any combinations thereof. In some embodiments, the transgene encodes a programming factor that is capable of differentiating a given cell into a desired differentiated state, such as, for example, nerve growth factor (NGF), fibroblast growth factor (FGF), interleukin-6 (IL-6), bone morphogenic protein (BMP), neurogenin3 (Ngn3), pancreatic and duodenal homeobox 1 (Pdx1), Mafa, or any combination thereof.

In some embodiments, the transgene encodes a human adjuvant protein capable of eliciting an innate immune response, such as, for example, cytokines which induce or enhance an innate immune response, including IL-2, IL-12, IL-15, IL-18, IL-21CCL21, GM-CSF and TNF-alpha; cytokines which are released from macrophages, including IL-1, IL-6, IL-8, IL-12 and TNF-alpha; from components of the complement system including C1q, MBL, C1r, C1s, C2b, Bb, D, MASP-1, MASP-2, C4b, C3b, C5a, C3a, C4a, C5b, C6, C7, C8, C9, CR1, CR2, CR3, CR4, C1qR, C1INH, C4 bp, MCP, DAF, H, I, P and CD59; from proteins which are components of the signaling networks of the pattern recognition receptors including TLR and IL-1 R1, whereas the components are ligands of the pattern recognition receptors including IL-1 alpha, IL-1 beta, Beta-defensin, heat shock proteins, such as HSP10, HSP60, HSP65, HSP70, HSP75 and HSP90, gp96, Fibrinogen, Typ111 repeat extra domain A of fibronectin; the receptors, including IL-1 R1, TLR1, TLR2, TLR3, TLR4, TLR5, TLR6, TLR7, TLR8, TLR9, TLR10, TLR11; the signal transducers including components of the Small-GTPases signaling (RhoA, Ras, Racl, Cdc42 etc.), components of the PIP signaling (PI3K, Src-Kinases, etc.), components of the MyD88-dependent signaling (MyD88, IRAK1, IRAK2, etc.), components of the MyD88-independent signaling (TICAM1, TICAM2 etc.); activated transcription factors including e.g. NF-κB, c-Fos, c-Jun, c-Myc; and induced target genes including e.g. IL-1 alpha, IL-1 beta, Beta-Defensin, IL-6, IFN gamma, IFN alpha and IFN beta; from costimulatory molecules, including CD28 or CD40-ligand or PD1; protein domains, including LAMP; cell surface proteins; or human adjuvant proteins including CD80, CD81, CD86, trif, flt-3 ligand, thymopentin, Gp96 or fibronectin, etc., or any species homolog of any of the above human adjuvant proteins.

In some embodiments, the transgene encodes immunogenic material capable of stimulating an immune response (e.g., an adaptive immune response) such as, for example, antigenic peptides or proteins from a pathogen. The expression of the antigen may stimulate the body's adaptive immune system to provide an adaptive immune response. Thus, it is contemplated that some embodiments the viral vectors provided herein can be employed as vaccines for the prophylaxis or treatment of infectious diseases (e.g., as vaccines).

In some embodiments, the transgene is a nucleic acid which, upon administration of a prodrug, effects transition of a gene product to a compound which kills its host cell (e.g., a suicide gene). The some embodiments, the methods herein comprise a) delivering a polynucleotide comprising a suicide gene to a target cell of a subject in need thereof according to any of the embodiments provided herein and b) administering a prodrug to the subject. Any suitable suicide gene and prodrug is contemplated this disclosure, such as, for example, the suicide gene/prodrug combinations depicted in Table 1.

TABLE 1

| Suicide Gene | Prodrug(s) |
|---|---|
| HSV thymidine kinase (TK) | Ganciclovir (GCV); Ganciclovir elaidic acid ester; Penciclovir (PCV); Acyclovir (ACV); Valacyclovir (VCV); (E)-5-(2-bromovinyl)-2'-deoxyuridine (BVDU); Zidovuline (AZT); 2'-exo-methanocarbathymidine (MCT) |
| Cytosine Deaminase (CD) | 5-fluorocytosine (5-FC) |
| Purine nucleoside phosphorylase (PNP) | 6-methylpurine deoxyriboside (MEP); fludarabine (FAMP) |
| Cytochrome p450 enzymes (CYP) | Cyclophosphamide (CPA); Ifosfamide (IFO); 4-ipomeanol (4-IM) |
| Carboxypeptidases (CP) | 4-[(2-chloroethyl)(2-mesyloxyethyl)amino]benzoyl-L-glutamic acid (CMDA); Hydroxy-and amino-aniline mustards; Anthracycline glutamates; Methotrexate α-peptides (MTX-Phe) |
| Caspase-9 | AP1903 |
| Carboxylesterase (CE) | Irinotecan (IRT); Anthracycline acetals |
| Nitroreductase (NTR) | dinitroaziridinylbenzamide CB1954; dinitrobenzamide mustard SN23862; 4-Nitrobenzyl carbamates; Quinones |
| Horse radish peroxidase (HRP) | Indole-3-acetic acid (IAA); 5-Fluoroindole-3-acetic acid (FIAA) |
| Guanine Ribosyltransferase (XGRTP) | 6-Thioxanthine (6-TX) |
| Glycosidase enzymes | HM1826; Anthracycline acetals |
| Methionine-α,γ-lyase (MET) | Selenomethionine (SeMET) |
| Thymidine phosphorylase (TP) | 5'-Deoxy-5-fluorouridine (5'-DFU) |

In single-stranded negative RNA viruses, the 3'-distal sequences of the genome serve mainly as a transcription promoter, while the 5'-terminal sequences of the genome serve as a replication promoter. The RNA-dependent polymerase complex actuates and achieves transcription and replication by engaging cis-acting signals at the 3' end of the genome, in particular, the promoter region. Viral genes are then transcribed from the genome template unidirectionally from its 3' to its 5' end. For example, during transcription, the RNA-dependent RNA polymerase can sequentially synthesize five capped and polyadenylated mRNAs. There can be less mRNA made from the downstream genes (e.g., the polymerase gene (L)) relative to their upstream neighbors (e.g., the nucleoprotein gene (N)). This polarity gradient can reflect a localized transcriptional attenuation at each gene junction, where it has been approximated 30% of RdRP molecules fail to transcribe the downstream gene. Therefore, there can be a gradient of mRNA abundance according to the position of the genes relative to the 3'-end of the genome. The leader and trailer regions in RNA viruses (e.g. rabies virus) can also contain signals for viral transcription and replication. The inter-genic regions among leader-N, N-P, P-M, M-G, pseudo-gene region and G-L can serve as the signals for initiation of viral transcription. In some embodiments provided herein, the inter-genic regions, leader regions, and/or trailer regions of the viral vector are configured to tune viral transcription and/or replication.

Transgenes and regulatory elements can be inserted at various sites within the viral vector genome or antigenome, such as, for example, at a position 3' to N, between the N/P, P/M, and/or HN/L genes, or at another intergenic junction or non-coding region of a viral vector genome or antigenome. The one or more transgenes can be placed into the RNA viral genome in any suitable location, and in any order, to allow for expression of the one or more transgenes. In some embodiments, the presence of the one or more transgenes does not alter expression of the endogenous viral vector proteins (e.g., N, M, P, and/or L). In some embodiments, the expression level of the transgene can be modulated by inserting it at different sites in the viral vector polynucleotide (e.g., viral negative-strand RNA genome). For example, if high expression of a transgene is desired, the sequence is can be inserted into the 3' region of the viral negative-strand RNA genome, such as directly before the viral N gene. For example, if low expression of a transgene is desired, the sequence is can be inserted into the 5' region of the viral negative-strand RNA genome. In some embodiments, transgenes may be inserted as transcriptional cassettes. Several heterologous nucleic acid sequences may be inserted as independent transcriptional cassettes into the viral genome. A transcriptional cassette can comprise the nucleic acid sequence encoding the one or more transgenes operatively linked to a transcription start sequence, a transcriptional terminator, and/or translation signals.

In some embodiment, the viral vectors can include a regulatory sequence that allows, for example, the translation of multiple proteins from a single mRNA. Non-limiting examples of such regulatory sequences include internal ribosome entry site (IRES) and 2A self-processing sequence. In some embodiments, the 2A sequence is a 2A peptide site from foot-and-mouth disease virus (F2A sequence). In some embodiments, the F2A sequence has a standard furin cleavage site.

When it is desired to include coding regions for two or more proteins of interest, two or more individual polypeptide chains, or two or more subunits of a protein of interest in one viral vector, each additional coding region beyond the first is preferably linked to an element that facilitates co-expression of the proteins in host cells, such as an internal ribosomal entry sequence (IRES) element, or a 2A element. For example, IRES or 2A elements are preferably used when a single vector comprises sequences encoding each subunit of a multi-subunit protein. In the case of that the protein of interest is immunoglobulin with a desired specificity, for example, the first coding region (encoding either the heavy or light chain of immunoglobulin) is located downstream from the promoter. The second coding region (encoding the remaining chain of immunoglobulin) can be located downstream from the first coding region, and an IRES or 2A element can be disposed between the two coding regions, preferably immediately preceding the second coding region. The incorporation of an IRES or 2A element between the sequences of a first and second gene (encoding the heavy and light chains, respectively) can allow both chains to be expressed from the same promoter at about the same level in the cell.

The Kozak consensus sequence, Kozak consensus or Kozak sequence, is known as a sequence which occurs on eukaryotic mRA and has the consensus (gcc)gccRccAUGG, where R is a purine (adenine or guanine) three bases upstream of the start codon (AUG), which is followed by another "G." In some embodiments, the vector comprises a nucleotide sequence having at least about 70%, at least about 80%, at least about 90% sequence identity, or more to the Kozak consensus sequence. In some embodiments, the vector comprises a Kozak consensus sequence, e.g., after the polynucleotide encoding one or more proteins of interest is inserted into the vector (e.g., at the restrict site downstream of the promoter).

In some embodiments, the viral vector can also comprise regulatory control elements known to one of skill in the art to influence the expression of the RNA and/or protein products encoded by the polynucleotide within desired cells of the subject.

In some embodiments, functionally, expression of the polynucleotide is at least in part controllable by the operably linked regulatory elements such that the element(s) modulates transcription of the polynucleotide, transport, processing and stability of the RNA encoded by the polynucleotide and, as appropriate, translation of the transcript. A specific example of an expression control element is a promoter, which is usually located 5' of the transcribed sequence. Another example of an expression control element is an enhancer, which can be located 5' or 3' of the transcribed sequence, or within the transcribed sequence. Another example of a regulatory element is a recognition sequence for a microRNA. Another example of a regulatory element is an ration and the splice donor and splice acceptor sequences that regulate the splicing of said intron. Another example of a regulatory element is a transcription termination signal and/or a polyadenylation sequences.

Expression control elements and promoters include those active in a particular tissue or cell type, referred to herein as a "tissue-specific expression control elements/promoters." Tissue-specific expression control elements are typically active in specific cell or tissue (for example in the liver, brain, central nervous system, spinal cord, eye, retina, or lung). Expression control elements are typically active in these cells, tissues or organs because they are recognized by transcriptional activator proteins, or other regulators of transcription, that are unique to a specific cell, tissue or organ type.

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types; promoter/enhancer sequences from ubiquitously or promiscuously expressed mammalian genes including, but not limited to, beta actin, ubiquitin or EF1 alpha; or synthetic elements that are not present in nature, Expression control elements also can confer expression in a manner that is regulatable, that is, a signal or stimuli increases or decreases expression of the operably linked polynucleotide. A regulatable element that increases expression of the operably linked polynucleotide m response to a signal or stimuli is also referred to as an "inducible element" (that is, it is induced by a signal). Particular examples include, but are not limited to, a hormone (for example, steroid) inducible promoter. A regulatable element that decreases expression of the operably linked polynucleotide in response to a signal or stimuli is referred to as a "repressible element" (that is, the signal decreases expression such that when the signal, is removed or absent, expression is increased). Typically, the amount of increase or decrease conferred by such elements is proportional to the amount of signal or stimuli present: the greater the amount of signal or stimuli, the greater the increase or decrease in expression.

As described herein, the nucleotide sequence encoding the protein of interest can be modified to improve expression efficiency of the protein. The methods that can be used to improve the transcription and/or translation of a gene herein are not particularly limited. For example, the nucleotide sequence can be modified to better reflect host codon usage to increase gene expression (e.g., protein production) in the host (e.g., a mammal). As another non-limiting example for the modification, one or more of the splice donors and/or splice acceptors in the nucleotide sequence of the protein of interest is modified to reduce the potential for extraneous splicing.

The degree of transgene expression in the target cell can vary. For example, in some embodiments, the transgene encodes a protein of interest. The amount of the protein of interest expressed in the subject (e.g., the serum of the subject) can vary. For example, in some embodiments the protein can be expressed in the serum of the subject in the amount of at least about 9 μg/ml, at least about 10 μg/ml, at least about 50 μg/ml, at least about 100 μg/ml, at least about 200 μg/ml, at least about 300 μg/ml, at least about 400 μg/ml, at least about 500 μg/ml, at least about 600 μg/ml, at least about 700 μg/ml, at least about 800 μg/ml, at least about 900 μg/ml, or at least about 1000 μg/ml. In some embodiments, the protein of interest is expressed in the serum of the subject in the amount of about 9 μg/ml, about 10 μg/ml, about 50 μg/ml, about 100 μg/ml, about 200 μg/ml, about 300 μg/ml, about 400 μg/ml, about 500 μg/ml, about 600 μg/ml, about 700 μg/ml, about 800 μg/ml, about 900 μg/ml, about 1000 μg/ml, about 1500 μg/ml, about 2000 μg/ml, about 2500 μg/ml, or a range between any two of these values. A skilled artisan will understand that the expression level in which a protein of interest is needed for the method to be effective can vary depending on non-limiting factors such as the particular protein of interest and the subject receiving the treatment, and an effective amount of the protein can be readily determined by a skilled artisan using conventional methods known in the art without undue experimentation.

A protein of interest encoded by a transgene can be of various lengths. For example, the protein of interest can be at least about 200 amino acids, at least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer in length. In some embodiments, the protein of interest is at least about 480 amino acids in length. In some embodiments, the protein of interest is at least about 500 amino acids in length. In some embodiments, the protein of interest is about 750 amino acids in length.

The transgenes can have different lengths in different implementations. The number of transgenes in a viral vector polynucleotide can be different in different embodiments. In some embodiments, the number of transgenes in a viral vector polynucleotide can be, or can be about, 1, 2, 3, 4, 5, 6, 7, 8, 9, 10, 11, 12, 13, 14, 15, 16, 17, 18, 19, 20, 21, 22, 23, 24, 25, or a number or a range between any two of these values. In some embodiments, the number of transgenes in a viral vector polynucleotide can be at least, or can be at most, 1, 2, 3, 4, 5, 6, 7, 8, 9, 10, 11, 12, 13, 14, 15, 16, 17, 18, 19, 20, 21, 22, 23, 24, 25. In some embodiments, a transgenes is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3250, 3500, 3750, 4000, 4250, 4500, 4750, 5000, 5500, 6000, 6500, 7000, 7500, 8000, 8500, 9000, 9500, 10000, or a number or a range between any two of these values, nucleotides in length. In some embodiments, a transgene is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3250, 3500, 3750, 4000, 4250, 4500, 4750, 5000, 5500, 6000, 6500, 7000, 7500, 8000, 8500, 9000, 9500, or 10000 nucleotides in length.

A skilled artisan will appreciate the one or more of the viral vectors and sender cells can be used together in the applications described herein. For example, viral vectors expressing different transgenes of interest (e.g., different synthetic protein circuit components) can be administered to the same subject for diagnostic and/or therapeutic purposes. In some embodiments, the viral vectors are co-administered to the subject. In some embodiments, the viral vectors are administered to the subject separately. In some embodiments, a first viral vector expressing a first transgene and a second viral vector expressing a second transgene can be administered to the subject together or separately, wherein the first transgene and the second transgene can be the same or different. In some embodiments, the first transgene encodes a synthetic protein circuit component and the second transgene encodes a different protein circuit component. In some embodiments, the first transgene encodes a first protein of interest and the second transgene encodes a different protein of interest. In some embodiments, a first viral vector expressing a first set of transgenes and a second viral vector expressing a second set of transgenes can be administered to the subject together or separately, wherein the first transgene and the second transgene can be the same or different. In some embodiments, the first set of transgenes encodes a synthetic protein circuit and the second set of transgenes encodes a different protein circuit. In some embodiments, a first viral vector expressing a first subunit of the protein of interest and a second viral vector expressing a second subunit of the protein of interest can be administered to the subject together or separately.

Antigen-Binding Moieties

There are provided, in some embodiments, antigen-binding moieties. In some embodiments, there are provided conditionally stable proteins comprising an antigen-binding moiety. There are provided, in some embodiments, bridge proteins comprising an antigen-binding moiety. In some embodiments, the antigen-binding moiety can comprises a nanobody, Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof. In some embodiments, the antigen-binding moiety comprises an RNA aptamer, adNectin, iMab, anticalin, microbody, peptide aptamer, designed ankyrin repeat protein (DARPin), affilin, tetranectin, avimer, affibody, Kunitz domain, or any combination thereof.

Antigen-binding moieties can comprise antibodies, antibody fragments, and variants. In some embodiments, antibody fragments and variants may comprise antigen binding regions from intact antibodies. Examples of antibody fragments and variants may include, but are not limited to Fab, Fab', F(ab')2, and Fv fragments; diabodies; linear antibodies; single-chain antibody molecules such as single chain variable fragment (scFv); and multi specific antibodies formed from antibody fragments.

For the purposes herein, an "antibody" may comprise a heavy and light variable domain as well as an Fc region. As used herein, the term "native antibody" usually refers to a heterotetrameric glycoprotein of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end: the constant domain of the light chain is aligned with the first constant domain of the heavy chain, and the light chain variable domain is aligned with the variable domain of the heavy chain.

As used herein, the term "variable domain" refers to specific antibody domains found on both the antibody heavy and light chains that differ extensively in sequence among antibodies and are used in the binding and specificity of each particular antibody for its particular antigen. Variable domains comprise hypervariable regions. As used herein, the term "hypervariable region" refers to a region within a variable domain comprising amino acid residues responsible for antigen binding. The amino acids present within the hypervariable regions determine the structure of the complementarity determining regions (CDRs) that become part of the antigen-binding site of the antibody. As used herein, the term "CDR" refers to a region of an antibody comprising a structure that is complimentary to its target antigen or epitope. Other portions of the variable domain, not interacting with the antigen, are referred to as framework (FVV) regions. The antigen-binding site (also known as the antigen combining site or paratope) comprises the amino acid residues necessary to interact with a particular antigen. The exact residues making up the antigen-binding site are typically elucidated by co-crystallography with bound antigen, however computational assessments based on comparisons with other antibodies can also be used. Determining residues that make up CDRs may include the use of numbering schemes including, but not limited to, those taught by Kabai, Chothia, and Honegger.

H and VL domains have three CDRs each. VL CDRs are referred to herein as CDR-L1, CDR-L2 and CDR-L3, in order of occurrence when moving from N- to C-terminus along the variable domain polypeptide. VH CDRs are referred to herein as CDR-H1, CDR-H2 and CDR-H3, in order of occurrence when moving from N- to C-terminus along the variable domain polypeptide. Each of CDRs has favored canonical structures with the exception of the CDR-H3, which comprises amino acid sequences that may be highly variable in sequence and length between antibodies resulting in a variety of three-dimensional structures in antigen-binding domains. In some cases, CDR-H3s may be analyzed among a panel of related antibodies to assess antibody diversity. Various methods of determining CDR sequences are known in the art and may be applied to known antibody sequences.

As used herein, the term "Fv" refers to an antibody fragment comprising the minimum fragment on an antibody needed to form a complete antigen-binding site. These regions consist of a dimer of one heavy chain and one light chain variable domain in tight, non-covalent association. Fv fragments can be generated by proteolytic cleavage, but are largely unstable. Recombinant methods are known in the art for generating stable Fv fragments, typically through insertion of a flexible linker between the light chain variable domain and the heavy chain variable domain (to form a single chain Fv (scFv)) or through the introduction of a disulfide bridge between heavy and light chain variable domains.

As used herein, the term "light chain" refers to a component of an antibody from any vertebrate species assigned to one of two clearly distinct types, called kappa and lambda based on amino acid sequences of constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2.

As used herein, the term "single chain Fv" or "scFv" refers to a fusion protein of VH and VL antibody domains, wherein these domains are linked together into a single polypeptide chain by a flexible peptide linker. In some embodiments, the Fv polypeptide linker enables the scFv to form the desired structure for antigen binding. In some embodiments, scFvs are utilized in conjunction with phage display, yeast display or other display methods where they may be expressed in association with a surface member (e.g. phage coat protein) and used in the identification of high affinity peptides for a given antigen. Using molecular genetics, two scFvs can be engineered in tandem into a single polypeptide, separated by a linker domain, called a "tandem scFv" (tascFv). Construction of a tascFv with genes for two different scFvs yields a "bispecific single-chain variable fragments" (bis-scFvs).

As used herein, the term "bispecific antibody" refers to an antibody capable of binding two different antigens. Such antibodies typically comprise regions from at least two different antibodies. As used herein, the term "diabody" refers to a small antibody fragment with two antigen-binding sites. Diabodies are functional bispecific single-chain antibodies (bscAb). Diabodies comprise a heavy chain variable domain VH connected to a light chain variable domain VL in the same polypeptide chain. By using a linker that is too short to allow pairing between the two domains on the same chain, the domains are forced to pair with the complementary domains of another chain and create two antigen-binding sites.

The term "intrabody" can refer to a form of antibody that is not secreted from a cell in which it is produced, but instead targets one or more intracellular proteins. Intrabodies may be used to affect a multitude of cellular processes including, but not limited to intracellular trafficking, transcription, translation, metabolic processes, proliferative signaling and cell division. In some embodiments, methods of the present invention may include intrabody-based therapies. In some such embodiments, variable domain sequences and/or CDR sequences disclosed herein may be incorporated into one or more constructs for intrabody-based therapy.

As used herein, the term "monoclonal antibody" refers to an antibody obtained from a population of substantially homogeneous cells (or clones), i.e., the individual antibodies comprising the population are identical and/or bind the same epitope, except for possible variants that may arise during production of the monoclonal antibodies, such variants generally being present in minor amounts. In contrast to polyclonal antibody preparations that typically include different antibodies directed against different determinants (epitopes), each monoclonal antibody is directed against a single determinant on the antigen.

The modifier "monoclonal" can indicate the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

As used herein, the term "humanized antibody" refers to a chimeric antibody comprising a minimal portion from one or more non-human (e.g., murine) antibody source(s) with the remainder derived from one or more human immunoglobulin sources. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and/or capacity. In one embodiment, the antibody may be a humanized full-length antibody.

As used herein, the term "antibody variant" refers to a modified antibody (in relation to a native or starting antibody) or a biomolecule resembling a native or starting antibody in structure and/or function (e.g., an antibody mimetic). Antibody variants may be altered in their amino acid sequence, composition or structure as compared to a native antibody. Antibody variants may include, but are not limited to, antibodies with altered isotypes (e.g., IgA, IgD, IgE, IgG1, IgG2, IgG3, IgG4, or IgM), humanized variants, optimized variants, multi-specific antibody variants (e.g., bispecific variants), and antibody fragments.

In some embodiments, the antigen-binding moieties provided herein comprise antibody mimetics (e.g., monobodies). As used herein, the term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (U.S. Pat. Nos. 6,673,901; 6,348,584). In some embodiments, antibody mimetics may be those known in the art including, but are not limited to affibody molecules, affilins, affitins, anticalins, avimers, Centyrins, DARPINS™, Fynomers and Kunitz and domain peptides. In some embodiments, antibody mimetics may include one or more non-peptide regions.

In some embodiments, the antigen-binding moieties provided herein comprise multispecific antibodies that bind more than one epitope. As used herein, the terms "multi-body" or "multispecific antibody" refer to an antibody wherein two or more variable regions bind to different epitopes. The epitopes may be on the same or different targets. In some embodiments, a multi-specific antibody is a "bispecific antibody" which recognizes two different epitopes on the same or different antigens. In one aspect, bispecific antibodies are capable of binding two different antigens. Such antibodies typically comprise antigen-binding regions from at least two different antibodies. For example, a bispecific monoclonal antibody (BsMAb, BsAb) is an artificial protein composed of fragments of two different monoclonal antibodies, thus allowing the BsAb to bind to two different types of antigen. New generations of BsMAb, called "trifunctional bispecific" antibodies, have been developed. These consist of two heavy and two light chains, one each from two different antibodies, where the two Fab regions (the arms) are directed against two antigens, and the Fc region (the foot) comprises the two heavy chains and forms the third binding site.

In some embodiments, the antigen-binding moieties provided herein comprise antibodies comprising a single antigen-binding domain (e.g., nanobodies). These molecules are extremely small, with molecular weights approximately one-tenth of those observed for full-sized mAbs. Further antibodies may include "nanobodies" derived from the antigen-binding variable heavy chain regions (VHHs) of heavy chain antibodies found m camels and llamas, which lack light chains (Nelson, A. L., MAbs. 2010. Jan.-Feb.; 2(1): 77-83).

In some embodiments, the antibody may be "miniaturized". Among the best examples of mAb miniaturization are the small modular immunopharmaceuticals (SMIPs) from Trubion Pharmaceuticals. These molecules, which can be monovalent or bivalent, are recombinant single-chain molecules containing one VL, one VH antigen-binding domain, and one or two constant "effector" domains, all connected by linker domains. One example of miniaturized antibodies is called "unibody" in which the hinge region has been removed from IgG4 molecules. While IgG4 molecules are unstable and can exchange light-heavy chain heterodimers with one another, deletion of the hinge region prevents heavy chain-heavy chain pairing entirely, leaving highly specific monovalent light/heavy heterodimers, while retaining the Fc region to ensure stability and half-life in vivo.

In some embodiments, the antigen-binding moieties provided herein comprise single-domain antibodies (sdAbs, or nanobodies) which are antibody fragment consisting of a single monomelic variable antibody domain. In some embodiments, it is able to bind selectively to a specific antigen (e.g., like a whole antibody). In one aspect, a sdAb may be a "Camel Ig or "camelid VHH". As used herein, the term "camel Ig" refers to the smallest known antigen-binding unit of a heavy chain antibody (Koch-No lte, et al, FASEB J., 2007, 21: 3490-3498). A "heavy chain antibody" or a "camelid antibody" refers to an antibody that contains two VH domains and no light chains (Riechmann L. et al, J. Immunol. Methods, 1999, 231: 25-38; international patent publication NOs. WO 1994/04678 and WO 1994/025591; and U.S. Pat. No. 6,005,079). In another aspect, a sdAb may be a "immunoglobulin new antigen receptor" (IgNAR). As used herein, the term "immunoglobulin new antigen receptor" refers to class of antibodies from the shark immune repertoire that consist of homodimers of one variable new antigen receptor (VNAR) domain and five constant new antigen receptor (CNAR) domains. IgNARs represent some of the smallest known immunoglobulin-based protein scaffolds and are highly stable and possess efficient binding characteristics. The inherent stability can be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulphide bridges, and patterns of intra-loop hydrogen bonds.

In some embodiments, the antigen-binding moieties provided herein comprise intrabodies. Intrabodies are a form of antibody that is not secreted from a cell in which it is produced, but instead targets one or more intracellular proteins. Intrabodies are expressed and function intracellularly, and may be used to affect a multitude of cellular processes including, but not limited to intracellular trafficking, transcription, translation, metabolic processes, proliferative signaling and cell division. Sequences from donor antibodies may be used to develop intrabodies. Intrabodies are often recombinantly expressed as single domain fragments such as isolated VH and VL domains or as a single chain variable fragment (scFv) antibody within the cell. For example, intrabodies are often expressed as a single polypeptide to form, a single chain antibody comprising the variable domains of the heavy and light chains joined by a flexible linker polypeptide, intrabodies typically lack disulfide bonds and are capable of modulating the expression or activity of target genes through their specific binding activity. Single chain intrabodies are often expressed from a recombinant nucleic acid molecule and engineered to be retained intracellularly (e.g., retained in the cytoplasm, endoplasmic reticulum, or periplasm).

Bridge Proteins

There are provided, in some embodiments, bridge proteins. In some embodiments, the bridge protein comprises a glycoprotein binding domain capable of binding the glycoprotein. In some embodiments, the glycoprotein binding domain binds the glycoprotein. In some embodiments, a bridge protein comprises an antigen-binding moiety. The antigen-binding moiety can be capable of binding an antigen on a surface of a target cell. The antigen-binding moiety can be any antibody-binding moiety disclosed herein, such as, for example, a nanobody, Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), an RNA aptamer, adNectin, iMab, anticalin, microbody, peptide aptamer, designed ankyrin repeat protein (DARPin), affilin, tetranectin, avimer, affibody, Kunitz domain, or any combination thereof. In some embodiments, the viral vector is capable of transducing the target cell when the antigen-binding moiety is bound to the target cell antigen and the glycoprotein binding domain is bound to the glycoprotein and a receptor on the cell surface of the target cell. A viral vector transducing a target cell can comprise internalization of the viral vector by the target cell. The glycoprotein can comprise EnvA, EnvB, EnvC, EnvD, EnvE, EnvJ, a portion thereof, or any combination thereof. The glycoprotein can comprise all or a portion of avian sarcoma virus Env and/or an leukosis virus Env of any one of viral subgroups A-J. The glycoprotein binding domain can comprise all or a portion of a receptor of an avian sarcoma virus Env and/or an leukosis virus Env of any one of viral subgroups A-J. The glycoprotein binding domain can comprise TVA, TVB, TVC, or a portion thereof. The glycoprotein binding domain can be configured to bind EnvA, EnvB, EnvC, EnvD, EnvE, EnvJ, or a portion thereof. The glycoprotein can be capable of mediating internalization of the viral vector by the target cell. In some embodiments, the glycoprotein mediates internalization of the viral vector by the target cell. In some embodiments, the target cell is not capable of releasing the viral vector.

There are provided, in some embodiments, two or more bridge proteins (e.g., a first bridge protein and a second bridge protein). The two or more bridge proteins can comprise different antigen-binding moieties and different glycoprotein binding domains. The two or more bridge proteins can comprise the same antigen-binding moiety and different glycoprotein binding domains. The bridge protein can be configured to be stable in a host (e.g. a human host). In some embodiments, the bridge protein is configured to be non-immunogenic. In some embodiments, the bridge protein is non-immunogenic. The two or more bridge proteins can comprise different antigen-binding moieties and the same glycoprotein binding domain. For example, a first bridge protein can bind a first antigen on a surface of a target cell and a second bridge protein comprising a different antigen-binding moiety can bind a second antigen on a surface of a target cell. The first antigen and the second antigen can be the same or different. The first target antigen and/or a second antigen can be present on a target cell. In some embodiments, the first target antigen and/or second antigen is not present on a non-target cell.

In some embodiments, the target cell can comprise a cell associated with a disease or disorder. The target cell can comprise a tumor cell and/or an infected cell. The first target antigen and/or second target antigen can comprise a microbial antigen. The first target antigen and/or second target antigen can comprise a tumor-associated antigen or a tumor-specific antigen. The first target antigen and/or second target antigen can comprise platelet derived growth factor receptor alpha (PDGFRa), activin a receptor type 1 (ACVR1), human epidermal growth factor receptor 2 (Her2), prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, an abnormal p53 protein, mesothelin, EGFRvIII, EGFR1, diganglioside GD2, interleukin 13 receptor a (IL13Ra), fibroblast activation protein (FAP), LI cell adhesion molecule (L1 CAM), or any combination thereof.

In some embodiments, the antigen-binding moiety specifically binds to an antigen associated with fibrotic or inflammatory disease, such as, for example, Cadherin 11, PDPN, LRRC15, Integrin α4β7, Integrin α2β1, MADCAM, Nephrin, Podocin, IFNAR1, BDCA2, CD30, c-KIT, FAP, CD73, CD38, PDGFRp, Integrin αvβί, Integrin αvβ3, Integrin αvβ8, GARP, Endosialin, CTGF, Integrin αvβό, CD40, PD-1, TFM-3, TNFR2, DEC205, DCIR, CD86, CD45RB, CD45RO, MHC Class II, CD25, LRRC15, MMP14, GPX8, F2RL2, or any combination thereof. In some embodiments, the antigen-binding moiety specifically binds to an antigen specific for neuronal disorders, such as, for example, beta amyloid or MABT5102A. In some embodiments, the antigen-binding moiety specifically binds to an antigen specific for diabetes, such as, for example, IL-1β or CD3. In some embodiments, the antigen-binding moiety specifically binds to an antigen specific for cardiovascular diseases, such as, for example, C5, cardiac myosin, CD41 (integrin α-IIb), fibrin II, beta chain, ITGB2 (CD18) and sphingosine-1-phosphate. In some embodiments, the antigen-binding moiety specifically binds to an antigen specific for senescent cells, such as, for example, DEP1, NTAL, EBP50, STX4, VAMP3, ARMX3, B2MG, LANCL1, VPS26A, or PLD3.

In some embodiments, the antigen-binding moiety specifically binds to an tumor antigen. A tumor antigen can be a tumor specific antigen and/or a tumor associated antigen. As described herein, a "tumor antigen" refers to a molecular marker that can be expressed on a neoplastic tumor cell and/or within a tumor microenvironment. The molecular marker can be a cell surface receptor. For example, a tumor antigen can be an antigen expressed on a cell associated with a tumor, such as a neoplastic cell, stromal cell, endothelial cell, fibroblast, or tumor-infiltrating immune cell. For example, the tumor antigen Her2/Neu can be overexpressed by certain types of breast and ovarian cancer. A tumor antigen can also be ectopically expressed by a tumor and contribute to deregulation of the cell cycle, reduced apoptosis, metastasis, and/or escape from immune surveillance. Tumor antigens are generally proteins or polypeptides derived therefrom, but can be glycans, lipids, or other small organic molecules. Additionally, a tumor antigen can arise through increases or decreases in post-translational processing exhibited by a cancer cell compared to a normal cell, for example, protein glycosylation, protein lipidation, protein phosphorylation, or protein acetylation. Non-limiting examples of tumor antigens bound by antigen-binding moieties provided herein include 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R171, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1; MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class 1/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGF, VEGFR-2/FLK-1, WT1, and any combination thereof.

In some embodiments, the antigen-binding moiety specifically binds to an antigen that is prominently expressed and/or present on DCs (i.e., a DC marker). Exemplary DC markers include, but are not limited to, CD1a (R4, T6, HTA-1); CD1b (R1); CD1c (M241, R7); CD1d (R3); CD1e (R2); CD11b (αM Integrin chain, CR3, Mol, C3niR, Mac-1); CD11 c (αX Integrin, p150, 95, AXb2); CDw117 (Lactosylceramide, LacCer); CD19 (B4); CD33 (gp67); CD 35 (CR1, C3b/C4b receptor); CD 36 (GpIIIb, GPIV, PASIV); CD39 (ATPdehydrogenase, NTPdehydrogenase-1); CD40 (Bp50); CD45 (LCA, T200, B220, Ly5); CD45RA; CD45RB; CD45RC; CD45RO (UCHL-1); CD49d (VLA-4α, α4 Integrin); CD49e (VLA-5α, α5 Integrin); CD58 (LFA-3); CD64 (FcγRI); CD72 (Ly-19.2, Ly-32.2, Lyb-2); CD73 (Ecto-5' nucloticlase); CD74 (Ii, invariant chain); CD80 (B7, B7-1, BB1); CD81 (TAPA-1); CD83 (HB 15); CD85a (ILT5, LIR3, HL9); CD85d (ILT4, LIR2, MIR10); CD85j (ILT2, LIR1, MIR7); CD85k (ILT3, LIRS, HM18); CD86 (B7-2/B70); CD88 (C5aB); CD97 (BL-KDD/F12); CD101 (IGSF2, P126, V7); CD116 (GM-CSFRα); CD120a (TMFRI, p55); CD120b (TNFRII, p'75, TNFR p80); CD123 (IL-3Rα); CD139; CD148 (HPTP-η, p260, DEP-1); CD150 (SLAM, IPO-3); CD156b (TACE, ADAM17, cSVP); CD157 (Mo5, BST-1); CD167a (DDR1, trkE, cak); CD168 (RHAMM, IHABP, HMMR); CD169 (Sialoadhesin, Siglec-1); CD170 (Siglec-5); CD171 (L1CAM, NILE); CD172 (SIRP-1α, MyD-1); CD172b (SIRPβ); CD180 (RP105, Bgp95, Ly64); CD184 (CXCR4, NPY3R); CD193 (CCR3); CD196 (CCR6); CD197 (CCR7 (ws CDw197)); CDw197 (CCR7, EBI1, BLR2); CD200 (OX2); CD205 (DEC-205); CD206 (MMR); CD207 (Langerin); CD208 (DC-LAMP); CD209 (DC-SIGN); CDw218a (IL18Rα); CDw218b (IL8Rβ); CD227 (MUC1, PUM, PEM, EMA); CD230 (Prion Protein (PrP)); CD252 (OX40L, TNF (ligand) superfamily, member 4); CD258 (LIGHT, TNF (ligand) superfamily, member 14); CD265 (TRANCE-R, TNF-R superfamily, member 11a); CD271 (NGFR, p'75, TNFR superfamily, member 16); CD273 (B7DC, PDL2); CD274 (B7H1, PDL1); CD275 (B7H2, ICOSL); CD276 (B7H3); CD277 (BT3.1, B7 family: Butyrophilin 3); CD283 (TLR3, TOLL-like receptor 3); CD289 (TLR9, TOLL-like receptor 9); CD295 (LEPR); CD298 (ATP1B3, Na K ATPase β3 submit); CD300a (CMRF-35H); CD300c (CMRF-35A); CD301 (MGL1, CLECSF14); CD302 (DCL1); CD303 (BDCA2); CD304 (BDCA4); CD312 (EMR2); CD317 (BST2); CD319 (CRACC, SLAMF7); CD320 (8D6); and CD68 (gp110, Macrosialin); class II MEW; BDCA-1; and/or Siglec-H.

In some embodiments, the antigen-binding moiety specifically binds to an antigen that is prominently expressed and/or present on T cells (i.e., a T cell marker). Exemplary T cell markers include, but are not limited to, CD2 (E-rosette R, T11, LFA-2); CD3 (T3); CD3 α; CD3 β; CD3ε; CD4 (L3T4, W3/25, T4); CD5 (T1, Tp67, Leu-1, LY-1); CD6 (T12); CD7 (gp40, Leu 9); CD8a (Leu2, T8, Lyt-2, 3); CD8b (CD8, Leu2, Lyt3); CD11a (LFA-1α, α Integrin chain); CD11b (αM Integrin chain, CR3, Mol, C3niR, Mac-1); CD11c (αX Integrin, p150, 95, AXb2); CD15s (Sialyl Lewis X); CD15u (3' sulpho Lewis X); CD15su (6 sulpho-sialyl Lewis X); CD16b (FcgRIIIb); CDw17 (Lactosylceramide, LacCer); CD18 (Integrin β2 CD11a, b, c β-subunit); CD26 (DPP IV ectoeneyme, ADA binding protein); CD27 (T14, S152); CD28 (Tp44, T44); CD29 (Platelet GPIIa, β-1 integrin, GP); CD31 (PECAM-1, Endocam); CD35 (CR1, C3b/C4b receptor); CD37 (gp52-40); CD38 (ADP-ribosyl/cyclase, T10); CD43 (Sialophorin, Leukosialin); CD44 (ECMRII, H-CAM, Pgp-1); CD45 (LCA, T200, B220, Ly5); CD45RA (p561ck, p59fyn, Src kinases); CD45RB (p561ck, p59fyn, Src kinases); CD45RC (p561ck, p59fyn, Src kinases); CD46 (MCP); CD47 (gp42, IAP, OA3, Neurophillin); CD47R (MEM-133); CD48 (Blast-1, Hulym3, BCM-1, OX-45); CD49c (VLA-3α, α3 Integrin); CD49d (VLA-4α, α4 Integrin); CD49e (VLA-5α, α5 Integrin); CD49f (VLA-6α, α6 Integrin gplc); CD50 (ICAM-3); CD52 (CAMPATH-1, HES); CD53 (OX-44); CD54 (ICAM-1); CD55 (DAF); CD56 (Leu-19, NKH-1, NCAM); CD57 (HNK1, Leu-7); CD58 (LFA-3); CD59 (1F5Ag, H19, Protectin, MACIF, MIRL, P-18); CD60a (GD3); CD60b (9-O-acetyl GD3); CD60c (7-0 acetyl GD3); CD62L (L-selectin, LAM-1, LECAM-1, MEL-14, Leu8, TQ1); CD73 (Ecto-5'-nucleotidase); CD75 (sialo-masked Lactosamine); CD75S (α2, 6 sialylated Lactosamine); CD81 (TAPA-1); CD82 (4F9, C33, IA-4, KAI1, R2); CD84 (P75, GR6); CD85a (ILT5, LIR3, HL9); CD85j (ILT2, LIR1, MIR7); CD87 (uPAR); CDw92 (p70); CD94 (Kp43); CD95 (APO-1, FAS, TNFRSF6); CD98 (4F2, FRP-1, RL-388); CD99 (MIC2, E2); CD99R (CD99 Mab restricted); CD100 (SEMA4D); CD102 (ICAM-2); CD108 (SEMA7A, JMH blood group antigen); CDw119 (IFNγR, IFNγRa); CD120a (TNFRI, p55); CD120b (TNFRII, p75, TNFR p80); CD121a (Type 1 IL-1R); CD121b (Type 2 IL-1R); CD122 (IL2Rβ); CD124 (IL-4Rα); CD126 (IL-6Rα); CD127 (p90, IL-7R, IL-7Rα); CD128a (IL-8Ra, CXCR1, (Tentatively renamed as CD181)); CD128b (IL-8Rb, CXCR2, (Tentatively renamed as CD182)); CD130 (gp130); CD132 (Common γ chain, IL-2Rγ); CD147 (Basigin, EMMPRIN, M6, OX47); CD148 (HPTP-η, p260, DEP-1); CD150 (SLAM, IPO-3); CD153 (CD3OL, TNSF8); CD156b (TACE, ADAM17, cSVP); CD158a (KIR2DL1, p58.1); CD158b1 (KIR2DL2, p58.2); CD158b2 (KIR2DL3, p58.3); CD158c (KIR2DS6, KIRX); CD158le1/e2 (KIR3DLI/S1, p'70); CD159F (KIR2DL5); CD158g (KIR2DS5); CD158h (KIR2DS1, p50.1); CD158i (KIR2DS4, p50.3); CD158j (KIR2DS2, p50.2); CCD158k (KIR3DL2, p140); CD159a (NKG2A); CD160 (BY55, NK1, NK28); CD161 (NKR, NKRP1A); CD162 (PSGL-1); CD164 (MGC-24, MUC-24); CD171 (L1CAM, NILE); CD172g (SIRPg); CD181 (CXCR1, (Formerly known as CD128a)); CD182 (CXCR2, (Formerly known as CD128b)); CD183 (CXCR3, GPR9); CD184 (CXCR4, NPY3R); CD185 (CXCR5); CD186 (CXCR6); CD191 (CCR1); CD192 (CCR2); CD193 (CCR3); CD195 (CCR5); CD196 (CCR6); CD197 (CCR7 (was CDw197)); CDw197 (CCR7, EBI1, BLR2); CDw198 (CCR8); CDw199 (CCR9); CD205 (DEC-205); CDw210 (CK); CDw217 (CK); CDw218a (IL18Rα); CDw218b (IL18Rβ); CD220 (Insulin R); CD221 (IGF1 R); CD222 (M6P-R, IGFII-R); CD223 (LAG-3); CD224 (GGT); CD225 (Leu13); CD226 (DNAM-1, PTA1); CD229 (Ly9); CD230 (Prion Protein (PrP));

CD244 (2B4, P38, NAIL); CD245 (p220/240); CD247 (CD3 Zeta Chain); CD261 (TRAIL-R1, TNF-R superfamily, member 10a); CD262 (TRAIL-R2, TNF-R superfamily, member 10b); CD263 (TRAIL-R3, TNF-R superfamily, member 10c); CD264 (TRAIL-R4, TNF-R superfamily, member 10d); CD265 (TRANCE-R, TNF-R superfamily, member 11a); CD268 (BAFFR, TNF-R superfamily, member 13C); CD272 (BTLA); CD275 (B7H2, ICOSL); CD277 (BT3.1, B7 family: Butyrophilin 3); CD294 (CRTH2, PGRD2, G protein-coupled receptor 44); CD295 (LEPR); CD296 (ART1, ADP-ribosyltransferase 1); CD298 (ATP1B3, Na K ATPase β3 subunit); CD300a (CMRF-35H); CD300c (CMRF-35A); CD305 (LAIR1); CD314 (NKG2D); CD316 (EW12); CD317 (BST2); CD319 (CRACC, SLAMF7); CD321 (JAM1); CD322 (JAM2); CDw328 (Siglec7); and/or CD68 (gp 110, Macrosialin).

In some embodiments, the antigen-binding moiety specifically binds to an antigen that is prominently expressed and/or present on T cells upon activation (i.e., activated T cell targets). Exemplary activated T cell targeting moieties include, but are not limited to, CD1a (RA, T6, HTA-1); CD1b (R1); Cd1c (M241, R7); CD1d (R3); CD9 (p24, DRAP-1, MRP-1); CD25 (Tac antigen, IL-2Rα, p55); CD30 (Ber-H2, Ki-1); CD39 (ATPdehydrogenase, NTPdehydrogenase-1); CD45RO (UCHL-1); CD49a (VLA-1α, α1 Integrin); CD49b (VLA-2α, gpla, α2 Integrin); CD69 (AIM, EA 1, MLR3, gp34/28, VEA); CD70 (Ki-24, CD27 ligand); CD74 (Ii, invariant chain); CD80 (B7, B7-1, BB1); CD86 (B7-2/B70); CD96 (TACTILE); CD97 (BL-KDD/F12); CD101 (IGSF2, P126, V7); CD103 (HML-1, Integrin αE, ITGAE); CD107a (LAMP-1); CD107b (LAMP-2); CD109 (8A3, E123 7D1); CD134 (OX40, TNFRSF4); CDw137 (4-IBB, ILA); CD146 (Muc 18, S-endo, MCAM, Mel-CAM); CD152 (CTLA-4); CD154 (CD40L, gp39, TRAP-1, T-BAM); CD166 (ALCAM, KG-CAM, SC-1, BEN, DM-GRASP); CD178 (Fas Ligand); CD227 (MUC1, PUM, PEM, EMA); CD253 (TRAIL, TNF (ligand) superfamily, member 10); CD254 (TRANCE, RANKL, TNF (ligand) superfamily, member 11); CD258 (LIGHT, TMF (ligand) superfamily, member 14); CD267 (TACI, TNF-R superfamily, member 13B); CD273 (B7DC, PDL2); CD274 (B7H1, PDL1); CD278 (ICOS); CD279 (PD1); and/or CD312 (EMR2).

In some embodiments, the antigen-binding moiety specifically binds to B-Cell Surface Markers (e.g., Activated B-cells: CD28, CD38, CD69, CD80, CD83, CD86, DPP4, FCER2, IL2RA, TNFRSF8, CD70 (TNFSF7); Mature B-cells: CD19, CD22, CD24, CD37, CD40, CD72, CD74, CD79A, CD79B, CR2, IL1R2, ITGA2, ITGA3, MS4A1, ST6GAL1; Other B-cell Surface Markers: CD1C, CHST10, HLA-A, HLA-DRA, NT5E), Natural Killer (NK) cell Surface Markers (e.g., CD2, CD244, CD247, CD7, CD96, CHST10, IL12RB1, KLRB1, KLRC1, KLRD1, NCAM1), monocyte and macrophage cell surface markers (e.g., Activated Macrophages: CD69, ENG, FCER2, IL2RA; Other Monocyte and Macrophage Surface Markers: C5AR1, CD163, CD40, CD63, CD74, CD86, CHST10, CSF1R, DPP4, FCGR1A, HLA-DRA, ICAM2, IL1R2, ITGA1, ITGA2, S100A8, TNFRSF8, CD70 (TNFSF7), endothelial cell surface markers (e.g., ENG, ICAM2, NOS3, PECAM1, SELP, TEK, VCAM1, VWF), Smooth Muscle cell Surface Markers (e.g., MYH10, MYH9, MYOCD), mast cell surface markers (e.g., C5AR1, FCER1A, FCER2, TPSAB1), Fibroblast (Stromal) Surface Markers (e.g., ALCAM, COL1A1, COL1A2), epithelial cell surface markers: (e.g., CD1D, KRT18, KRT5, KRT8, EPCAM), or any combination thereof.

Conditionally Stable Fusion Proteins

There are provided, in some embodiments, conditionally stable fusion proteins. In some embodiments of the compositions, methods, and systems provided herein, at least one of the N, P, M, or L is a conditionally stable fusion protein. There are provided, in some embodiments, viral vectors comprising a polynucleotide encoding: a nucleoprotein (N), a phosphoprotein (P), a matrix protein (M), an RNA-dependent RNA polymerase (L), and one or more transgenes, wherein at least one of the N, P, M, or L is a conditionally stable fusion protein. In some embodiments, P is a conditionally stable fusion protein. In some embodiments, the conditionally stable fusion protein comprises a stabilizing molecule binding domain. The stabilizing molecule binding domain can bind a stabilizing molecule in some embodiments. The conditionally stable fusion protein can change from a destabilized state to a stabilized state when the stabilizing molecule binding domain binds to the stabilizing molecule. The conditionally stable fusion protein can comprise one or more at the N, P, M, or L operatively linked to a stabilizing molecule binding domain. The conditionally stable fusion protein can comprise one or more of the N, P, M, or L fused in frame with a stabilizing molecule binding domain. The conditionally stable fusion protein can comprise one or more of the N, P, M, or L associated with a stabilizing molecule binding domain via a linker. In some embodiments, the stabilizing molecule binding domain does not interfere with the function of the one or more N, P, M, or L present in the fusion protein when the conditionally stable fusion protein is in a stabilized state. In some embodiments, the conditionally stable fusion protein comprises P. In some embodiments, the conditionally stable fusion protein comprises M. In some embodiments, the conditionally stable fusion protein comprises L. In some embodiments, the conditionally stable fusion protein comprises N. In some embodiments, the degradation rate of the conditionally stable fusion protein is increased by at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) when it is not bound by the stabilizing molecule. The dynamic range of the conditionally stable fusion protein can vary. In some embodiments, the conditionally stable fusion protein has a large dynamic range. In some embodiments, the conditionally stable fusion protein has a small dynamic range. The kinetics of degradation of the conditionally stable fusion protein can vary. In some embodiments, the conditionally stable fusion protein has rapid kinetics of degradation. In some embodiments, the conditionally stable fusion protein has slow kinetics of degradation. The dose-response behavior of the conditionally stable fusion protein can vary.

Disclosed herein include viral vectors. In some embodiments, the viral vector comprises a polynucleotide encoding: a N, a P, a M, a L, and one or more transgenes, wherein at least one of the N, P, M, or L is a conditionally stable fusion protein comprising a stabilizing molecule binding domain capable of binding a stabilizing molecule, and wherein the conditionally stable fusion protein changes from a destabilized state to a stabilized state when the stabilizing molecule binding domain binds to the stabilizing molecule.

The stabilizing molecule binding domain can comprise any antigen-binding moiety provided herein, such as, for example, a nanobody, Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), an RNA aptamer, adNectin, iMab, anticalin, microbody, peptide aptamer, designed ankyrin repeat protein (DARPin), affilin, tetranectin, avimer, affibody, Kunitz domain, or any combination thereof. The antigen-binding moiety of the stabilizing molecule binding domain can be configured to specifically bind the stabilizing molecule. The antigen-binding moiety of the stabilizing molecule binding domain can specifically bind one or more stabilizing molecules in some embodiments. In some embodiments, stabilizing molecule binding domain is configured to function as a degron when the antigen-binding moiety is not bound to the stabilizing molecule. In some embodiments, the antigen-binding moiety of the stabilizing molecule binding domain is configured to function as a degron when it is not bound to the stabilizing molecule. The conditionally stable fusion protein in a destabilized state can have increased propensity for degradation by ubiquitin-dependent and/or ubiquitin-independent pathways.

The stabilizing molecule can be an endogenous molecule of a target cell or an exogenous molecule of a target cell (e.g., a synthetic protein circuit component). As used herein, the term "endogenous molecule" shall be given its ordinary meaning and shall also refer to polynucleotides, polypeptides, or other molecules that are expressed naturally or originate within an organism or cell. That is, endogenous polynucleotides, polypeptides, or other compounds are not exogenous. For instance, an "endogenous" polynucleotide or peptide is present in the cell when the cell was originally isolated from nature. As used herein, the term "exogenous molecule" shall be given its ordinary meaning and shall also refer to any polynucleotides, polypeptides, or other molecules that are not naturally expressed or produced in the particular cell or organism where expression is desired. Exogenous polynucleotides, polypeptides, or other compounds (e.g., administered drugs) are not endogenous. The stabilizing molecule can be a molecule specific to a cell type. The stabilizing molecule can be a molecule specific to a disease or disorder, such as protein overexpressed in infected cells or cancer cells. The stabilizing molecule can be a molecule absent in non-target cells.

An exogenous molecule of a target cell can comprise a molecule administered to a subject. An exogenous molecule of a target cell can comprise a protein administered to a subject. An exogenous molecule of a target cell can comprise a protein expressed from a polynucleotide administered to a subject. In some embodiments the stabilizing molecule is a synthetic protein circuit component. In some embodiments the stabilizing molecule is a synthetic protein circuit component whose localization, expression, activity, and/or stability are regulated by a synthetic protein circuit. In some embodiments, the stabilizing molecule comprises a protease. In some embodiments, the stabilizing molecule is an endogenous molecule of the target cell whose localization, expression, activity, and/or stability is modified by a synthetic protein circuit component (e.g., activation or inactivation by a protease circuit component). In some such embodiments, a synthetic protein circuit is configured to regulate viral vector replication. In some such embodiments, an intracellular state is used as an input for a synthetic protein circuit, wherein a component of the synthetic protein circuit is the stabilizing molecule.

The viral vector polynucleotide can be capable of being replicated when the conditionally stable fusion protein is present. In some embodiments, the viral vector polynucleotide is replicated when the conditionally stable fusion protein is present. The viral vector polynucleotide can be capable of being replicated only when the conditionally stable fusion protein is present. The viral vector polynucleotide can be capable of being replicated when the conditionally stable fusion protein is in the stabilized state. In some embodiments, the viral vector polynucleotide is replicated when the conditionally stable fusion protein is in the stabilized state. In some embodiments, the viral vector polynucleotide is not capable of being replicated when the conditionally stable fusion protein is in the destabilized state. In some embodiments, the viral vector polynucleotide is not replicated when the conditionally stable fusion protein is in the destabilized state. In some embodiments, the viral vector polynucleotide is not capable of being replicated when the stabilizing molecule is absent. In some embodiments, the viral vector polynucleotide is not replicated when the stabilizing molecule is absent. The viral vector polynucleotide can be capable of being replicated at a threshold concentration of the stabilizing molecule. In some embodiments, the viral vector polynucleotide is replicated at a threshold concentration of the stabilizing molecule.

In some embodiments, the viral vector polynucleotide is not capable of being replicated when the stabilizing molecule is present. In some embodiments, the viral vector polynucleotide is not replicated when the stabilizing molecule is present. The viral vector polynucleotide can be capable of being replicated at below a threshold concentration of the stabilizing molecule.

Protease Fusion Proteins

There are provided, in some embodiments, protease fusion proteins. In some embodiments of the compositions, methods, and systems provided herein, two of N, P, M, or L are expressed as a protease fusion protein. In some embodiments, N and P are expressed as a protease fusion protein. In some embodiments, N and M are expressed as a protease fusion protein. In some embodiments, N and L are expressed as a protease fusion protein. In some embodiments, P and M are expressed as a protease fusion protein. In some embodiments, P and L are expressed as a protease fusion protein. In some embodiments the protease fusion protein comprises a protease. The protease fusion protein can comprise a first cut site and a second cut site. The protease can cut the first cut site and the second cut site. The protease can be in an active state when the first cut site and the second cut site are not cut. The protease can cut the first cut site and the second cut site when the protease is not bound by a protease inhibitor. The protease can be incapable of cutting the first cut site and the second cut site when the protease is bound by a protease inhibitor. The first cut site and the second cut site can flank the protease. In some embodiments, the two of N, P, M, or L are separated from the protease by the first cut site and the second cut site, respectively. The orientation of the protease, the first cut site, the second cut site, and the two of N, P, M, or L in the protease fusion protein can vary. For example, in some embodiments, the 5'-to-3' orientation of the protease fusion protein is 5'-P-the first cut site-protease-the second cut site-L-3'. The two of N, P, M, or L can be in inactive states when the first cut site and/or the second cut site are not cut. For example, when P and L are expressed as a protease fusion protein, P and/or L can be in inactive states when the first cut site and/or the second cut site are not cut.

There are provided, in some embodiments, a viral vector comprising a polynucleotide encoding: a nucleoprotein (N), a phosphoprotein (P), a matrix protein (M), an RNA-dependent RNA polymerase (L), and one or more transgenes, wherein two of the N, P, M, or L are expressed as a protease fusion protein comprising a first protein and a second protein of the two of the N, P, M, or L separated from a protease by a first cut site and a second cut site, respectively, wherein The viral vector polynucleotide can be capable of being replicated when the first protein and the second protein are in active states. In some embodiments, the viral vector polynucleotide is replicated when the first protein and the second protein are in active states. In some embodiments, the viral vector polynucleotide is replicated only when the first protein and the second protein are in active states. The first protein and the second protein can be in active states when the protease inhibitor is absent. The first protein and the second protein can be in active states only when the protease inhibitor is absent. The viral vector polynucleotide can be capable of being replicated when the protease inhibitor is absent. The viral vector polynucleotide can be capable of being replicated only when the protease inhibitor is absent. In some embodiments, the viral vector polynucleotide is not capable of being replicated when the first protein and the second protein are in inactive states.

In some embodiments, the first protein and the second protein are in inactive states when the protease inhibitor is present. In some embodiments, the viral vector polynucleotide is not capable of being replicated when the protease inhibitor is present. The first protein and the second protein can be in inactive states at a threshold concentration of the protease inhibitor. In some embodiments, the viral vector polynucleotide is not capable of being replicated at a threshold concentration of the protease inhibitor.

The protease can comprise a hepatitis C virus (HCV) protease. The protease inhibitor can comprise asunaprevir, simeprevir, telaprevir, sovaprevir, danoprevir, ciluprevir, boceprevir, paritaprevir, or any combination thereof. The protease can comprise an orthogonal protease. The protease can comprise TEV protease, HCV protease, TEV protease, TVMV protease, soybean mosaic virus protease (SMVP), herpes simplex virus protease (HSVP), or any combination thereof. Exemplary protease inhibitors include, but are not limited to, boceprevir (SCH-503034, SCH-7), telaprevir (VX-950), asunaprevir (BMC-650032), danoprevir (RG-7227), faldaprevir (BI-201335), narlaprevir, simeprevir (TMC435), vaniprevir (MK-7009), VX-813, ABT-450, ACH-1625, ACH-2684, BI-1230, MK-5172, SCH-900518, VBY-376, VX-500, GS-9256, GS-9451, BMS-790052, BMS-605339, PHX-1766, AS-101, IDX320, YH-5258, YH5530 and YH5531, AZD-2836 (A-831), AZD-7295 (A-689), daclatasvir, GS-5885, GSK2336805, ABT-267, PPI-668, BMS-790052, or any combination thereof.

Degron Fusion Protein

There are provided, in some embodiments, degron fusion proteins. In some embodiments of the compositions, methods, and systems provided herein, at least one of the N, P, M, or L is a degron fusion protein. A degron fusion protein can comprise a degron. The degron can bind a degron stabilizing molecule. Binding of the degron fusion protein to the degron stabilizing molecule can change the degron fusion protein from a destabilized state to a stabilized state. As used herein, the term "degron" shall be given its ordinary meaning and shall also refer to a polypeptide sequence that is inducibly resistant or susceptible to degradation in the cellular context by the addition or subtraction of a ligand (e.g., a degron stabilizing molecule). In some embodiments, N is expressed as a degron fusion protein. In some embodiments, P is expressed as a degron fusion protein. In some embodiments, M is expressed as a degron fusion protein. In some embodiments, L is expressed as a degron fusion protein. In some embodiments, the degradation rate of the degron fusion protein is increased by at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) when it is not bound by the degron stabilizing molecule. The dynamic range of the degron fusion protein can vary. In some embodiments, the degron fusion protein has a large dynamic range. In some embodiments, the degron fusion protein has a small dynamic range. The kinetics of degradation of the degron fusion protein can vary. In some embodiments, the degron fusion protein has rapid kinetics of degradation. In some embodiments, the degron fusion protein has slow kinetics of degradation. The dose-response behavior of the degron fusion protein can vary.

There are provided, in some embodiments, a viral vector comprising a polynucleotide encoding: a nucleoprotein (N), a phosphoprotein (P), a matrix protein (M), an RNA-dependent RNA polymerase (L), and one or more transgenes, wherein at least one of the N, P, M, or L is a degron fusion protein comprising a degron capable of binding a degron stabilizing molecule, and wherein the degron fusion protein changes from a destabilized state to a stabilized state when the degron binds to the degron stabilizing molecule. The viral vector polynucleotide can be capable of being replicated when the degron fusion protein is in the stabilized state. In some embodiments, viral vector polynucleotide is replicated when the degron fusion protein is in the stabilized state. In some embodiments, the viral vector polynucleotide is not capable of being replicated when the degron fusion protein is in the destabilized state. In some embodiments, the viral vector polynucleotide is not capable of being replicated when the degron stabilizing molecule is absent. The viral vector polynucleotide can be capable of being replicated at a threshold concentration of the degron stabilizing molecule. In some embodiments, the viral vector polynucleotide is replicated at a threshold concentration of the degron stabilizing molecule.

The degron can comprise DHFR degron, an N-degron, a phospho degron, a heat inducible degron, a photosensitive degron, an oxygen dependent degron, ornithine decarboxylase degron, estrogen receptor domain degrons, a ecDHFR degron, an FKBP degron, a UnaG degron, or any combination thereof. As a non-limiting example, the degron may be an ornithine decarboxylase degron. The degron can comprise a ecDHFR degron. The degron stabilizing molecule can comprise trimethoprim (TMP). The degron stabilizing molecule can comprise shield-1, trimethoprim (IMP), estrogen receptor antagonists, bilirabin (BR), or any combination thereof. The degron stabilizing molecule can comprise trimethoprim (TMP). The degron stabilizing molecule can be an endogenous molecule of a target cell or can be an exogenous molecule of a target cell. The degron stabilizing molecule can be a molecule specific to a cell type. The degron stabilizing molecule can be a molecule specific to a disease or disorder.

In some embodiments the degron stabilizing molecule is a synthetic protein circuit component. In some embodiments the degron stabilizing molecule is a synthetic protein circuit component whose localization, expression, activity, and/or stability are regulated by a synthetic protein circuit. In some embodiments, the degron stabilizing molecule comprises a protease. In some embodiments, the degron stabilizing molecule is an endogenous molecule of the target cell whose localization, expression, activity, and/or stability is modified by a synthetic protein circuit component (e.g., activation or inactivation by a protease circuit component). In some such embodiments, a synthetic protein circuit is configured to regulate viral vector replication. In some such embodiments, an intracellular state is used as an input for a synthetic protein circuit, wherein a component of the synthetic protein circuit is the degron stabilizing molecule.

Sender Cells

There are provided, in some embodiments, sender cells capable of releasing a viral vector disclosed herein. The sender cells can comprise a nucleic acid encoding the viral vector polynucleotide. The sender cells can comprise a nucleic acid encoding any of the glycoproteins disclosed herein. The sender cells can comprise a nucleic acid capable of expressing a full-length complementary copy of the viral vector polynucleotide. The sender cells can comprise a nucleic acid capable of expressing one or more of N, P, and/or L in trans.

For example, sender cells can comprise a viral cDNA expression vector and/or expression vectors encoding N, P, and L. The nucleic acid encoding the viral genome (e.g., viral vector polynucleotide) can be operatively linked with a transcriptional signal and may further comprises a transcriptional terminator and a ribozyme sequence at the 3' end of the nucleic acid encoding the viral genome. The ribozyme sequence can allow for cleavage of the transcript at the 3' end of the viral sequence. In some embodiments, the nucleic acid encoding a genome or antigenome of the viral vector (e.g., viral vector polynucleotide) can be operably linked with an expression control sequence to direct synthesis of viral RNA transcripts from the cDNA expression vector in the sender cell. In some embodiments, the viral cDNA expression vector can comprise a cDNA encoding the positive strand full-length sequence (antigenome) of the viral vector. In some embodiments, in the viral cDNA expression vector, hammerhead and hepatitis delta virus ribozymes can flank the viral vector (e.g., rabies virus) antigenomic cDNA, enabling the production of authentic 5' and 3' ends of antigenomic viral RNA by transcription. The first ten nucleotides of the hammerhead sequence can be designed to be complementary to the first ten nucleotides of the antisense genomic sequence. The viral cDNA expression vector encoding a genome or antigenome of the viral vector can operably linked with an expression control sequence to direct synthesis of viral RNA transcripts from the cDNA expression vector in the sender cell. Transcription of the viral cDNA expression vector can involve both cellular RNA dependent RNA polymerase II, which is available in mammalian cells, as well as exogenous phage (e.g., T7) RNA polymerase. The viral cDNA expression vector can be a transfected plasmid or can be integrated in the sender cell genome. In some embodiments, sender cells also comprise one or more trans-complementation vectors expressing an N protein, a P protein, and/or an L protein in trans (e.g., from a transiently transfected expression vector). The viral RNA that is a genomic or antigenomic equivalent can be packaged by the N protein and then can replicated by the P/L proteins. G protein, if absent from the viral vector polynucleotide, can be provided in trans by the sender cell, thereby producing viral particles. Introduction of nucleic acids into sender cells can be affected by any of a variety of methods known in the art, such as, for example, calcium phosphate transfection, DEAE-dextran mediated transfection, cationic lipid-mediated transfection, electroporation, electrical nuclear transport, chemical transduction, electrotransduction, and/or infection. In some embodiments, transfection facilitating reagent is added to increase DNA uptake by cells. Many of these reagents are known in the art, such as, for example, LIPOFECTACE, EFFECTENE, and any other cationic lipid that coats DNA and enhances DNA uptake by cells. In some embodiments lipid nanoparticle (LNP) compositions are employed to introduce nucleic acids into sender cells.

In some embodiments, sender cells are configured to express the positive strand full-length sequence (antigenome), N protein, P protein, L protein, and/or phage RNA polymerase in response to one or more signals. In some embodiments, sender cell expression the of positive strand full-length sequence (antigenome), N protein, P protein, L protein, glycoprotein, first bridge protein, second bridge protein, and/or phage RNA polymerase is under the control of an inducible promoter. In some embodiments, the inducible promoter is under the control of a dose-dependent inducer of the inducible promoter. In some embodiments, the dose-dependent inducer comprises tetracycline, pristinamycin, macrolide, ecdysone, mifepristone, or any combination thereof. In some embodiments, the sender cell can be capable of sensing a first inducing signal, a second inducing signal, and/or a third inducing signal. In some embodiments, the sender cell senses a first inducing signal, a second inducing signal, and/or a third inducing signal. In some embodiments, the first inducing signal, a second inducing signal, and/or a third inducing signal is, directly or indirectly, a dose-dependent inducer of an inducible promoter driving sender expression of the positive strand full-length sequence (antigenome), N protein, P protein, L protein, glycoprotein, first bridge protein, second bridge protein, and/or phage RNA polymerase. In some embodiments, a synthetic protein circuit component is inducer of an inducible promoter driving sender expression of the positive strand full-length sequence (antigenome), N protein, P protein, L protein, glycoprotein, first bridge protein, second bridge protein, and/or phage RNA polymerase.

The first inducing signal, second inducing signal, and/or third inducing signal can comprise an endogenous signal of the target cell. The endogenous signal of the target cell can comprise a physiological signal and/or a pathological signal. The endogenous signal of the target cell can comprise immune cell activation. The endogenous signal of the target cell can comprise inhibition of immune cell exhaustion. The endogenous signal of the target cell can comprise immune cell exhaustion. The endogenous signal of the target cell can comprise a component of a tumor microenvironment. The first inducing signal, second inducing signal, and/or third inducing signal can comprise an exogenous signal of the target cell. The exogenous signal of the target cell can comprise a small molecule (e.g, doxycycline). In some embodiments, the exogenous signal comprises a synthetic protein circuit component (e.g., activation or inactivation of a protease circuit component). The sender cells can comprise a synthetic receptor system, wherein the synthetic receptor system is configured to sense the first inducing signal, second inducing signal, and/or third inducing signal (e.g., a Synthetic Notch (SynNotch) receptor, a Modular Extracellular Sensor Architecture (MESA) receptor (CAR), Tango, dCas9-synR, a chimeric antigen receptor, or any combination thereof) and induce expression from an inducible promoter provided herein.

The sender cell can be capable of inducing expression of the glycoprotein in response to sensing a first inducing signal. In some embodiments, the sender cell induces expression of the glycoprotein in response to sensing a first inducing signal. The sender cell can be capable of inducing expression of the glycoprotein in response to sensing a threshold level of the first inducing signal. In some embodiments, the sender cell induces expression of the glycoprotein in response to sensing a threshold level of the first inducing signal. The sender cell can be capable of releasing the viral vector by inducing expression of the glycoprotein. In some embodiments, the sender cell releases the viral vector by inducing expression of the glycoprotein. In some embodiments, the sender cell is not capable of releasing the viral vector when the sender cell does not induce expression of the glycoprotein. In some embodiments, the sender cell does not release the viral vector when the sender cell does not induce expression of the glycoprotein. In some embodiments, the sender cell is not capable of releasing the viral vector when the sender cell does not sense a first inducing signal. In some embodiments, the sender cell does not release the viral vector when the sender cell does not sense a first inducing signal.

The sender cell can be capable of inducing expression of the first bridge protein in response to sensing a second inducing signal. In some embodiments, the sender cell induces expression of the first bridge protein in response to sensing a second inducing signal. The sender cell can be capable of inducing expression of a second bridge protein in response to sensing a third inducing signal. In some embodiments, the sender cell induces expression of a second bridge protein in response to sensing a third inducing signal. The second bridge protein can comprise a glycoprotein binding domain and a second antigen-binding moiety. The second antigen-binding moiety can be capable of binding a second antigen on a surface of the target cell. In some embodiments, the first bridge protein and the second bridge protein are identical, while in other embodiments the first bridge protein and the second bridge protein are different.

The sender cells can comprise an immune cell, a cancer cell, a stem cell, or any combination thereof. The sender cells can comprise a natural killer (NK) cell. The sender cells can comprise a tumor infiltrating lymphocyte. The sender cells can comprise an autologous cell derived from the subject. The sender cells can comprise an allogenic cell derived from a donor.

Sender cell can comprise fibroblasts, epithelial cells (e.g., renal, mammary, prostate, lung), keratinocytes, hepatocytes, adipocytes, endothelial cells, and hematopoietic cells. In some embodiments, sender cells comprise adult cells (e.g., terminally differentiated, dividing or non-dividing), embryonic cells (e.g., blastocyst cells, etc.), stem cells, or any combination thereof. In some embodiments, the sender cell is a cell line derived from an animal or other source.

In some embodiments, sender cells comprise stem cells. A variety of stem cells types are known in the art and can be used as sender cells, including for example, embryonic stem cells, inducible pluripotent stem cells, hematopoietic stem cells, neural stem cells, epidermal neural crest stem cells, mammary stem cells, intestinal stem cells, mesenchymal stem cells, olfactory adult stem cells, testicular cells, and progenitor cells (e.g., neural, angioblast, osteoblast, chondroblast, pancreatic, epidermal, etc.). In some embodiments, the stem cells are stem cell lines derived from cells taken from a subject.

In some embodiments, the sender cell is a cell found in the circulatory system of a mammal, including humans. Exemplary circulatory system cells include, among others, red blood cells, platelets, plasma cells, T-cells, natural killer cells, B-cells, macrophages, neutrophils, or the like, and precursor cells of the same. As a group, these cells are defined to be circulating eukaryotic cells of the invention. In some embodiments, the sender cells are derived from any of these circulating eukaryotic cells. The compositions, methods, and systems provided herein contemplate any of these circulating cells as sender cells (or sender cells derived from the circulating cells). In some embodiments, the sender cell is a T-cell or T-cell precursor or progenitor cell. In some embodiments, the sender cell is a helper T-cell, a cytotoxic T-cell, a memory T-cell, a regulatory T-cell, a natural killer T-cell, a mucosal associated invariant T-cell, a gamma delta T cell, or a precursor or progenitor cell to the aforementioned. In some embodiments, the sender cell is a natural killer cell, or a precursor or progenitor cell to the natural killer cell. In some embodiments, the sender cell is a B-cell, or a B-cell precursor or progenitor cell. In some embodiments, the sender cell is a neutrophil or a neutrophil precursor or progenitor cell. In some embodiments, the sender cell is a megakaryocyte or a precursor or progenitor cell to the megakaryocyte. In some embodiments, the sender cell is a macrophage or a precursor or progenitor cell to a macrophage.

In some embodiments, sender cells are genetically modified (e.g., introduced with the nucleic acids provided herein). In some embodiments the sender cells are administered to a subject in need. In some embodiments, sender cells configured to release the viral vectors provided herein may be used for adoptive cell therapy. As used herein. adoptive cell transfer refers to the administration of sender cells (e.g., homing immune cells from autologous, allogenic or genetically modified hosts) configured to release viral vectors as disclosed herein. In some embodiments, adoptive cell therapy is carried out by autologous transfer, wherein the cells are derived from a subject in need of a treatment and the cells, following isolation and processing (e.g., configured to release the viral vectors provided herein) are administered to the same subject. In other instances, adoptive cell therapy may involve allogenic transfer wherein the cells are isolated and/or prepared (e.g., configured to release the viral vectors provided herein) from a donor subject other than the recipient subject who ultimately receives cell therapy. The donor and recipient subject may be genetically identical, or similar or may express the same HLA class or subtype. The sender cells can be NK cells, e.g., allogenic NK cells. NK cells may be isolated from peripheral blood mononuclear cells (PBMCs), or derived from human embryonic stem (ES) cells and induced pluripotent stem cells (iPSCs). The primary NK cells isolated from PBMCs may be further expanded for adoptive cell therapy. In some embodiments, graft-versus-host-disease does not occur in a subject administered allogenic NK sender cells as described herein.

Systems

There are provided, in some embodiments, systems for delivering a polynucleotide to a target cell of a subject in need thereof. There are provided, in some embodiments, systems for delivering a synthetic protein circuit to a target cell of a subject in need thereof. The synthetic protein circuit can be any of the synthetic protein circuits disclosed in Gao et al., Science 361, 1252-1258 (2018); U.S. Publication No. US 2019/0248873; and U.S. application with attorney docket no. 30KJ-300662-US, filed on Aug. 29, 2019 that claims the benefit of priority to U.S. Provisional Application No. 62/725,959, filed on Aug. 31, 2018; the content of each of these references is incorporated herein by reference in its entirety. In some embodiments, the system comprises: a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; and a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein.

Disclosed herein include systems for delivering a polynucleotide to a target cell of a subject in need thereof. In some embodiments, the system comprises: a sender cell capable of releasing a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; and a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein.

Disclosed herein include systems for delivering a polynucleotide to a target cell of a subject in need thereof. In some embodiments, the system comprises: a sender cell capable of releasing: (1) a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; and (2) a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein.

The systems provided herein can comprise any of the viral vectors, sender cells, and/or bridge proteins disclosed herein (e.g. the first, second, third, and/or fourth layers of control). For example, in some embodiments, at least one of the N, P, M, or L is a conditionally stable fusion protein comprising a stabilizing molecule binding domain capable of binding a stabilizing molecule, and wherein the conditionally stable fusion protein changes from a destabilized state to a stabilized state when the stabilizing molecule binding domain binds to the stabilizing molecule. Additionally, in some embodiments, two of the N, P, M, or L are expressed as a protease fusion protein comprising a first protein and a second protein of the two of the N, P, M, or L separated from a protease by a first cut site and a second cut site, respectively, wherein the protease is capable of cutting the first cut site and the second cut site when the protease is not bound by a protease inhibitor, and wherein the first protein and the second protein are in inactive states when the first cut site and the second cut site are not cut, respectively. Furthermore, in some embodiments, at least one of the N, P, M, or L is a degron fusion protein comprising a degron capable of binding a degron stabilizing molecule, and wherein the degron fusion protein changes from a destabilized state to a stabilized state when the degron binds to the degron stabilizing molecule. In some embodiments, the viral vector polynucleotide does not encode the glycoprotein. In some embodiments, the glycoprotein, or a portion thereof, is derived of another species than the viral vector polynucleotide. In some embodiments, the glycoprotein comprises EnvA, EnvB, EnvC, EnvD, EnvE, EnvJ, or a portion thereof.

Methods for Delivering a Polynucleotide

There are provided, in some embodiments, methods for delivering a polynucleotide to a target cell of a subject in need thereof. In some embodiments, the method comprises: providing a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; providing a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein; and administering the viral vector and the first bridge protein to the subject.

Disclosed herein include methods for delivering a polynucleotide to a target cell of a subject in need thereof. In some embodiments, the method comprises: providing a sender cell capable of releasing a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; providing a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein; and administering the sender cell and the first bridge protein to the subject.

Disclosed herein include methods for delivering a polynucleotide to a target cell of a subject in need thereof. In some embodiments, the method comprises: providing a sender cell capable of releasing: (1) a viral vector comprising a polynucleotide encoding nucleoprotein (N), phosphoprotein (P), matrix protein (M), RNA-dependent RNA polymerase (L), and one or more transgenes, wherein a membrane envelope of the viral vector comprises a glycoprotein; and (2) a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein; and administering the sender cell to the subject.

The methods provided herein can comprise any of the viral vectors, sender cells, and/or bridge proteins disclosed herein (e.g. the first, second, third, and/or fourth layers of control). For example, in some embodiments, at least one of the N, P, M, or L is a conditionally stable fusion protein comprising a stabilizing molecule binding domain capable of binding a stabilizing molecule, and wherein the conditionally stable fusion protein changes from a destabilized state to a stabilized state when the stabilizing molecule binding domain binds to the stabilizing molecule. Additionally, in some embodiments, two of the N, P, M, or L are expressed as a protease fusion protein comprising a first protein and a second protein of the two of the N, P, M, or L separated from a protease by a first cut site and a second cut site, respectively, wherein the protease is capable of cutting the first cut site and the second cut site when the protease is not bound by a protease inhibitor, and wherein the first protein and the second protein are in inactive states when the first cut site and the second cut site are not cut, respectively. Furthermore, in some embodiments, at least one of the N, P, M, or L is a degron fusion protein comprising a degron capable of binding a degron stabilizing molecule, and wherein the degron fusion protein changes from a destabilized state to a stabilized state when the degron binds to the degron stabilizing molecule. In some embodiments, the viral vector polynucleotide does not encode the glycoprotein. In some embodiments, the glycoprotein, or a portion thereof, is derived of another species than the viral vector polynucleotide. In some embodiments, the glycoprotein comprises EnvA, EnvB, EnvC, EnvD, EnvE, EnvJ, or a portion thereof.

The method can comprises providing a first inducing signal; and administering the first inducing signal to the subject. In some embodiments, the sender cell induces expression of the glycoprotein following administration of the first inducing signal to the subject. In some embodiments, the sender cell releases the viral vector following administration of the first inducing signal to the subject. The method can comprise: providing a second inducing signal; and administering the second inducing signal to the subject. In some embodiments, the sender cell induces expression of the first bridge protein following administration of the second inducing signal to the subject. The method can comprise providing a third inducing signal; and administering the third inducing signal to the subject. In some embodiments, the sender cell induces expression of the second bridge protein following administration of the third inducing signal to the subject. In some embodiments, the viral vector polynucleotide is delivered to a target cell of the subject. In some embodiments, the one or more transgenes is expressed in the target cell. The method can comprise providing the protease inhibitor; and administering the protease inhibitor to the subject. In some embodiments, replication of the viral vector polynucleotide ceases following administration of the protease inhibitor to the subject. In some embodiments, the expression of the one or more transgenes in the target cell ceases following administration of the protease inhibitor to the subject. The administering can comprise aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or any combination thereof.

The compositions, systems, and methods described herein can be used to express one or more transgenes to treat, prevent, and/or diagnose various diseases or disorders. Non-limiting examples of the diseases include cancer such as carcinoma, sarcoma, leukemia, lymphoma; and autoimmune diseases such as multiple sclerosis. Non-limiting examples of carcinomas include esophageal carcinoma; hepatocellular carcinoma; basal cell carcinoma, squamous cell carcinoma (various tissues); bladder carcinoma, including transitional cell carcinoma; bronchogenic carcinoma; colon carcinoma; colorectal carcinoma; gastric carcinoma; lung carcinoma, including small cell carcinoma and non-small cell carcinoma of the lung; adrenocortical carcinoma; thyroid carcinoma; pancreatic carcinoma; breast carcinoma; ovarian carcinoma; prostate carcinoma; adenocarcinoma; sweat gland carcinoma; sebaceous gland carcinoma; papillary carcinoma; papillary adenocarcinoma; cystadenocarcinoma; medullary carcinoma; renal cell carcinoma; ductal carcinoma in situ or bile duct carcinoma; choriocarcinoma; seminoma; embryonal carcinoma; Wilm's tumor; cervical carcinoma; uterine carcinoma; testicular carcinoma; osteogenic carcinoma; epithelial carcinoma; and nasopharyngeal carcinoma. Non-limiting examples of sarcomas include fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas. Non-limiting examples of solid tumors include glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. Non-limiting examples of leukemias include chronic myeloproliferative syndromes; acute myelogenous leukemias; chronic lymphocytic leukemias, including B-cell CLL, T-cell CLL prolymphocyte leukemia, and hairy cell leukemia; and acute lymphoblastic leukemias. Examples of lymphomas include, but are not limited to, B-cell lymphomas, such as Burkitt's lymphoma; Hodgkin's lymphoma; and the like. Other non-liming examples of the diseases that can be treated using the viral vectors, viral vector polynucleotides, sender cells, bridge proteins, systems, and methods disclosed herein include genetic disorders including sickle cell anemia, cystic fibrosis, lysosomal acid lipase (LAL) deficiency 1, Tay-Sachs disease, Phenylketonuria, Mucopolysaccharidoses, Glycogen storage diseases (GSD, e.g., GSD types I, II, III, IV, V, VI, VII, VIII, IX, X, XI, XII, XIII, and XIV), Galactosemia, muscular dystrophy (e.g., Duchenne muscular dystrophy), and hemophilia.

Additionally, the compositions, systems, and methods provided herein may be used for the diagnosis, treatment, and/or prevention of infectious diseases. As used herein, the term "infectious diseases" refers to diseases caused by any pathogen or agent that infects mammalian cells, preferably human cells and causes a disease condition, such as, for example, bacteria, yeast, fungi, protozoans, *mycoplasma*, viruses, prions, and parasites. Non-limiting examples of infectious diseases include (a) viral diseases such as, for example, diseases resulting from infection by an adenovirus, a herpesvirus (e.g., HSV-ί, HSV-II, CMV, or VZV), a poxvirus (e-g~, an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenza virus, mumps virus, measles vims, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B vims), a flavivirus (e.g., hepatitis C virus or Dengue virus), or a retrovirus (e.g., a lentivirus such as HIV); (b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or Bordeteila; (c) other infectious diseases, such *chlamydia*, fungal diseases including but not limited to candidiasis, aspergillosis, histoplasmosis, cryptococcal meningitis, parasitic diseases including but not limited to malaria, *Pneumocystis* carnii pneumonia, leishmaniasis, cryptosporidiosis, toxoplasmosis, and trypanosome infection and prions that cause human disease such as Creutzfeldt-Jakob Disease (CJD), variant Creutzfeldt-Jakob Disease (vCJD), Gerstmann-Straussler-Scheinker syndrome, Fatal Familial Insomnia and kuru.

Diagnostic Applications

In some embodiments, the viral vector expressing one or more transgenes of interest useful in detecting a disease or disorder and/or monitoring the progression of a disease or disorder. As used herein, the term "diagnostic" refers identifying the presence or absence of or nature of a disease or disorder. Such detection methods can be used, for example, for early diagnosis of the condition, to determine whether a subject is predisposed to a disease or disorder, to monitor the progress of the disease or disorder or the progress of treatment protocols, to assess the severity of the disease or disorder, to forecast the an outcome of a disease or disorder and/or prospects of recovery, or to aid in the determination of a suitable treatment for a subject. The detection can occur in vitro or in vivo.

In some embodiments, the transgene encodes a diagnostic agent. The diagnostic agent can be a molecule capable of detection, including, but not limited to, fluorescers, chemiluminescers, chromophores, bioluminescent proteins, enzymes, enzyme substrates, enzyme cofactors, enzyme inhibitors, isotopic labels, semiconductor nanoparticles, dyes, metal ions, metal sols, ligands (e.g., biotin, streptavidin or haptens) and the like. The term "fluorescer" refers to a substance or a portion thereof which is capable of exhibiting fluorescence in the detectable range. For example, the diagnostic agent may comprise, in some embodiments, a fluorescent protein, such as, but not limited to, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, rsCherry, rsCherryRev, or any combination thereof. In some embodiments, the expression, stability, and/or activity (e.g., fluorescence) of the diagnostic agent is configured to be responsive to a disease state or a disorder state. In some embodiments, the diagnostic agent comprises one or more components of a synthetic protein circuit. In some embodiments, the viral vector polynucleotide is configured to express the diagnostic agent constitutively. In some such embodiments, the viral vector is configured to transduce targets cells associated with a disease or disorder (e.g., cancer cells or infected cells. In some embodiments, the disease to be diagnosed is a type of cancer, such as those described herein. In some embodiments, the disease to be diagnosed is associated with infection by an intracellular parasite (e.g., virus, bacterium, protozoan, fungus, or a prion) disclosed herein.

In some embodiments, the diagnostic agent is configured to be expressed, stable, and/or active in lesions (e.g. tumors, infected cells). In some embodiments, the viral vector is configured to transduce lesions and the diagnostic agent is expressed in said lesions. Detection and/or imaging of the diagnostic agent can enable a clinician to intraoperatively, laparoscopically, intravascularly or endoscopically detect said lesions. In some such embodiments, discrimination between lesions (e.g. tumors) and non-lesions (e.g. non-tumor tissue) is enhanced by the detection and/or imaging of the diagnostic agent. In some embodiments, detection and/or imaging of the diagnostic agent can enable a clinician to accurately locate lesions in a patient and thereby aid resection, irradiation, biopsy and/or lesion removal. In some embodiments, detection and/or imaging of the diagnostic agent aids the detection of non-malignant pathological lesions, such as, an infarct, including myocardial, atherosclerotic plaque, clot, including thrombosis, pulmonary embolism, infectious or inflammatory lesion, non-tumorous or noninfectious inflammation, or hyperplasia. The detection and/or imaging of the diagnostic agent may also be used to detect various stages of progression or severity of disease (e.g., benign, premalignant, and malignant breast lesions, tumor growth, or metastasis). The detection and/or imaging of the diagnostic agent may also be used to detect the response of the disease to prophylactic or therapeutic treatments or other interventions. The detection and/or imaging of the diagnostic agent can furthermore be used to help the medical practitioner in determining prognosis (e.g., worsening, status-quo, partial recovery, or complete recovery) of the patient, and the appropriate course of action.

Detection and/or imaging of the diagnostic agent can be performed, for example, using an ultrasound scanner, a magnetic resonance imaging instrument (MM scanner), an X-ray source with film or a detector (e.g., conventional or digital radiography system), an X-ray computed tomography (CT) or computed axial tomography (CAT) scanner, a gamma camera, or a positron emission tomography (PET) scanner. Various medical imaging systems have been developed for open surgery as well as for laparoscopic, thoracoscopic, and robot-assisted surgery and can be used in the practice of the invention. Conventional laparoscopes and endoscopes can be equipped with a photodetector (e.g., camera or CCD detector) to provide guidance during medical procedures. Fiber-optic imaging systems can also be used, which include portable handheld microscopes, flexible endoscopes, and microendoscopes. For example, an illumination source can be added to such devices to allow fluorescence imaging. A miniaturized ultrasound transducer can be added to the tip of a laparoscope or catheter for intravascular ultrasound (IVUS) imaging. Miniaturized imaging systems can be used that allow imaging inside small cavities and constricted spaces. In addition, miniaturized imaging devices (e.g., microendoscopes) may be implanted within a subject for long-term imaging studies. In addition, a camera may be used to take both photographic images of a subject and to detect signals from the diagnostic agent, so that photographic images of the subject and images of the signals from the diagnostic agent can be superimposed to allow regions containing the diagnostic agent to be mapped to the subject's anatomy.

Pharmaceutical Compositions and Methods of Administration

Also disclosed herein are pharmaceutical compositions comprising one or more of the viral vectors, bridge proteins, regulatory molecules (e.g., stabilizing molecules, first inducing signals, second inducing signals, third inducing signals, degron stabilizing molecules, and/or protease inhibitors) and/or sender cell disclosed herein and one or more pharmaceutically acceptable carriers. The compositions can also comprise additional ingredients such as diluents, stabilizers, excipients, and adjuvants. As used herein, "pharmaceutically acceptable" carriers, excipients, diluents, adjuvants, or stabilizers are the ones nontoxic to the cell or subject being exposed thereto (preferably inert) at the dosages and concentrations employed or that have an acceptable level of toxicity as determined by the skilled practitioners.

The carriers, diluents and adjuvants can include buffers such as phosphate, citrate, or other organic acids: antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; monosaccharides, di saccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution.

Titers of the viral vectors, regulatory molecules, bridge proteins, and/or sender cells to be administered will vary depending, for example, on the particular viral vector or sender cell, the mode of administration, the treatment goal, the individual, and the cell type(s) being targeted, and can be determined by methods standard in the art.

As will be readily apparent to one skilled in the art, the useful in vivo dosage of the viral vectors, regulatory molecules, bridge proteins, and/or sender cell to be administered and the particular mode of administration will vary depending upon the age, weight, the severity of the affliction, and animal species treated, the particular recombinant virus expressing the protein of interest that is used, and the specific use for which the recombinant virus is employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

Although the exact dosage will be determined on a drug-by-drug basis, in most cases, some generalizations regarding the dosage can be made. Dosages of the viral vectors, regulatory molecules, bridge proteins, and/or sender cells provided can depend primarily on factors such as the condition being treated, the age, weight and health of the patient, and may thus vary among patients. For example, a therapeutically effective human dosage of the viral vector is generally in the range of from about 0.1 ml to about 100 ml of solution containing concentrations of from about $1 \times 10^9$ to $1 \times 10^{16}$ genomes virus viral. A preferred human dosage can be about $1 \times 10^{13}$ to $1 \times 10^{16}$ viral vector genomes. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting from the vector. The dosage will be adjusted to balance the therapeutic benefit against any side effects and such dosages may vary depending upon the therapeutic application for which the viral vector is employed. The levels of expression of the transgene can be monitored to determine the frequency of dosage resulting from the viral vector.

The viral vectors, regulatory molecules, bridge proteins, and/or sender cells disclosed herein can be administered to a subject (e.g., a human) in need thereof. The route of the administration is not particularly limited. For example, a therapeutically effective amount of the viral vectors, regulatory molecules, bridge proteins, and/or sender cells can be administered to the subject by via routes standard in the art. Non-limiting examples of the route include intramuscular, intravaginal, intravenous, intraperitoneal, subcutaneous, epicutaneous, intradermal, rectal, intraocular, pulmonary, intracranial, intraosseous, oral, buccal, systematic, or nasal. In some embodiments, the viral vectors, bridge proteins, and/or sender cells are administered to the subject by systematic transduction. In some embodiments, the viral vectors, regulatory molecules, bridge proteins, and/or sender cells are administered to the subject by intramuscular injection. In some embodiments, the viral vectors, regulatory molecules, bridge proteins, and/or sender cells are administered to the subject by intravaginal injection. In some embodiments, regulatory molecules, viral vectors, bridge proteins, and/or sender cells are is administered to the subject by the parenteral route (e.g., by intravenous, intramuscular or subcutaneous injection), by surface scarification or by inoculation into a body cavity of the subject. Route(s) of administration can be readily determined by one skilled in the art taking into account the infection and/or disease state being treated and the target cells/tissue(s) that are to express the protein of interest. In some embodiments, it can be advantageous to administer the viral vectors, bridge proteins, and/or sender cells via intravenous administration, Actual administration of the viral vectors, regulatory molecules, bridge proteins, and/or sender cells can be accomplished by using any physical method that will transport the viral vectors, bridge proteins, and/or sender cells into the target tissue of the subject. For example, the viral vectors, regulatory molecules, bridge proteins, and/or sender cells can be administered intravenously. As disclosed herein, glycoprotein of the viral vector can be modified so that the viral vector is targeted to a particular target environment of interest such as central nervous system, and to enhance tropism to the target environment of interest (e.g, CNS tropism). In some embodiments, the viral vector delivers a polynucleotide to the heart, peripheral nerves, or a combination thereof. Pharmaceutical compositions can be prepared, for example, as injectable formulations.

The viral vectors, regulatory molecules, bridge proteins, and/or sender cells to be used can be utilized in liquid or freeze-dried form (in combination with one or more suitable preservatives and/or protective agents to protect the virus during the freeze-drying process). For gene therapy (e.g., of neurological disorders which may be ameliorated by a specific gene product) a therapeutically effective dose of the viral vectors, regulatory molecules, bridge proteins, and/or sender cells expressing the therapeutic protein is administered to a host in need of such treatment. The use of the viral vectors, bridge proteins, and/or sender cells disclosed herein in the manufacture of a medicament for inducing immunity in, or providing gene therapy to, a host is within the scope of the present application.

In instances where human dosages for the viral vectors, regulatory molecules, bridge proteins, and/or sender cells have been established for at least some condition, those same dosages, or dosages that are between about 0.1% and 500%, more preferably between about 25% and 250% of the established human dosage can be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

A therapeutically effective amount of the viral vector, regulatory molecules, bridge protein, and/or sender cell can be administered to a subject at various points of time. For example, the viral vector, regulatory molecule, bridge protein, and/or sender cell can be administered to the subject prior to, during, or after the subject has developed a disease, disorder, and/or infection. The viral vector, bridge protein, regulatory molecule, and/or sender cell can also be administered to the subject prior to, during, or after the occurrence of a disease, disorder, and/or infection. In some embodiments, the viral vector, regulatory molecule, bridge protein, and/or sender cell are administered to the subject during remission of the disease or disorder. In some embodiments, the viral vector, bridge protein, and/or sender cell are administered prior to the onset of the disease or disorder in the subject. In some embodiments, the viral vector, regulatory molecule, bridge protein, and/or sender cell are administered to a subject at a risk of developing the disease or disorder.

The dosing frequency of the viral vector, regulatory molecules, bridge protein, and/or sender cell can vary. For example, viral vector, regulatory molecule, bridge protein, and/or sender cell can be administered to the subject about once every week, about once every two weeks, about once every month, about one every six months, about once every year, about once every two years, about once every three years, about once every four years, about once every five years, about once every six years, about once every seven years, about once every eight years, about once every nine years, about once every ten years, or about once every fifteen years. In some embodiments, the viral vector, regulatory molecule, bridge protein, and/or sender cell are administered to the subject at most about once every week, at most about once every two weeks, at most about once every month, at most about one every six months, at most about once every year, at most about once every two years, at most about once every three years, at most about once every four years, at most about once every five years, at most about once every six years, at most about once every seven years, at most about once every eight years, at most about once every nine years, at most about once every ten years, or at most about once every fifteen years.

EXAMPLES

Some aspects of the embodiments discussed above are disclosed in further detail in the following examples, which are not in any way intended to limit the scope of the present disclosure.

Example 1

Control of Viral Exit by an Inducible G Protein

This example demonstrates the ability of doxycycline-induced expression to control the transmission of a ΔG rabies viral vector.

Figure 2B:
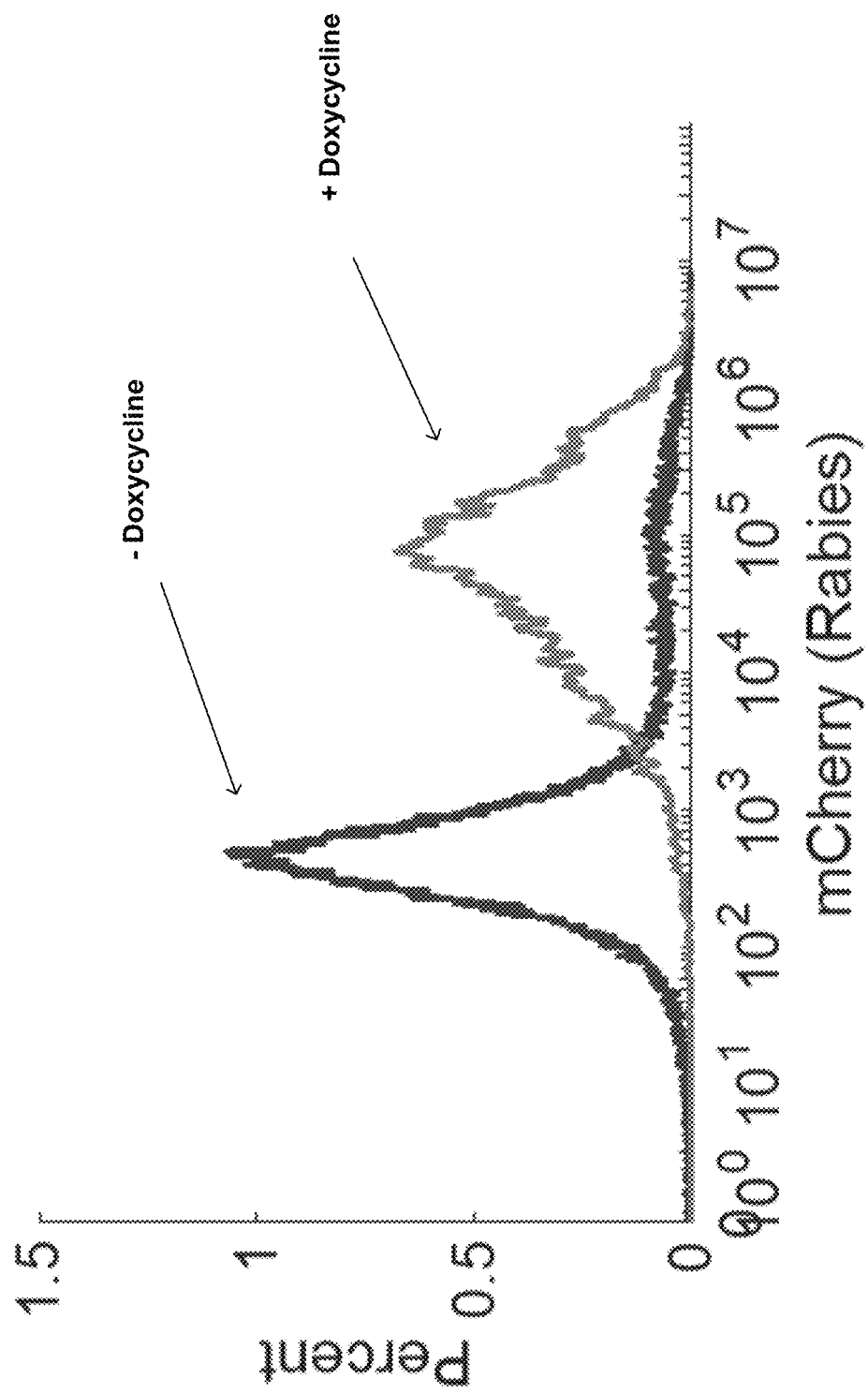
FIGS. 2B-2C depict data related to the inducible exit of viral vector from sender cells and subsequent infection of target cells.
Figure 2C:
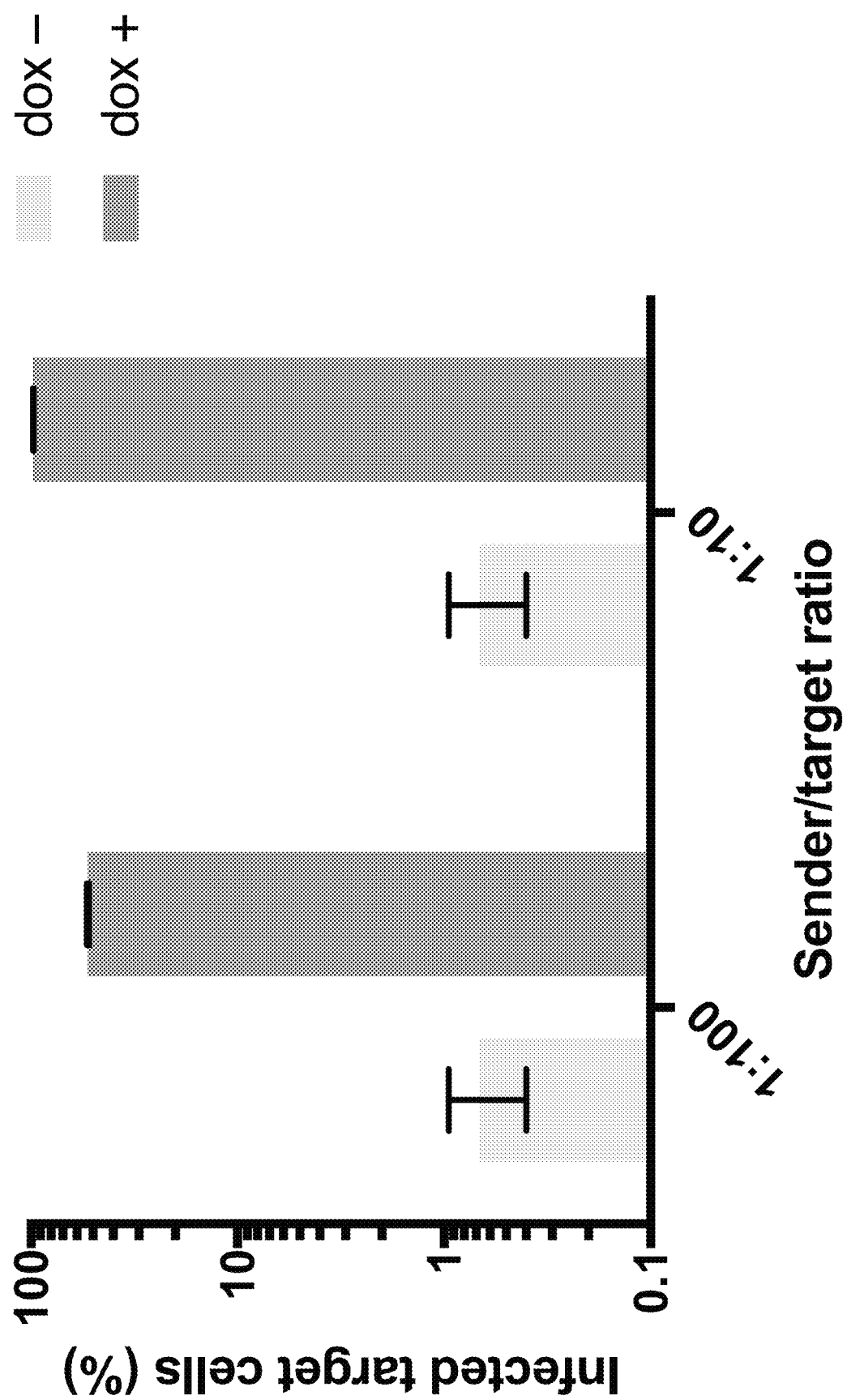

FIG. 2A shows a non-limiting exemplary schematic illustration of a first layer of control of the viral vector. HEK293 cells expressing doxycycline-inducible glycoprotein were infected with a ΔG rabies viral vector encoding an mCherry marker (RVdG-mCherry; shown in FIG. 2A). The cells were cultured for 2 days in the absence or presence of doxycycline. FIGS. 2B-2C depict data related to the inducible exit of viral vector from sender cells and subsequent infection of target cells. As seen in FIGS. 2B-2C, the fraction of infected cells (indicated by mCherry expression) was increased in the presence of doxycycline.

Example 2

A Bridge Protein Mediates Viral Entry Through a Cell Surface Antigen

This example demonstrates targeting of the viral vector to target cells with the use of a bridge protein. Pseudotyping viruses, in which the natural envelope protein is replaced with a foreign viral envelope protein, can alter host tropism. The envelope glycoproteins, EnvA and EnvB, from avian sarcoma leukosis virus (ASLV), can specifically bind to TVA and TVB receptors. These receptors are orthogonal to mammalian cells, thereby facilitating cell-specific infection of mammalian cells which express TVA and TVB. Provided herein are bridge proteins enabling the targeting of pseudotyped viral vectors (e.g., EnvA-pseudotyped viral vectors) to arbitrary surface proteins in target cells. These bridge proteins can be fusions of the extracellular domain of TVA or TVB with an extracellular sensor module, such as, for example, epidermal growth factor (EGF) and single-chain antibodies (scFvs).

Figure 3C:
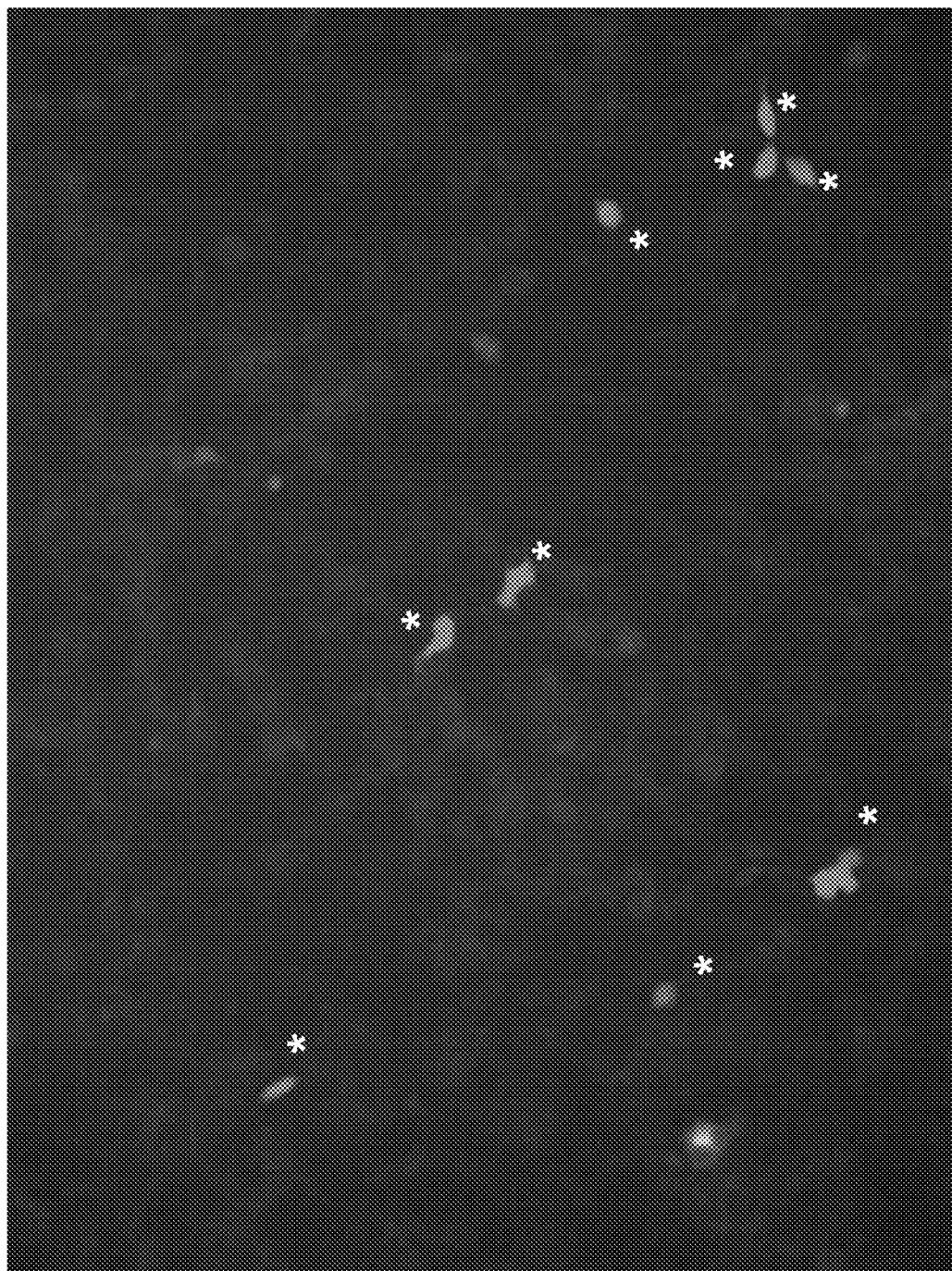
FIGS. 3C-3E depict data related to bridge protein-mediated viral entry of target cells through a cell surface antigen.
Figure 3D:
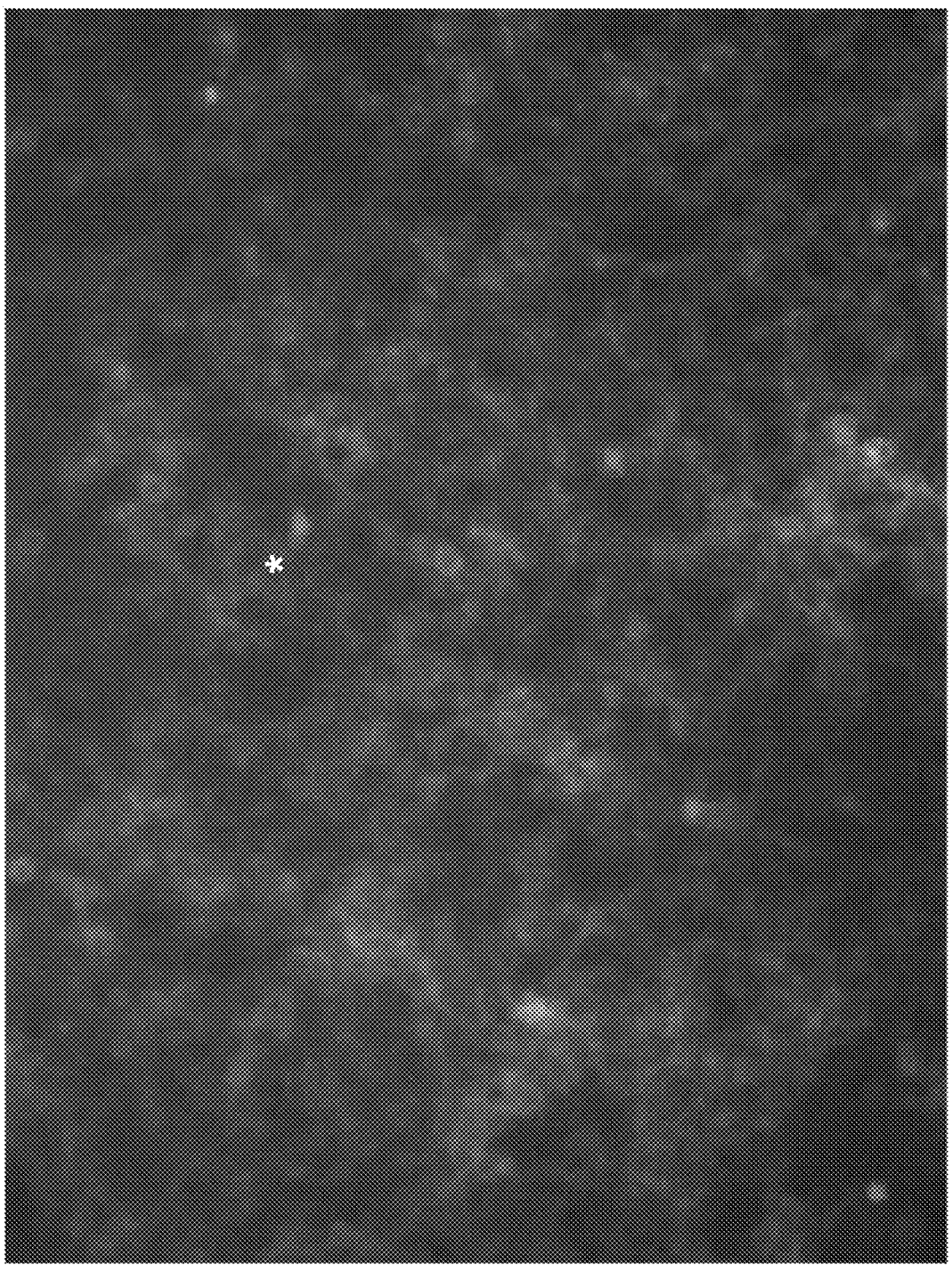
Figure 3E:
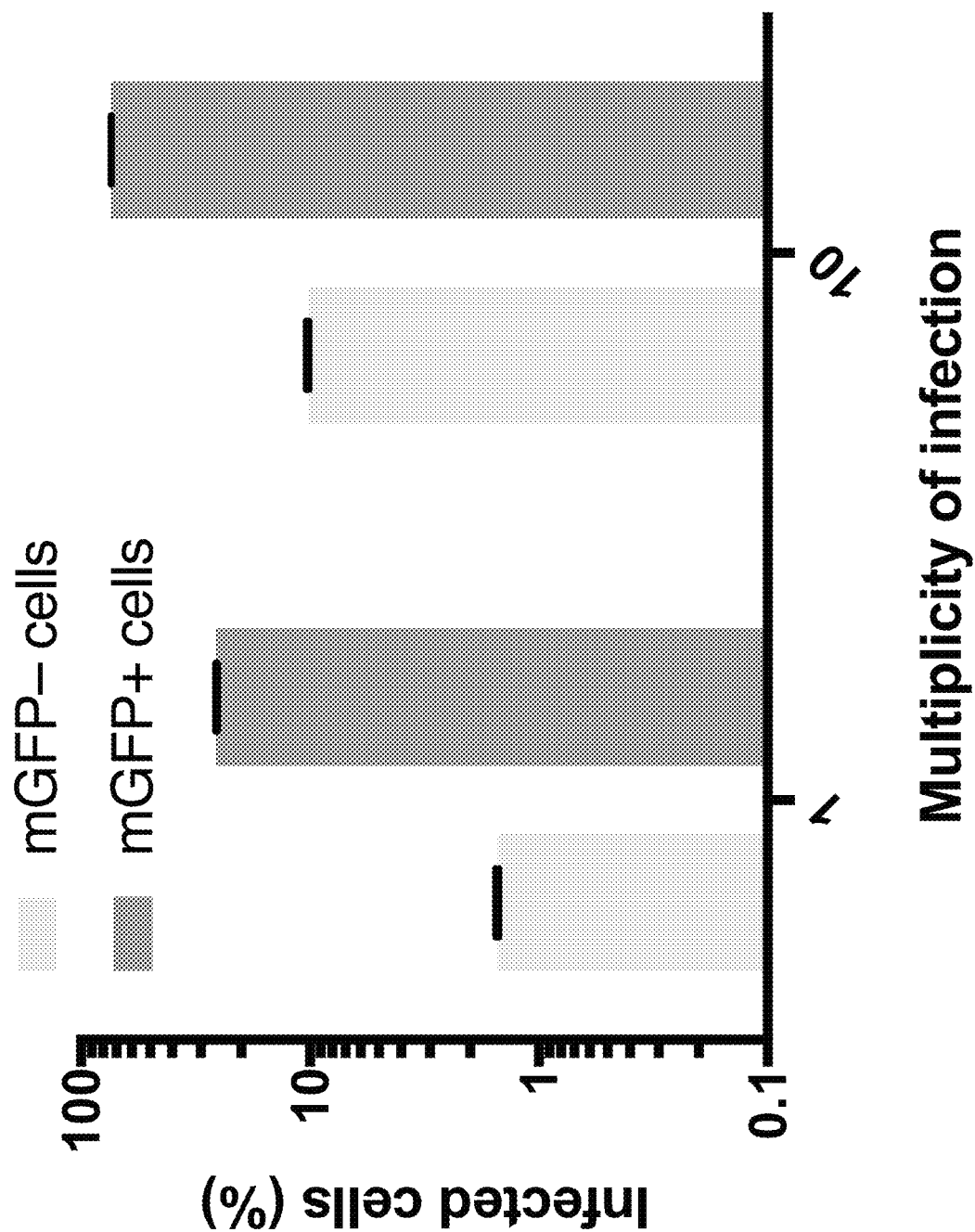

FIG. 3A shows a non-limiting exemplary schematic illustration of a second layer of control of the viral vector. FIG. 3B shows a non-limiting exemplary schematic illustration of a second layer of control of the viral vector. FIGS. 3C-3E depict data related to the bridge protein-mediated viral entry of target cells through a cell surface antigen. A rabies viral vector was engineered to encode an mCherry transgene and stably integrated HEK293T cells express surface extracellular GFP. As shown in FIG. 3C, EnvA-pseudotyped Rabies (RVdG-mCherry+EnvA) viruses can specifically enter surface GFP-expressing cells (indicated by mCherry expression, see asterix) in the presence of a TVA-GFP nanobody bridge protein. However, as shown in FIG. 3D, the viral vector cannot enter surface GFP-expressing cells in the presence of soluble TVA. As shown in FIG. 3E, transduction of target cells was dependent on expression of GFP on the surface of the target cell.

Example 3

Conditional Replication Mediated by a Conditionally Stable Fusion Protein

This example demonstrates the conditional replication of a viral vector with the use of a conditionally stable fusion protein.

Figure 4A:
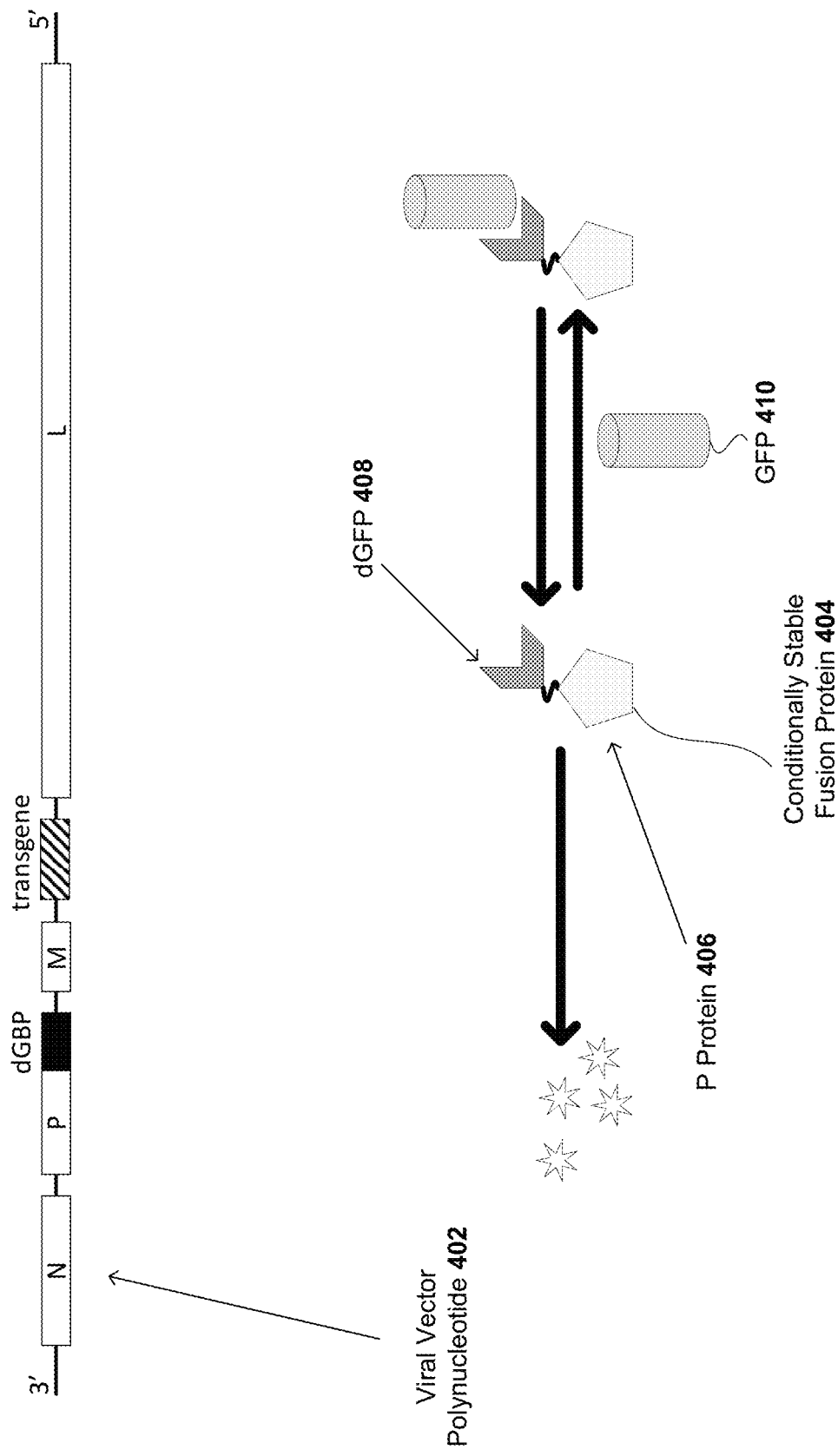
FIG. 4A shows a non-limiting exemplary schematic illustration of a third layer of control of the viral vector provided herein.
Figure 4B:
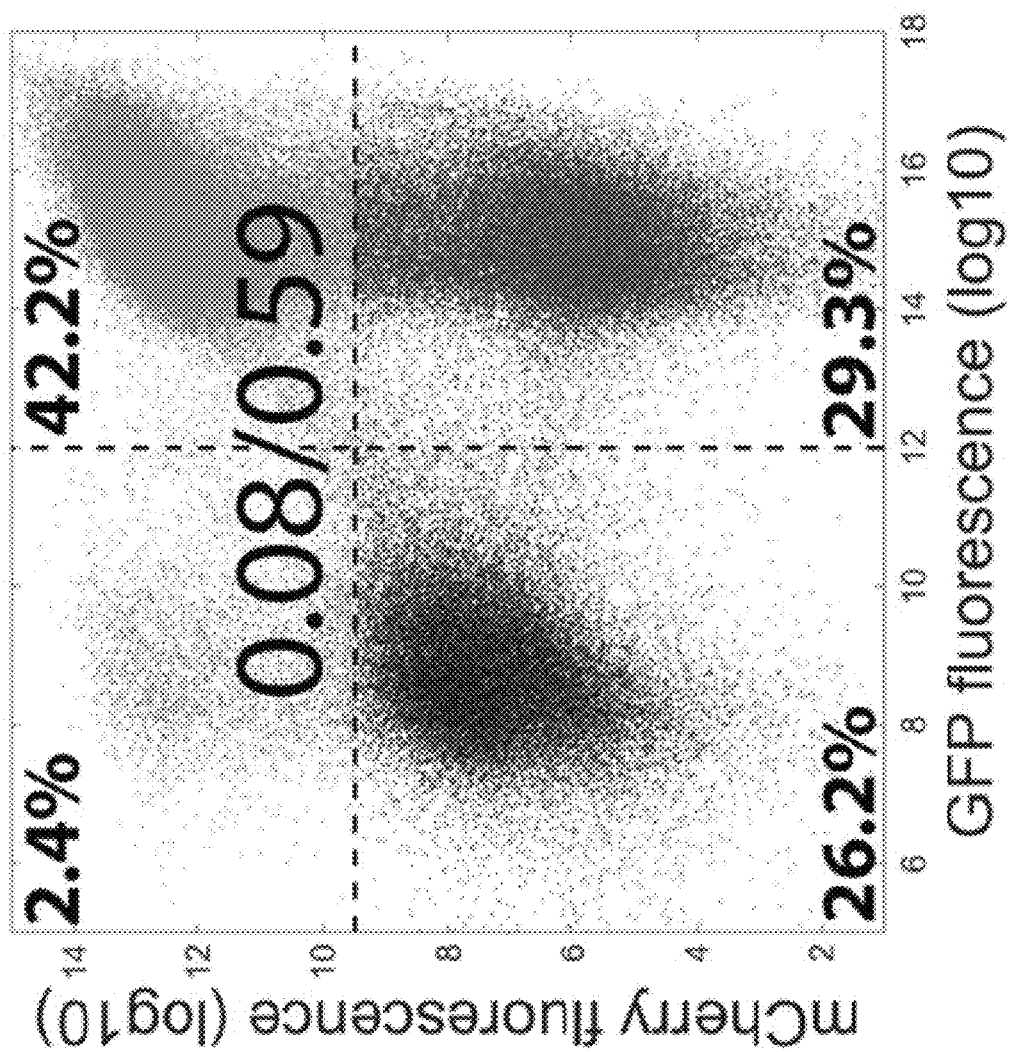
FIGS. 4B-4D depict data related to the conditional replication of a viral vector with the use of a conditionally stable fusion protein.
Figure 4C:
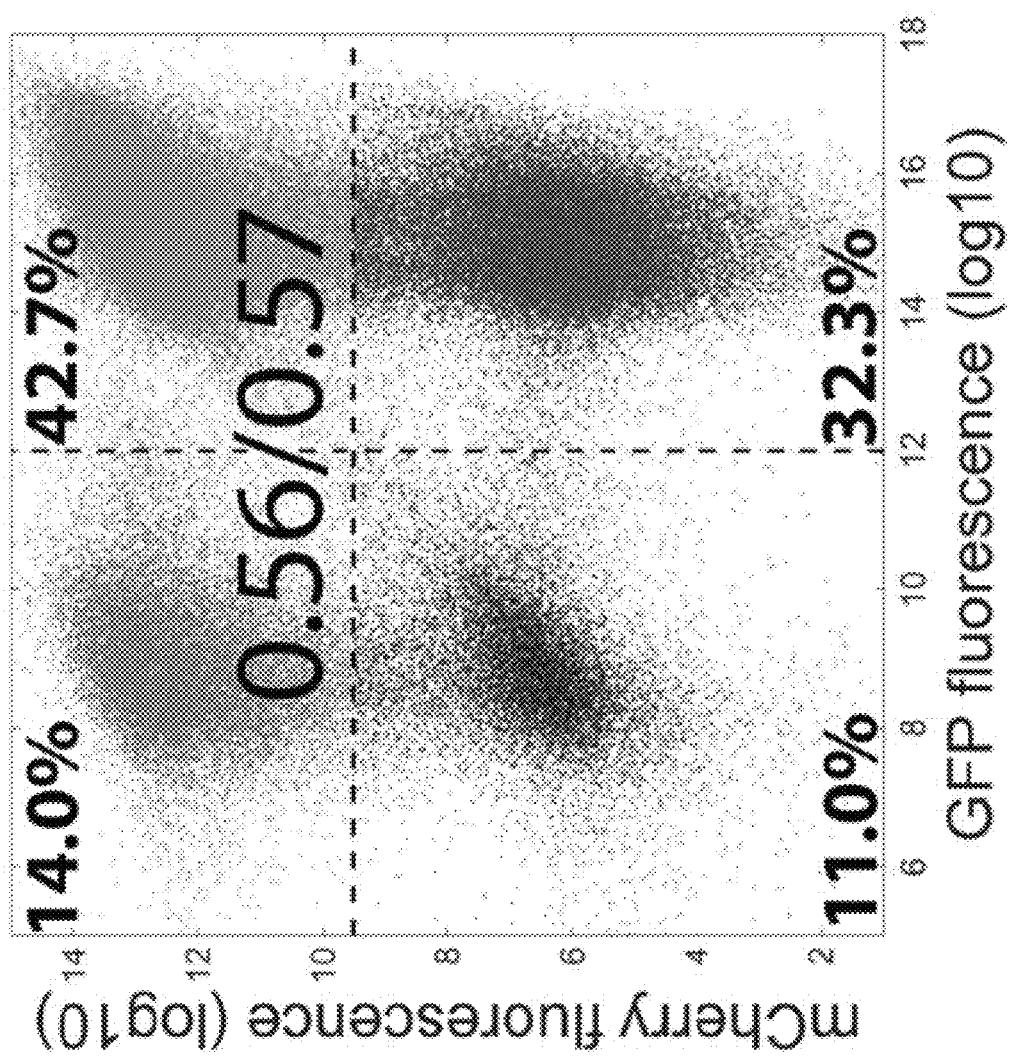
Figure 4D:
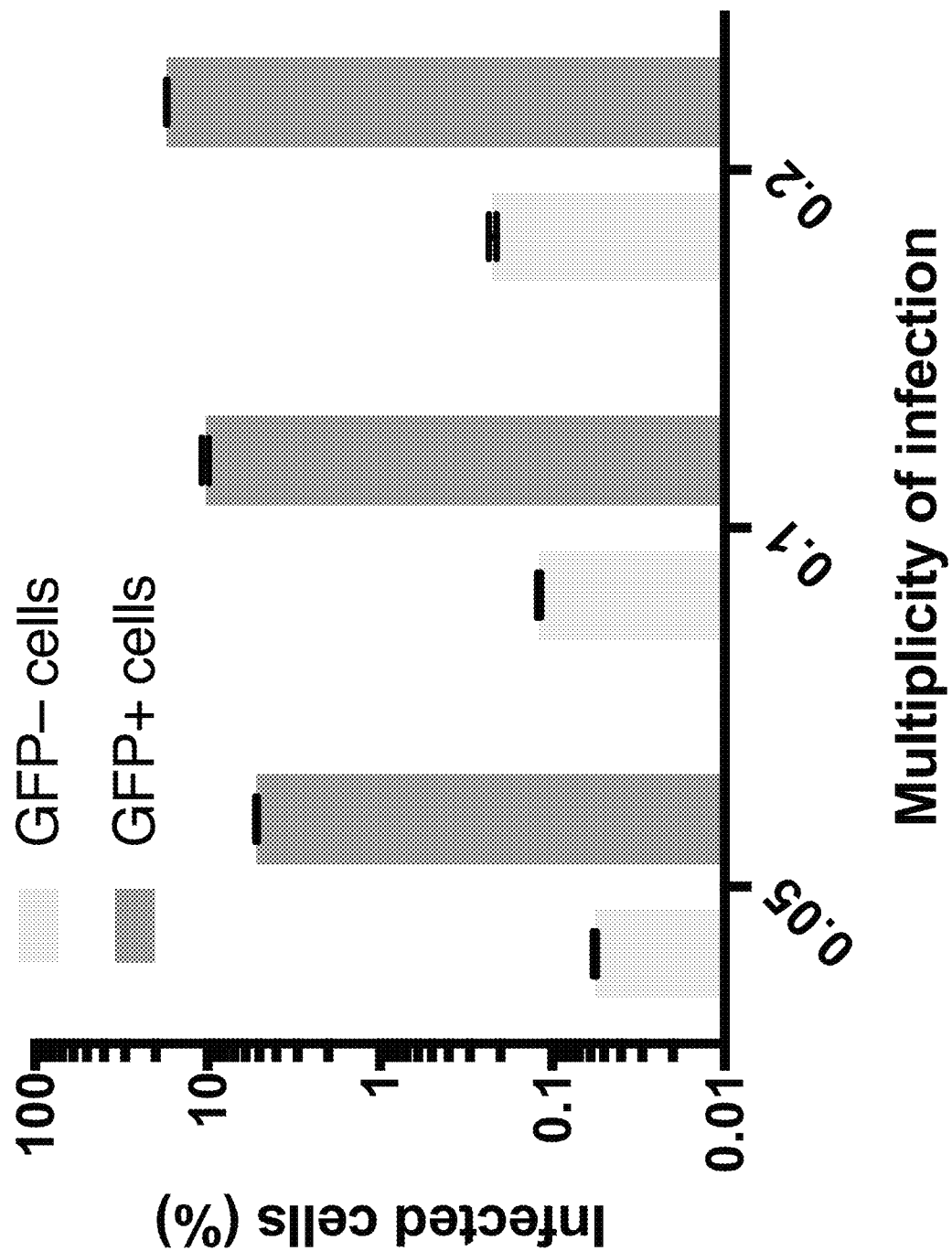

FIG. 4A shows a non-limiting exemplary schematic illustration of a third layer of control of the viral vector. Phosphoprotein was fused to a mutant nanobody that functions as a degron (dGBP) and is stabilized by binding to GFP. Co-cultured GFP−/+HEK293 cells were infected with mCherry-expressing RV (see FIG. 4A) and cultured for 2 days. FIGS. 4B-4D depict data related to the conditional replication of a viral vector with the use of a conditionally stable fusion protein. Rabies viral vector comprising the conditionally stable fusion protein exhibited selectivity for GFP-expressing cells (FIG. 4B, where #/# indicates the fraction of infected cells in GFP −/+ cells, respectively) while a rabies viral vector not comprising the conditionally stable fusion protein did not exhibit such selectivity (FIG. 4C). The Rabies viral vector comprising the conditionally stable fusion protein exhibited selectivity for GFP-expressing cells at a range of multiplicity of infection (FIG. 4D).

Example 4

External Control of Viral Vector Replication by a Protease Fusion Protein

This example demonstrates the use of a protease fusion protein to mediate external control of viral vector replication.

Figure 5A:
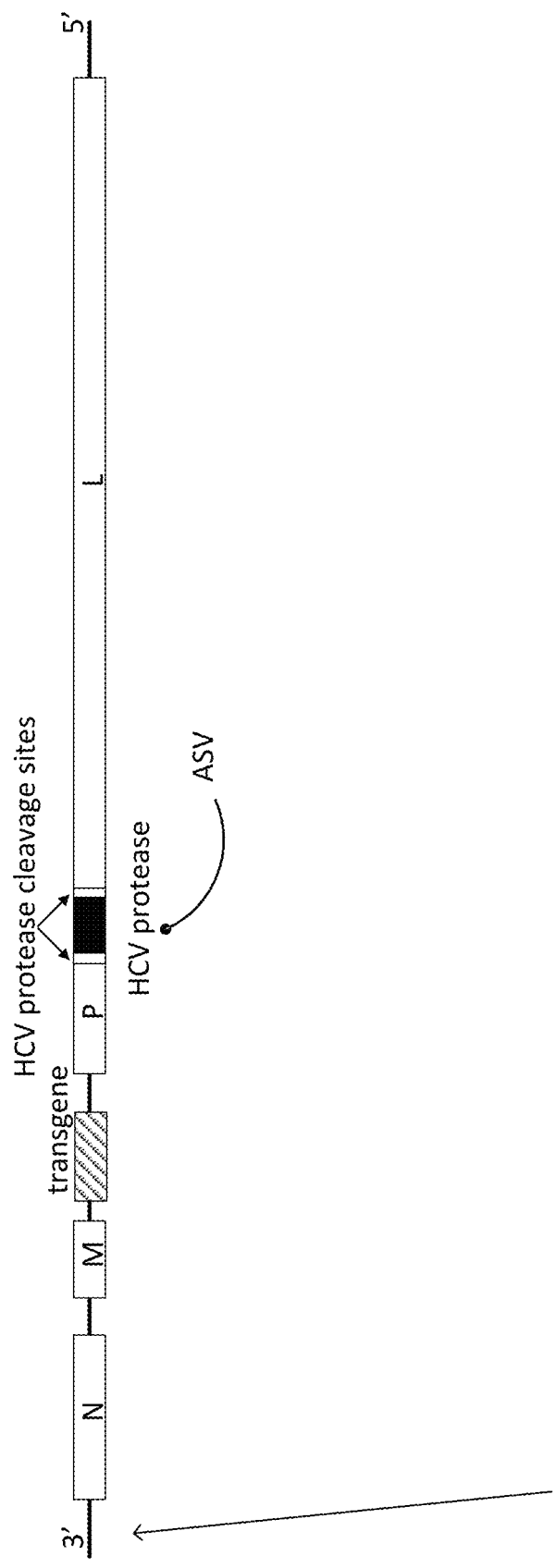
FIG. 5A shows a non-limiting exemplary schematic illustration of a fourth layer of control of the viral vector provided herein.
Figure 5B:
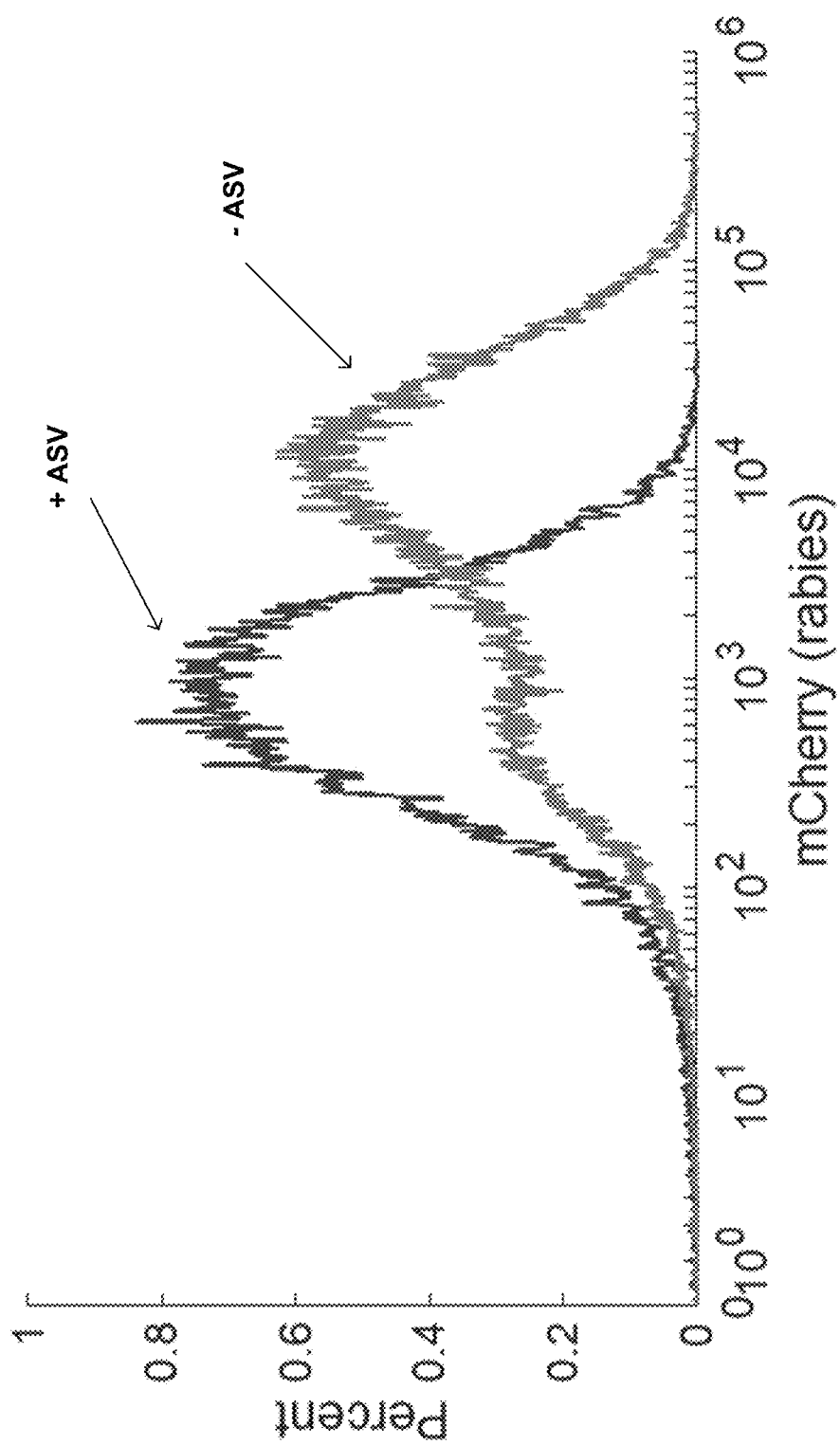
FIGS. 5B-5C depict data related to the conditional replication of a viral vector with the use of a protease fusion protein.
Figure 5C:
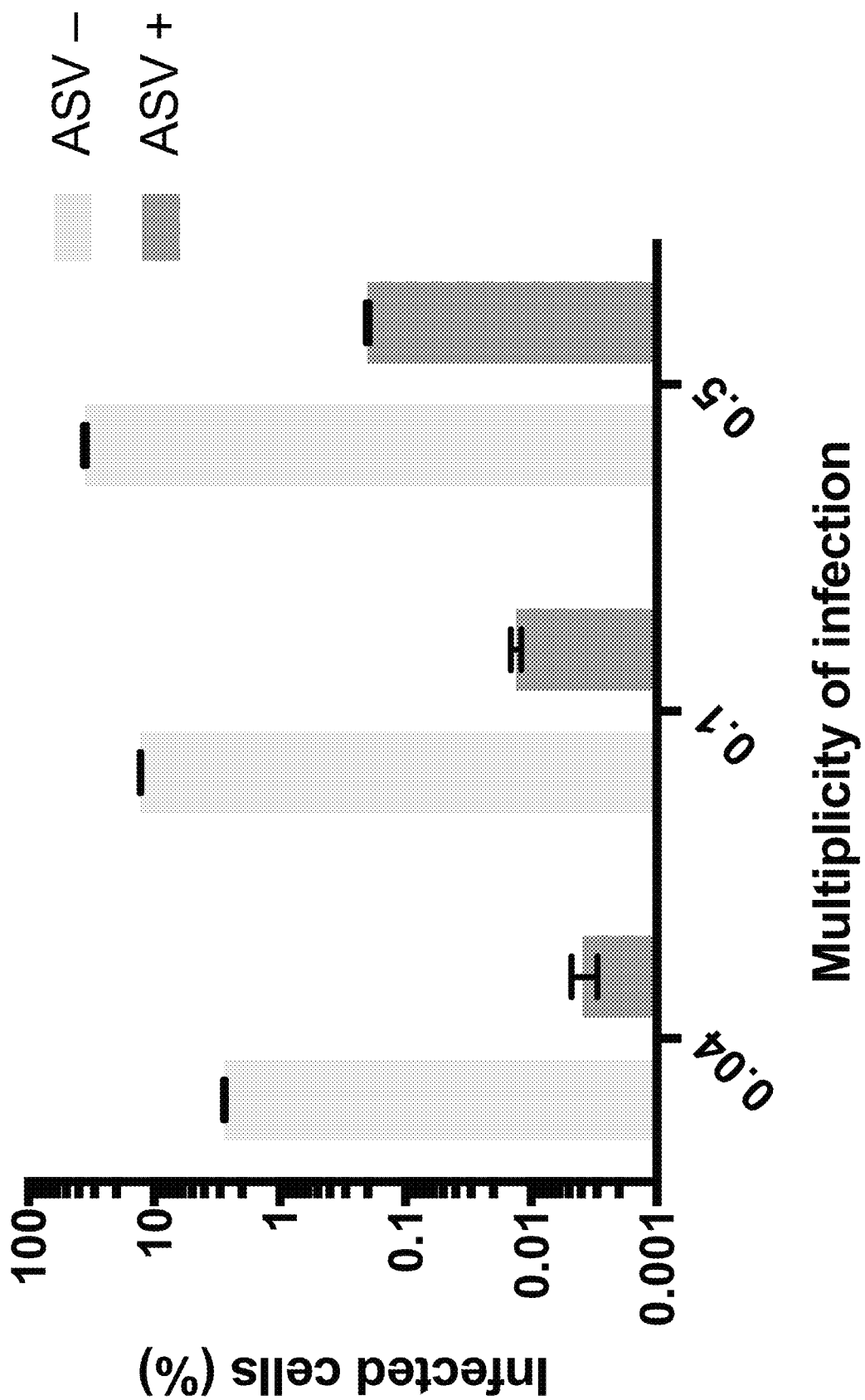

FIG. 5A shows a non-limiting exemplary schematic illustration of a fourth layer of control of the viral vector. HEK293 cells were infected with P-HCV-L-mCherryΔG rabies (shown in FIG. 5A; 80 day passaged), and cultured for 2 days in the absence or presence of ASV, a HCV-protease inhibitor. FIGS. 5B-5C depict data related to the conditional replication of a viral vector with the use of a protease fusion protein. As seen in FIGS. 5B-5C, the protease fusion protein rendered viral vector replication drug-sensitive, as infection of cells (indicated by mCherry expression) was eliminated in the presence of ASV. The protease fusion protein of SEQ ID NO: 1, encoded by the DNA of SEQ ID NO: 2, comprises P (residues 1-297 of SEQ ID NO: 1), HCV cleavage sites (residues 303-309 and 530-536 of SEQ ID NO: 1), NS4A peptide (residues 316-327 of SEQ ID NO: 1), HCV NS3 Protease (residues 332-524 of SEQ ID NO: 1), and L (residues 537-2662 of SEQ ID NO: 1). In some embodiments, the protease fusion proteins provided herein comprises a cofactor for the protease (e.g., NS4A peptide).

Example 5

External Control of Viral Vector Replication by a Degron Fusion Protein

This example demonstrates the use of a degron fusion protein to mediate external control of viral vector replication.

Figure 6A:
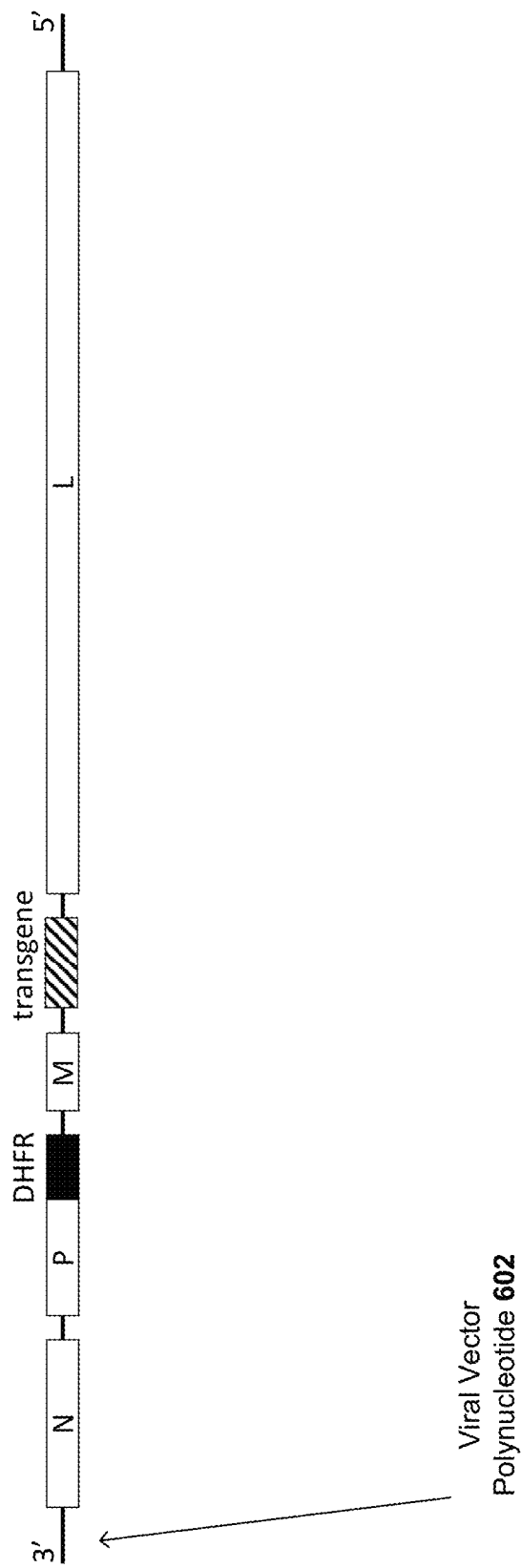
FIG. 6A shows a non-limiting exemplary schematic illustration of a fourth layer of control of the viral vector provided herein.
Figure 6B:
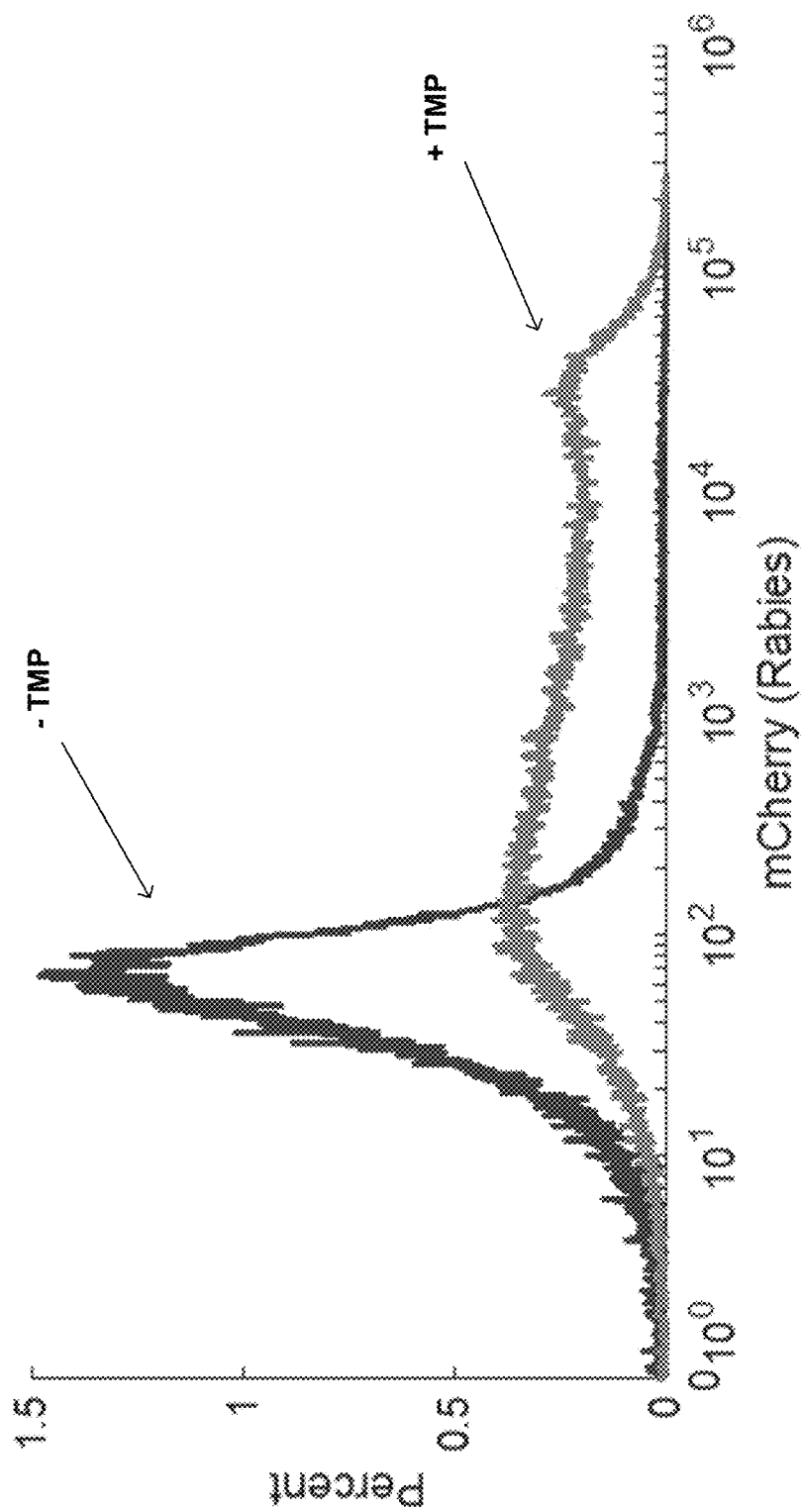
FIG. 6B depicts data related to the conditional replication of a viral vector with the use of a degron fusion protein.

FIG. 6A shows a non-limiting exemplary schematic illustration of a fourth layer of control of the viral vector. HEK293 cells were infected with P-DHFR mCherry ΔG rabies (RVdG-PDHFR-mCherry; shown in FIG. 6A; 20 day passage), and cultured for 2 days in the absence or presence of TMP, a stabilizer of DHFR degron. FIG. 6B depicts data related to the conditional replication of a viral vector with the use of a degron fusion protein. As seen in FIG. 6B, the degron fusion protein rendered viral vector replication drug-sensitive, as infection of cells (indicated by mCherry expression) was eliminated in the absence of TMP. The degron fusion protein of SEQ ID NO: 3, encoded by the DNA of SEQ ID NO: 4, comprises P (residues 1-297 of SEQ ID NO: 3), a TEV site (residues 303-309 of SEQ ID NO: 3), and GBP1 (residues 314-430 of SEQ ID NO: 3).

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A viral vector, comprising:
a polynucleotide encoding a nucleoprotein (N), a phosphoprotein (P), a matrix protein (M), an RNA-dependent RNA polymerase (L), and one or more transgenes,
wherein at least one of the N, P, M, or L is a degron fusion protein comprising a degron capable of binding a degron stabilizing molecule, and
wherein the degron fusion protein changes from a destabilized state to a stabilized state when the degron binds to the degron stabilizing molecule;
wherein at least one of the N, P, M, or L is a conditionally stable fusion protein comprising a stabilizing molecule binding domain capable of binding a stabilizing molecule, and wherein the conditionally stable fusion protein changes from a destabilized state to a stabilized state when the stabilizing molecule binding domain binds to the stabilizing molecule, and/or
wherein two of the N, P, M, or L are expressed as a protease fusion protein comprising a first protein and a second protein of the two of the N, P, M, or L separated from a protease by a first cut site and a second cut site, respectively, wherein the protease is capable of cutting the first cut site and the second cut site when the protease is not bound by a protease inhibitor, and wherein the first protein and the second protein are in inactive states when the first cut site and the second cut site are not cut, respectively.

2. The viral vector of claim 1, wherein the degron stabilizing molecule is an endogenous molecule of a target cell, a molecule specific to a cell type, a molecule specific to a disease or disorder, an exogenous molecule of a target cell, a synthetic protein circuit component, or any combination thereof, and/or wherein the degron stabilizing molecule comprises trimethoprim (TMP), a dihydrofolate reductase (DHFR) degron, or a combination thereof.

3. The viral vector of claim 1,
wherein the polynucleotide is capable of being replicated when the degron fusion protein is in the stabilized state,
wherein the polynucleotide is not capable of being replicated when the degron fusion protein is in the destabilized state,
wherein the polynucleotide is not capable of being replicated when the degron stabilizing molecule is absent, and/or
wherein the polynucleotide is capable of being replicated at a threshold concentration of the degron stabilizing molecule.

4. The viral vector of claim 1, wherein the P is a conditionally stable fusion protein and/or the degron fusion protein.

5. The viral vector of claim 1, wherein the stabilizing molecule binding domain comprises a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), an RNA aptamer, adNectin, iMab, anticalin, microbody, peptide aptamer, designed ankyrin repeat protein (DARPin), affilin, tetranectin, avimer, affibody, Kunitz domain, or any combination thereof.

6. The viral vector of claim 1, wherein the stabilizing molecule is an endogenous molecule of a target cell, a molecule specific to a cell type, a molecule specific to a disease or disorder, an exogenous molecule of a target cell, a synthetic protein circuit component, or any combination thereof.

7. The viral vector of claim 1,
wherein the polynucleotide is capable of being replicated when the conditionally stable fusion protein is present,
wherein the polynucleotide is capable of being replicated only when the conditionally stable fusion protein is present,
wherein the polynucleotide is capable of being replicated when the conditionally stable fusion protein is in the stabilized state,
wherein the polynucleotide is not capable of being replicated when the conditionally stable fusion protein is in the destabilized state,
wherein the polynucleotide is not capable of being replicated when the stabilizing molecule is absent,
wherein the polynucleotide is capable of being replicated at a threshold concentration of the stabilizing molecule,
wherein the polynucleotide is not capable of being replicated when the stabilizing molecule is present, and/or
wherein the polynucleotide is capable of being replicated at below a threshold concentration of the stabilizing molecule.

8. The viral vector of claim 1, wherein the protease is in an active state when the first cut site and the second cut site are not cut.

9. The viral vector of claim 1, wherein the protease fusion protein comprises the protease, the first cut site, the second cut site, the P, and the L, and wherein
the 5'-to-3' orientation of the protease fusion protein is 5'-the P-the first cut site-the protease-the second cut site-the L-3', and/or the P and/or the L are in inactive states when the first cut site and/or the second cut site are not cut.

10. The viral vector of claim 1, wherein the protease comprises a hepatitis C virus (HCV) protease, asunaprevir, simeprevir, telaprevir, sovaprevir, danoprevir, ciluprevir, boceprevir, paritaprevir, or any combination thereof.

11. The viral vector of claim 1,
wherein the polynucleotide is capable of being replicated when the first protein and the second protein are in active states,
wherein the first protein and the second protein are in active states when the protease inhibitor is absent,
wherein the polynucleotide is capable of being replicated when the protease inhibitor is absent,
wherein the polynucleotide is not capable of being replicated when the first protein and the second protein are in inactive states,
wherein the first protein and the second protein are in inactive states when the protease inhibitor is present,
wherein the polynucleotide is not capable of being replicated when the protease inhibitor is present,
wherein the first protein and the second protein are in inactive states at a threshold concentration of the protease inhibitor, and/or
wherein the polynucleotide is not capable of being replicated at a threshold concentration of the protease inhibitor.

12. The viral vector of claim 1, wherein the one or more transgenes comprises:
(a) a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof;
(b) cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof; and/or
(c) a synthetic protein circuit component.

13. The viral vector of claim 1,
wherein the viral vector is an RNA viral vector,
wherein the polynucleotide is derived from (a) a single-stranded RNA virus; (b) a positive sense RNA virus, a negative sense RNA virus, an ambisense RNA virus, or any combination thereof; or (c) a negative-strand RNA virus, optionally from one or more negative-strand RNA viruses of the order Mononegavirales, and/or
wherein the nucleoprotein (N), phosphoprotein (P), matrix protein (M), and/or RNA-dependent RNA polymerase (L) are derived from one or more negative-strand RNA viruses of the order Mononegavirales.

14. The viral vector of claim 13,
wherein the one or more negative-strand RNA viruses of the order Mononegavirales comprise a bornaviridae virus, a filoviridae virus, a nyamiviridae virus, a paramyxodiridae virus, a rhabdoviridae virus, or any combination thereof,
wherein the one or more negative-strand RNA viruses of the order Mononegavirales comprise rabies virus, sendai virus, vesicular stomatitis virus, or any combination thereof,
wherein the one or more negative-strand RNA viruses of the order Mononegavirales comprise one or more attenuating mutations,
wherein the one or more negative-strand RNA viruses of the order Mononegavirales comprise an attenuated rabies virus strain, and/or
wherein the attenuated rabies virus strain comprises CVS-N2c, CVS-B2c, DRV-4, RRV-27, SRV-16, ERA, CVS-11, SAD B19, SPBN, SN-10, SN10-333, PM, LEP, SAD, or any combination thereof.

15. The viral vector of claim 1,
wherein the polynucleotide is evolutionarily stable for at least 100 days of serial passaging, and/or
wherein, after 50 days or after 300 days of serial passaging (a) the polynucleotide is not capable of being replicated when the stabilizing molecule is absent, (b) the polynucleotide is not capable of being replicated when the protease inhibitor is present, and/or (c) the polynucleotide is not capable of being replicated when the degron stabilizing molecule is absent.

16. The viral vector of claim 1, wherein the viral vector comprises an envelope comprising a glycoprotein not encoded by the polynucleotide,
wherein the glycoprotein is of the species of any of the N, P, M, and L encoded by the polynucleotide, and/or wherein the glycoprotein, or a portion thereof, is derived of another species, and
wherein a glycoprotein binding domain of a first bridge protein is capable of binding the glycoprotein.

17. The viral vector of claim 16, wherein the glycoprotein comprises EnvA, EnvB, EnvC, EnvD, EnvE, EnvJ, or a portion thereof.

18. The viral vector of claim 16, wherein a glycoprotein binding domain of a first bridge protein is capable of binding the glycoprotein, wherein a first antigen-binding moiety of the first bridge protein is capable of binding a first antigen on a surface of a target cell, and wherein the viral vector is capable of transducing the target cell when the first antigen-binding moiety is bound to the first antigen and the glycoprotein binding domain is bound to the glycoprotein and a receptor on the cell surface of the target cell.

19. A system for delivering a polynucleotide to a target cell of a subject in need thereof, comprising: a viral vector of claim 1 or a sender cell capable of releasing a viral vector of claim 1; and a first bridge protein comprising a glycoprotein binding domain and a first antigen-binding moiety, wherein the glycoprotein binding domain is capable of binding the glycoprotein, wherein the first antigen-binding moiety is capable of binding a first antigen on a surface of a target cell, and wherein the viral vector is capable of transducing the target cell when the first antigen-binding moiety is bound to the first antigen and the glycoprotein binding domain is bound to the glycoprotein, or wherein the sender cell is capable of releasing the first bridge protein.

20. A method of controlling virus vector, comprising:
causing a polynucleotide of a viral vector to be internalized into a cell of a subject, wherein the polynucleotide encodes a nucleoprotein (N), a phosphoprotein (P), a matrix protein (M), an RNA-dependent RNA polymerase (L), and one or more transgenes; and
causing a stabilizing molecule to be present in or expressed by the cell, wherein at least one of the N, P, M, or L is a conditionally stable fusion protein comprising a stabilizing molecule binding domain, thereby the conditionally stable fusion protein changes from a destabilized state to a stabilized state when the stabilizing molecule binding domain binds the stabilizing molecule, and thereby a copy of the polynucleotide is generated from the polynucleotide; and/or causing a protease inhibitor to be absent in the cell, wherein two of the N, P, M, or L are expressed as a protease fusion protein comprising a first protein and a second protein of the two of the N, P, M, or L separated from a protease by a first cut site and a second cut site, respectively, thereby the protease cuts the first cut site and the second cut site to generate the first protein and the second protein are in active states, and thereby a copy of the polynucleotide is generated from the polynucleotide.

* * * * *